US012799461B2

(12) United States Patent
Sode et al.

(10) Patent No.: US 12,799,461 B2
(45) Date of Patent: Nov. 17, 2026

(54) MUTANT GLUCOSE DEHYDROGENASE HAVING IMPROVED THERMAL STABILITY, AND USE THEREOF

(71) Applicants: The University of North Carolina at Chapel Hill, Chapel Hill, NC (US); ARKRAY, Inc., Kyoto (JP)

(72) Inventors: Koji Sode, Chapel Hill, NC (US); Junko Shimazaki, Chapel Hill, NC (US); Katsuhiro Kojima, Tokyo (JP); Masashi Tsukada, Kyoto (JP)

(73) Assignees: The University of North Carolina at Chapel Hill, Chapel Hill, NC (US); ARKRAY, Inc., Kyoto (JP)

( * ) Notice: Subject to any disclaimer, the term of this patent is extended or adjusted under 35 U.S.C. 154(b) by 877 days.

(21) Appl. No.: 17/507,800

(22) Filed: Oct. 21, 2021

(65) Prior Publication Data

US 2022/0306996 A1 Sep. 29, 2022

Related U.S. Application Data

(63) Continuation-in-part of application No. 17/215,476, filed on Mar. 29, 2021, now abandoned.

(51) Int. Cl.
*C12N 9/04* (2006.01)

(52) U.S. Cl.
CPC ...... *C12N 9/0006* (2013.01); *C12Y 101/9901* (2013.01)

(58) Field of Classification Search
CPC ............ C12N 9/0006; C12Y 101/9901; C12Y 101/05; C12R 2001/01
See application file for complete search history.

(56) References Cited

U.S. PATENT DOCUMENTS

| | | | | |
|---|---|---|---|---|
| 8,945,359 | B2 | 2/2015 | Honda et al. | |
| 9,074,239 | B2 | 7/2015 | Tajima et al. | |
| 2004/0191883 | A1 | 9/2004 | Sode et al. | |
| 2012/0107903 | A1* | 5/2012 | Sode .................... | C12N 9/0006 435/190 |
| 2020/0110080 | A1 | 4/2020 | Sode et al. | |

FOREIGN PATENT DOCUMENTS

| | | | |
|---|---|---|---|
| JP | 2012-090563 | A | 5/2012 |
| JP | 2020-076747 | A | 5/2020 |
| WO | 02/072839 | A1 | 9/2002 |
| WO | 2017/013495 | A2 | 1/2017 |
| WO | 2017/013495 | A3 | 1/2017 |
| WO | 2017/013495 | A9 | 1/2017 |

OTHER PUBLICATIONS

Yamashita et al. Current Opinion in Electrochemistry, 2018, 12, 92-100 (Year: 2018).*
Hirakawa et al. Biotech. and Bioengin., 2013, 110, 1858-1864 (Year: 2013).*
Yoshida et al. Acta Cryst., 2019, D75, 841-851 (Year: 2019).*
Sakai et al., "Stabilization of fungi-derived recombinant FAD-dependent glucose dehydrogenase by introducing a disulfide bond," Biotechnology Letters, 37: 1091-1099 (2015).
Extended European Search Report issued in corresponding European Patent Application No. 21204332.7 dated May 17, 2022.
Liu et al., "Enhancing protein stability with extended disulfide bonds," PNAS, 113 (21): 5910-5915 (2016).
Hirakawa et al., "Introduction of Selective Intersubunit Disulfide Bonds into Self-Assembly Protein Scaffold to Enhance an Artificial Multienzyme Complex's Activity," Biotechnology and Bioengineering, 110 (7):1858-1864 (2013).
Yoshida et al., "X-ray structure of the direct electron transfer-type FAD glucose dehydrogenase catalytic subunit complexed with a hitchhiker protein," Acta Crystallograhica Section D, D75: 841-851 (2019).
Masakari et al., "Improvement in the thermal stability of Mucor prainii-derived FAD-dependent glucose dehydrogenase via protein chimerization," Enzyme and Microbial Technology, 132: 109387 (2020).
Yoshida et al., "X-ray structure of the direct electron transfer-type FAD glucose dehydrogenase catalytic subunit complexed with a hitchhiker protein," Acta Crystallographica Section D, D75: 841-851 (2019).
Office Action issued in corresponding Japanese Patent Application No. 2021-173100, dated Sep. 30, 2025.
Office Action issued in corresponding European Patent Application No. 21204332.7, dated Apr. 13, 2026.

* cited by examiner

*Primary Examiner* — Sharmila G Landau
*Assistant Examiner* — Lioubov G Korotchkina
(74) *Attorney, Agent, or Firm* — Morgan, Lewis & Bockius LLP

(57) ABSTRACT

The present invention provides a mutant FAD-dependent glucose dehydrogenase comprising: a catalytic subunit; an electron transfer subunit; and a hitchhiker subunit; wherein each of the amino acid sequence of the catalytic subunit and the amino acid sequence of the electron transfer subunit comprises a cysteine residue introduced therein, the catalytic subunit and the electron transfer subunit being bound to each other through a disulfide bond between the cysteine residues to achieve improved thermal stability of the FAD-dependent glucose dehydrogenase.

15 Claims, 14 Drawing Sheets

Specification includes a Sequence Listing.

MUTANT GLUCOSE DEHYDROGENASE HAVING IMPROVED THERMAL STABILITY, AND USE THEREOF

SEQUENCE LISTING SUBMISSION VIA EFS-WEB

A computer readable text file, entitled "SequenceListing.txt," created on Oct. 21, 2021 with a file size of 140,221 bytes contains the sequence listing for this application and is hereby incorporated by reference in its entirety.

TECHNICAL FIELD

The present invention relates to biotechnology, and to electrochemical measurement of glucose utilizing a mutant glucose dehydrogenase.

BACKGROUND ART

For improvement of the thermal stability of proteins, a number of methods have been developed. Known examples of artificial approaches therefor include glycosylation, chemical cross-linking and binding to polymers. These methods are widely applicable to arbitrary target proteins since the methods comprehensively protect the target proteins to achieve stabilization of the proteins. However, in cases of enzymes, these methods have a non-negligible effect on the activity of the enzyme, low-reproducibility of the results, leading to practical problems such as requirement of an additional step for purification and modification.

U.S. Pat. Nos. 9,074,239, and 8,945,359 disclose techniques for improvement of the thermal stability of FAD-dependent glucose dehydrogenase (FAD-GDH) by site-directed mutagenesis. However, those documents do not suggest stabilization of binding between subunits in relation to mutagenesis in a catalytic subunit. U.S. Pat. No. 8,945,359 describes that the specific activity of the mutant at 50° C. is only 50% relative to the specific activity at 30° C., and that the mutant is deactivated at a high temperature condition of 60° C.

Biotechnol Lett 1774-8 (2015) reports that a mutant enzyme containing cysteine residues introduced at two specific sites of a catalytic subunit showed improved thermal resistance while maintaining the activity and specificity.

SUMMARY OF THE INVENTION

Glucose dehydrogenase is an enzyme often used for glucose sensors.

Glucose sensors for daily use in self-blood glucose measurement by diabetic patients are required to show accurate measured values in any situation or environment. Therefore, the enzyme, which is a key factor of the performance, is required to have high stability so as to avoid heat inactivation.

Based on information on the crystal structure of FAD-GDH, which is a heterotrimer comprising an electron transfer subunit, the present inventors introduced cysteine residues to specific sites on an intersubunit interface to form a disulfide bond on the interface, to thereby succeed in stabilization of the higher-order structure of the heterotrimer and remarkable improvement of the thermal resistance. Further, since the electron transfer activity of the mutant enzyme could be remarkably increased by introduction of cysteine residues to positions which are thought to be in the intramolecular electron transfer pathway of the enzyme, the present inventors found that the cysteine residues play an important role not only in cross-linking between the subunits, but also in assisting the electron transfer.

In one mode of the present invention, a mutant glucose dehydrogenase having improved thermal stability is provided without deterioration of the enzyme activity.

According to one aspect of the present invention, a mutant FAD-dependent glucose dehydrogenase comprising:

a catalytic subunit;

an electron transfer subunit; and a hitchhiker subunit;

wherein each of the amino acid sequence of the catalytic subunit and the amino acid sequence of the electron transfer subunit contains a cysteine residue introduced therein, the catalytic subunit and the electron transfer subunit being bound to each other through a disulfide bond between the cysteine residues, is provided.

According to another aspect of the present invention, the mutant FAD-dependent glucose dehydrogenase in which the amino acid sequence of the electron transfer subunit comprises another cysteine residue introduced therein, and in which the amino acid sequence of the hitchhiker subunit comprises a cysteine residue introduced therein, the hitchhiker subunit and the electron transfer subunit being bound to each other through a disulfide bond between the cysteine residues, is provided.

According to another aspect of the present invention, the mutant FAD-dependent glucose dehydrogenase in which the amino acid sequence of the catalytic subunit and the amino acid sequence of the electron transfer subunit contains a cysteine residue introduced therein, the catalytic subunit and the electron transfer subunit being bound to each other through a disulfide bond between the cysteine residues, and simultaneously, the amino acid sequence of the electron transfer subunit comprises another cysteine residue introduced therein, and in which the amino acid sequence of the hitchhiker subunit comprises a cysteine residue introduced therein, the hitchhiker subunit and the electron transfer subunit being bound to each other through a disulfide bond between the cysteine residues, is provided.

According to another aspect of the present invention, an enzyme electrode comprising the mutant FAD-dependent glucose dehydrogenase is provided.

According to another aspect of the present invention, a biosensor comprising the enzyme electrode is provided.

EMBODIMENTS FOR CARRYING OUT THE INVENTION

Figure 1:
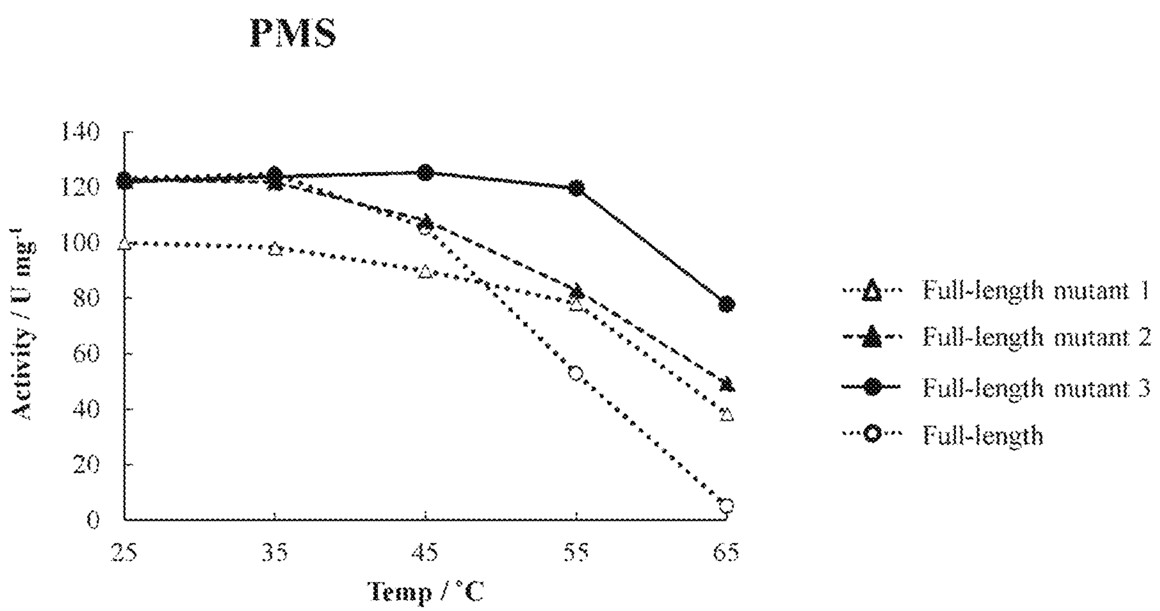
FIG. 1 is a graph illustrating the enzyme activity of each GDH from *Burkholderia cepacia* (Bc) (wild type or mutants 1 to 3 with a full-length β subunit) at 25° C. to 65° C.

The glucose dehydrogenase according to one embodiment of the present invention is an FAD-dependent glucose dehydrogenase comprising:

a catalytic subunit (α subunit);

an electron transfer subunit (β subunit); and a hitchhiker subunit (γ subunit);

wherein each of at least the catalytic subunit and the electron transfer subunit comprises a cysteine residue introduced therein, the cysteine residues forming a disulfide bond therebetween.

The glucose dehydrogenase is hereinafter also referred to as mutant glucose dehydrogenase (GDH) or mutant FAD-GDH.

Thus, the mutant glucose dehydrogenase is a trimer composed of three subunits. The subunits may be linked to each other through a linker(s) and/or the like.

Known examples of an FAD-GDH which is a trimer composed of the three subunits include those of *Burkholderia cepacia, Burkholderia cenocepacia, Burkholderia thailandensis, Ralstonia pickettii, Ralstonia solanacearum, Burkholderia phytofirmans, Ralstonia* sp., *Moraxellaceae bacterium, Pseudomonas knackmussii, Yersinia nurmii, Edaphovirga cremea, Silvimonas terrae, Zymobacter palmae, Cobetia* sp., *Halomonas* sp. and *Ewingella americana* The mutant FAD-GDH according to one embodiment of the present invention can be obtained by introducing mutations thereto.

According to one embodiment of the present invention, in the mutant FAD-GDH, each of the amino acid sequence of the catalytic subunit and the amino acid sequence of the electron transfer subunit comprises a cysteine residue introduced therein, the catalytic subunit and the electron transfer subunit being bound to each other through a disulfide bond between the cysteine residues. The introduction of a cysteine residue includes introduction by amino acid substitution and introduction by insertion.

Each subunit is described below using the FAD-GDH of *Burkholderia cepacia* as an example. However, the mutant GDH is not limited to the following embodiments.

The *Burkholderia cepacia* is not limited. For example, the *Burkholderia cepacia* KS1 strain may be used. The *Burkholderia cepacia* KS1 strain has been deposited with International Patent Organism Depositary, National Institute of Advanced Industrial Science and Technology (currently International Patent Organism Depositary (IPOD), National Institute of Technology and Evaluation (NITE)) as of Sep. 25, 2000 under the accession number FERM BP-7306.

<Catalytic Subunit>

The catalytic subunit, also called α subunit, is a polypeptide having a catalytic activity of glucose dehydrogenation dependently on FAD (flavin adenine dinucleotide). The catalytic subunit preferably contains an Fe—S cluster.

SEQ ID NO:3 is an amino acid sequence of the FAD-GDH catalytic subunit of the *Burkholderia cepacia* KS1 strain. The following description is given with reference to this sequence.

The cysteine introduction site in the amino acid sequence of the catalytic subunit is preferably in a region forming the interface with the electron transfer subunit in the spatial structure of the FAD-GDH. For example, cysteine is introduced to a position in the region of amino acid positions 200 to 240 of SEQ ID NO:3. Thus, an amino acid residue in the region of amino acid positions 200 to 240 of SEQ ID NO:3 is substituted with cysteine. This region in the catalytic subunit is a region located on the interface with the electron transfer subunit in the spatial structure of GDH.

Specific examples of the amino acid in this region include the proline residue at position 205, glycine residue at position 208, asparagine residue at position 215, isoleucine residue at position 224, and glutamic acid residue at position 235 in the amino acid sequence of SEQ ID NO:3. Introduction of cysteine residue includes substitution by cysteine and insertion of cysteine. For example, any of the above-described amino acid residues may be substituted with a cysteine residue. Alternatively, when a cysteine residue is inserted, the cysteine residue may be inserted at a position immediately before or immediately after these residues.

The above-described positions of amino acid substitution are positions in SEQ ID NO:3. However, the amino acid sequence of the catalytic subunit to which the mutation is to be introduced may have a length different from the length of SEQ ID NO:3. For example, in cases where the amino acid sequence of the catalytic subunit to which the mutation is to be introduced is shorter by three amino acids in the N-terminal side compared to SEQ ID NO:3, the proline residue at position 205 of SEQ ID NO:3 corresponds to the proline at position 202 of the amino acid sequence. Such a case is also regarded as substitution of the proline residue corresponding to the "proline residue at position 205", and included in a mode of the present invention. The same applies to other residues.

Among the above-described residues, the proline residue at position 205 is preferably substituted by a cysteine residue. This proline residue exists in the amino acid motif "ARNSRPYD" (SEQ ID NO: 23). In one embodiment, a cysteine residue is introduced to substitute the proline residue in this motif, and thereby the catalytic subunit of the mutant glucose dehydrogenase such as one having an amino acid sequence at least 60, 70, 80, 90, or 95% identical to the amino acid sequence of SEQ ID NO:3, 7, 13, 17 or 21 comprises the amino acid sequence of "ARNSRCYD" (SEQ ID NO: 24).

FAD-GDH is also known in other microorganisms. In the amino acid sequence of their catalytic subunit, for example, in an amino acid sequence having an identity of at least 60%, at least 80%, at least 90%, or at least 95% to SEQ ID NO:3, cysteine may be introduced into the region described above, or to the position of the amino acid residue corresponding to the specific amino acid residue described above.

More specifically, the amino acid sequence of the catalytic subunit to which the mutation is to be introduced may be aligned with the amino acid sequence of SEQ ID NO:3, and an amino acid residue in the region of amino acid positions 200 to 240 of SEQ ID NO:3, for example, the amino acid whose position corresponds to the position of the proline residue at position 205, glycine residue at position 208, asparagine residue at position 215, isoleucine residue at position 224, or glutamic acid residue at position 235, may be substituted with cysteine.

Any polypeptide having some degree of a sequence identity to SEQ ID NO:3 or the other sequence of the catalytic subunit described below can be used to prepare a catalytic subunit of the mutant glucose dehydrogenase as long as it maintains the function of the catalytic subunit, i.e. forming a complex with the electron transfer subunit and the hitchhiker subunit and exhibiting glucose dehydrogenase activity.

Examples of the amino acid sequence of the GDH $\alpha$ subunit having an identity of not less than 60% to SEQ ID NO:3 include the sequence of the $\alpha$ subunit of each of the followings: *Burkholderia cenocepacia* J2315 strain (GenBank Accession No. WP 006482972), *Burkholderia thailandensis* TXDOH strain (WP_009900298), *Ralstonia pickettii* 12D strain (WP_012761508), *Ralstonia solanacearum* IPO1609 strain (WP_003265143), *Burkholderia phytofirmans* PsJN strain (WP_012428610), *Ralstonia* sp. (WP_048931828), *Moraxellaceae bacterium* (WP_114899537), *Pseudomonas knackmussii* (WP_043248521), *Yersinia nurmii* (WP_049596850), *Edaphovirga cremea* (WP_114193339), *Silvimonas terrae* (WP_184102398), *Zymobacter palmae* (WP_027705356), *Cobetia* sp. (WP_158773851), *Halomonas* sp. (WP_107334716) and *Ewingella americana* (WP_034788281).

As described above, the region and residues to which the cysteine residue is introduced in these catalytic subunits can be determined by aligning the sequence of each catalytic subunit with that of *B. cepacia* (SEQ ID NO: 3).

Figure 10:
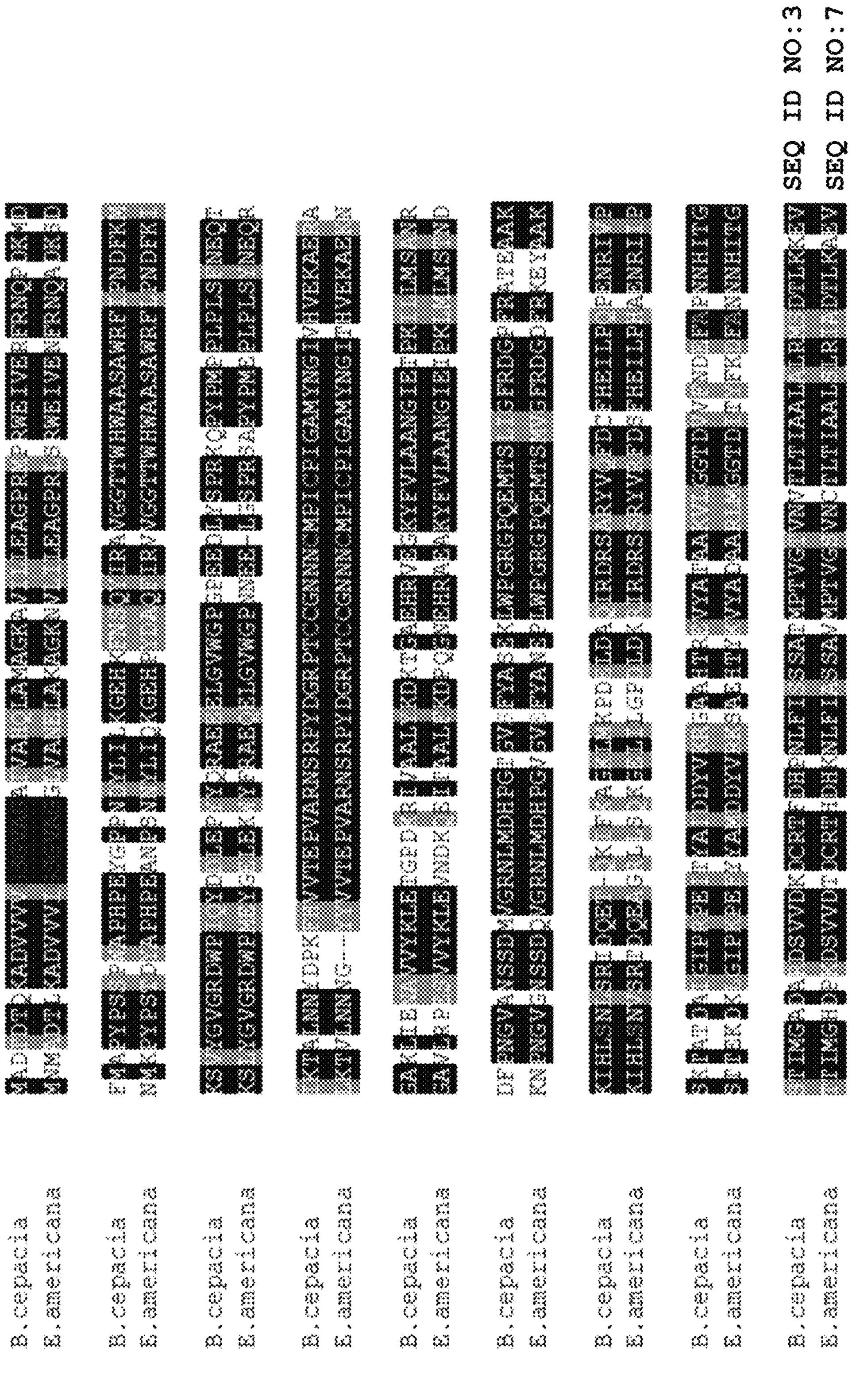
FIG. 10 shows the sequence alignment of the catalytic subunit between *Burkholderia cepacia* and *Ewingella americana*.

For example, in the case of the catalytic subunit of *E. americana* GDH (SEQ ID NO: 7), as shown in FIG. 10, the region 200-240 in SEQ ID NO: 3 is located in the region 197-237 of in SEQ ID NO: 7, and the proline residue at position 205, glycine residue at position 208, asparagine residue at position 215, isoleucine residue at position 224, and glutamic acid residue at position 235 respectively correspond to the proline residue at position 202, glycine residue at position 205, asparagine residue at position 212, isoleucine residue at position 221, and glutamic acid residue at position 232 in SEQ ID NO: 7.

Another embodiment of the catalytic subunit includes a catalytic subunit comprising an amino acid sequence having at least 60%, 80%, 90% or 95% identity to SEQ ID NO: 7 wherein cysteine is introduced at the position corresponding to the proline residue at position 202, glycine residue at position 205, asparagine residue at position 212, isoleucine residue at position 221, or glutamic acid residue at position 232 in SEQ ID NO: 7.

Figure 18:
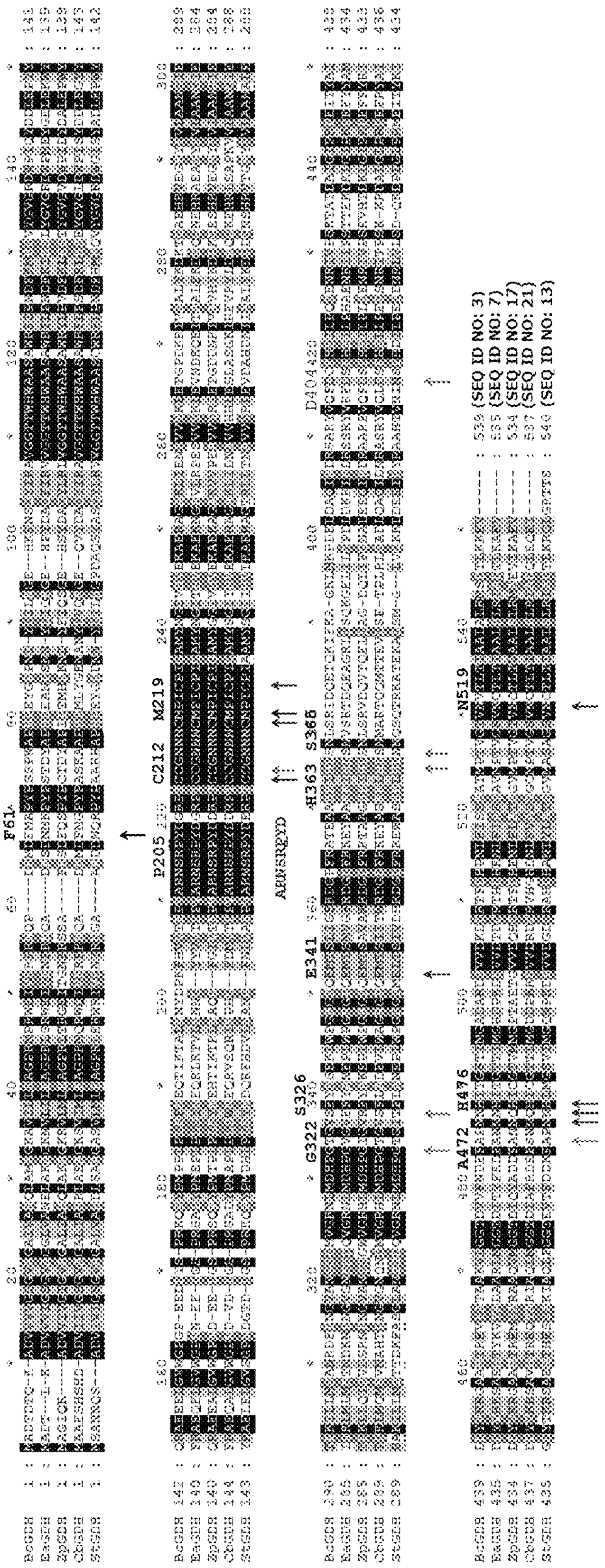
FIG. 18 shows the sequence alignment of the catalytic subunit between *Burkholderia cepacia, Ewingella americana, Silvimonas terrae, Zymobacter palmae* and *Cobetia* sp.

For example, in the case of the catalytic subunit of *Silvimonas terrae* GDH (SEQ ID NO: 13), as shown in FIG. 18, the proline residue at position 205 in SEQ ID NO: 3 corresponds to the proline residue at position 204 in SEQ ID NO: 13.

Another embodiment of the catalytic subunit includes a catalytic subunit comprising an amino acid sequence having at least 60%, 80%, 90% or 95% identity to SEQ ID NO: 13 wherein cysteine is introduced at the position corresponding to the proline residue at position 204 in SEQ ID NO: 13.

For example, in the case of the catalytic subunit of *Zymobacter palmae* GDH (SEQ ID NO: 17), as shown in FIG. 18, the proline residue at position 205 in SEQ ID NO: 3 corresponds to the proline residue at position 200 in SEQ ID NO: 17.

Another embodiment of the catalytic subunit includes a catalytic subunit comprising an amino acid sequence having at least 60%, 80%, 90% or 95% identity to SEQ ID NO: 17 wherein cysteine is introduced at the position corresponding to the proline residue at position 200 in SEQ ID NO: 17.

For example, in the case of the catalytic subunit of *Cobetia* sp. GDH (SEQ ID NO: 21), the proline residue at position 205 corresponds to the proline residue at position 204 in SEQ ID NO: 21.

Another embodiment of the catalytic subunit includes a catalytic subunit comprising an amino acid sequence having at least 60%, 80%, 90% or 95% identity to SEQ ID NO: 21 wherein cysteine is introduced at the position corresponding to the proline residue at position 204 in SEQ ID NO: 21.

The amino acid sequence of the catalytic subunit ($\alpha$ subunit) may contain not only the mutation that introduces cysteine, but also an additional mutation. Known examples of mutants comprising mutations in the catalytic subunit of FAD-dependent GDH derived from *Burkholderia cepacia* include a mutant in which the amino acid residues at positions 472 and 475 are substituted (WO 2005/103248), a mutant in which the amino acid residues at positions 326, 365, and 472 are substituted (QYY mutant JP 2012-090563 A), a mutant in which position 365 and position(s) 326, 472, 475, 529, and/or the like are substituted (WO 2006/137283). The catalytic subunit of the mutant GDH according to one embodiment of the present invention may have these mutations.

<Electron Transfer Subunit>

The electron transfer subunit is also called β subunit, and contains at least one heme-binding domain. The subunit has a function to transfer electrons generated by reaction using glucose as a substrate, to an electrode.

The electron transfer subunit comprises a cysteine residue introduced therein, and this cysteine residue forms a disulfide bond with the cysteine residue introduced to the catalytic subunit.

The electron transfer subunit is not limited as long as it has a function to transfer electrons generated by glucose dehydrogenation to an electrode. Electron transfer subunits derived from various organisms, including known electron transfer subunits, may be used. The electron transfer subunit may be derived from the same microorganism as the microorganism from which the catalytic subunit is derived. Examples of the electron transfer subunit include the electron transfer subunit of GDH of *Burkholderia cepacia*. Examples of the GDH electron transfer subunit of the *B. cepacia* KS1 strain include a polypeptide comprising the amino acid sequence of SEQ ID NO:4. SEQ ID NO:4 is an amino acid sequence of the GDH β subunit of the *Burkholderia cepacia* KS1 strain. The following description is given with reference to this sequence.

The cysteine introduction site in the amino acid sequence of the electron transfer subunit is preferably in a region forming the interface with the catalytic subunit. For example, cystein is introduced to a position in the region of amino acid positions 330 to 400 of the amino acid sequence of SEQ ID NO:4. Thus, an amino acid residue in the region of amino acid positions 330 to 400 of SEQ ID NO:4 is substituted with cysteine. This region in the electron transfer subunit is a region located on the interface with the catalytic subunit in the spatial structure of GDH.

More specific examples of the amino acid in this region include the threonine residue at position 336, glycine residue at position 385, aspartic acid residue at position 383, and tyrosine residue at position 391 in the amino acid sequence of SEQ ID NO:4. Any of these may be substituted with a cysteine residue. When a cysteine residue is inserted, the cysteine residue may be inserted at a position immediately before or immediately after these residues.

Among the above-described residues, the aspartic acid residue at position 383 is preferably substituted by a cysteine residue. This amino acid residue exists at a position three amino acids before the amino acid motif "MP(A/G)F" (SEQ ID NO: 25). In one embodiment, a cysteine residue is introduced to substitute the amino acid residue three amino acid before this motif, and thereby the electron transfer subunit of the mutant glucose dehydrogenase such as one having an amino acid sequence at least 60, 70, 80, 90, or 95% identical to the amino acid sequence of SEQ ID NO: 4, 8, 14, 18 or 22 comprises the amino acid sequence of "CXXMP(A/G)F" (SEQ ID NO: 26).

Examples of a preferred combination of the cysteine introduction site in the region in the catalytic subunit (the region of amino acid positions 200 to 240 of SEQ ID NO:3) and the cysteine introduction site in the region in the electron transfer subunit (the region of amino acid positions 330 to 400 of SEQ ID NO:4) include the combination of the proline at position 205 of the catalytic subunit and the aspartic acid at position 383 of the electron transfer subunit, and the combination of the asparagine at position 215 of the catalytic subunit and the threonine at position 336 of electron transfer subunit. These combinations of residues are combinations of residues having a distance of about 5 Å from each other in the spatial structure of FAD-GDH, and capable of more efficient formation of a disulfide bond.

The mutant glucose dehydrogenase may also be a mutant glucose dehydrogenase in which the amino acid sequence of the electron transfer subunit contains another cysteine residue introduced, which cysteine residue forms a disulfide bond with a cysteine residue introduced in the amino acid sequence of the hitchhiker subunit, to bind the hitchhiker subunit and the electron transfer subunit to each other.

The another cysteine residue is preferably introduced into a region of the electron transfer subunit which is on the interface with the hitchhiker subunit. Examples of such a region include the region of amino acid positions 341 to 350 in the amino acid sequence of SEQ ID NO:4. Thus, an amino acid residue in the region of amino acid positions 341 to 350 of SEQ ID NO:4 may be substituted with cysteine. This region in the electron transfer subunit is a region located on the interface with the hitchhiker subunit in the spatial structure of GDH.

More specific examples of the amino acid in this region include the threonine residue at position 345, proline residue at position 346, and tyrosine residue at position 349 in the amino acid sequence of the region of SEQ ID NO:4. Introduction of cysteine residue includes substitution by cysteine and insertion of cysteine. For example, any of the above-described amino acid residues may be substituted with a cysteine residue. Alternatively, when a cysteine residue is inserted, the cysteine residue may be inserted at a position immediately before or immediately after these residues.

Among the above-described residues, the tyrosine residue at position 349 is preferably substituted by a cysteine residue. This amino acid residue exists at a position one amino acid before the amino acid motif "YPS(L/M)" (SEQ ID NO: 27). In one embodiment, a cysteine residue is introduced to substitute the amino acid residue one amino acid before this motif, and thereby the electron transfer subunit of the mutant glucose dehydrogenase such as one having an amino acid sequence at least 60, 70, 80, 90, or 95% identical to the amino acid sequence of SEQ ID NO: 4, 8, 14, 18 or 22 comprises the amino acid sequence of "CYPS(L/M)" (SEQ ID NO: 28).

The above-described positions of amino acid substitution mutation are positions in SEQ ID NO:4. However, the amino acid sequence of the electron transfer subunit to which the mutation is to be introduced may have a length different from the length of SEQ ID NO:4. For example, in cases where the amino acid sequence of the electron transfer subunit to which the mutation is to be introduced is shorter by five amino acids in the N-terminal side compared to SEQ ID NO:4, the threonine residue at position 336 of SEQ ID NO:4 corresponds to the threonine at position 331 of the amino acid sequence. Such a case is also regarded as substitution of the threonine residue corresponding to the "threonine residue at position 336", and included in a mode of the present invention. The same applies to other residues.

The electron transfer subunit may also comprise another mutation in addition to the mutation that introduces cysteine.

The electron transfer subunit contains three heme-binding domains. The electron transfer subunit may be a mutant (truncated) electron transfer subunit in which the first heme-binding domain and the second heme-binding domain, that is, the first and second domains as counted from the N-terminal side, respectively, are deleted. Such a mutant electron transfer subunit is disclosed in US 2019-0010215.

Thus, in the electron transfer subunit having three heme-binding domains (CXXCH (SEQ ID NO: 31) motifs), the first and second heme-binding domains as counted from the N-terminal side, or a region(s) including these, may be deleted. The following description uses the electron transfer subunit of *Burkholderia cepacia* as a representative example. In SEQ ID NO:4, there are the first heme-binding domain (amino acid positions 43 to 47), second heme-binding domain (amino acid positions 191 to 195), and third heme-binding domain (amino acid positions 334 to 338). Among these, the first heme-binding domain and second heme-binding domain may be deleted, or the region including the first and second heme-binding domains (amino acid positions 43 to 195) may be deleted.

Examples of a mutant electron transfer subunit in which the region including the first and second heme-binding domains is deleted include a mutant electron transfer subunit composed of amino acid positions 314 to 425 or 330 to 425 of SEQ ID NO:4.

GDH is known also in other microorganisms. In the amino acid sequence of their electron transfer subunit, for example, in an amino acid sequence having an identity of at least 60%, at least 80%, at least 90%, or at least 95% to SEQ ID NO:4 or to the truncated sequence composed of amino acid positions 314 to 425 or 330 to 425 of SEQ ID NO:4, cysteine may be introduced to a position corresponding to such an amino acid residue as the threonine residue at position 336, glycine residue at position 385, aspartic acid residue at position 383, or tyrosine residue at position 391, and/or the threonine residue at position 345, proline residue at position 346, or tyrosine residue at position 349.

Specifically, the amino acid sequence of the electron transfer subunit to which the mutation is to be introduced may be aligned with the amino acid sequence of SEQ ID NO:4, and the amino acid whose position corresponds to the position of the threonine residue at position 336, glycine residue at position 385 aspartic acid residue at position 383, or tyrosine residue at position 391; or the threonine residue at position 345, proline residue at position 346, or tyrosine residue at position 349; of SEQ ID NO:4 may be substituted with cysteine.

Any polypeptide having some degree of a sequence identity to SEQ ID NO:4 or the other sequence of the electron transfer subunit described below can be used to prepare an electron transfer subunit of the mutant glucose dehydrogenase as long as it maintains the function of the electron transfer subunit, i.e. forming a complex with the catalytic subunit and the hitchhiker subunit and receiving and transferring an electron. An amino acid sequence of an electron transfer subunit preferably maintains three heme-binding domains or in the case of a truncated form, the third three heme-binding domain.

Examples of the amino acid sequence of the GDH electron transfer subunit having an identity of at least 60% to SEQ ID NO:4 include the sequence of the electron transfer subunit of each of the following: *Burkholderia cenocepacia* J2315 strain (WP_006482958), *Burkholderia thailandensis* TXDOH strain (WP_009900297), *Ralstonia pickettii* 12D strain (WP_012761509), *Ralstonia solanacearum* IPO1609 strain (WP_049281214), *Burkholderia phytofirmans* PsJN strain (WP_012428609), *Ralstonia* sp. (WP_048931829), *Moraxellaceae bacterium* (WP_114899536), *Pseudomonas knackmussii* (WP_043248520), *Yersinia nurmii* (WP_049596851), *Edaphovirga cremea* (WP_114193338), *Silvimonas terrae* (WP_184102397), *Zymobacter palmae* (WP_211245188), *Cobetia* sp. (WP_158773850), *Halomonas* sp. (WP_107336529) and *Ewingella americana* (WP_034788317).

As described above, the region and residues to which the cysteine residue is introduced in these electron transfer subunits can be determined by aligning the sequence of each electron transfer subunit with that of *B. cepacia* (SEQ ID NO: 4).

Figure 11:
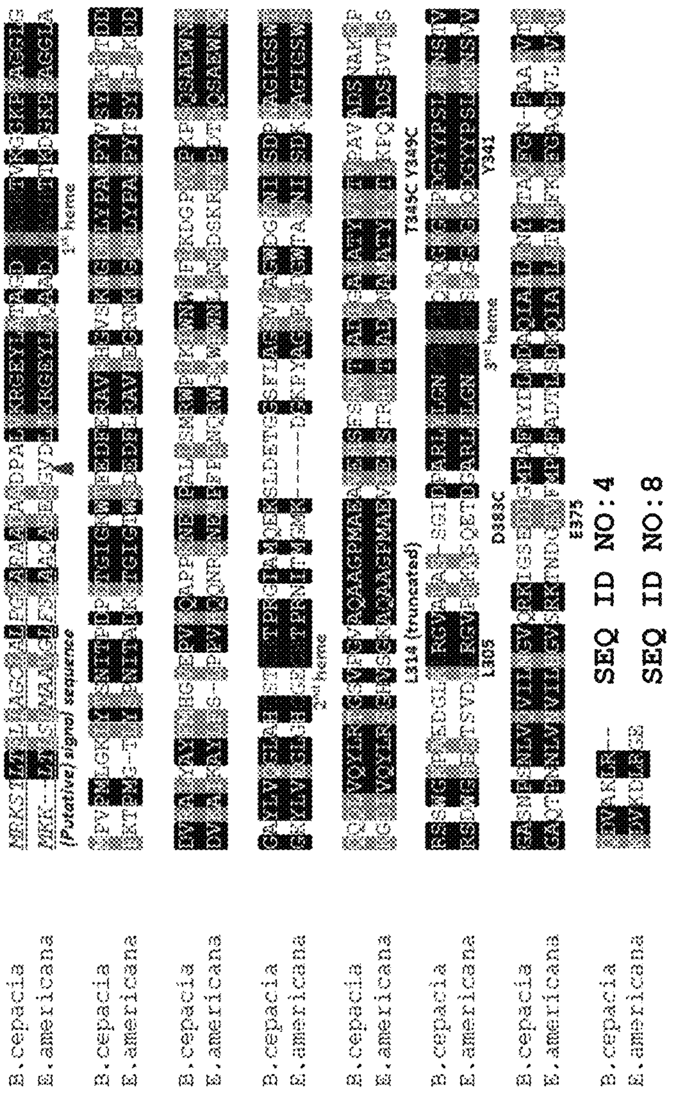
FIG. 11 shows the sequence alignment of the electron transfer subunit between *Burkholderia cepacia* and *Ewingella americana*.

For example, in the case of the electron transfer subunit of *E. americana* (SEQ ID NO: 8), as shown in FIG. 11, the region 330 to 400 in SEQ ID NO: 4 is located in the region 322-392 of in SEQ ID NO: 8, and the threonine residue at position 336, aspartic acid residue at position 383, glycine residue at position 385 and tyrosine residue at position 391 respectively correspond to serine residue at position 328, glutamic acid residue at position 375, phenylalanine residue at position 377, and aspartic acid residue at position 383 in SEQ ID NO: 8.

Furthermore, in the case of the electron transfer subunit of *E. americana* (SEQ ID NO: 8), as shown in FIG. 11, the region 341 to 350 in SEQ ID NO: 4 is located in the region 333-342 of in SEQ ID NO: 8, and the threonine residue at position 345, proline residue at position 346, and tyrosine residue at position 349 respectively correspond to serine residue at position 337, glutamine residue at position 338, and tyrosine residue at position 341 in SEQ ID NO: 8.

In SEQ ID NO: 8, there are the first heme-binding domain (amino acid positions 41 to 45), second heme-binding domain (amino acid positions 187 to 191), and third heme-binding domain (amino acid positions 326 to 330). Among these, the first heme-binding domain and second heme-binding domain may be deleted, or the region including the first and second heme-binding domains (amino acid positions 41 to 191) may be deleted. Examples of a mutant electron transfer subunit in which the region including the first and second heme-binding domains is deleted include a mutant electron transfer subunit composed of amino acid positions 306 to 420 or 322 to 420 of SEQ ID NO: 8.

Another embodiment of the electron transfer subunit includes an electron transfer subunit comprising an amino acid sequence having at least 60%, 80%, 90% or 95% identity to SEQ ID NO: 8 or amino acids 306 to 420 of SEQ ID NO: 8 wherein a first cysteine is introduced at the position corresponding to the serine residue at position 328, glutamic acid residue at position 375, phenylalanine residue at position 377, or aspartic acid residue at position 383, and/or a second cysteine is introduced at the position corresponding to the serine residue at position 337, glutamine residue at position 338, and tyrosine residue at position 341 in SEQ ID NO: 8.

Figure 19:
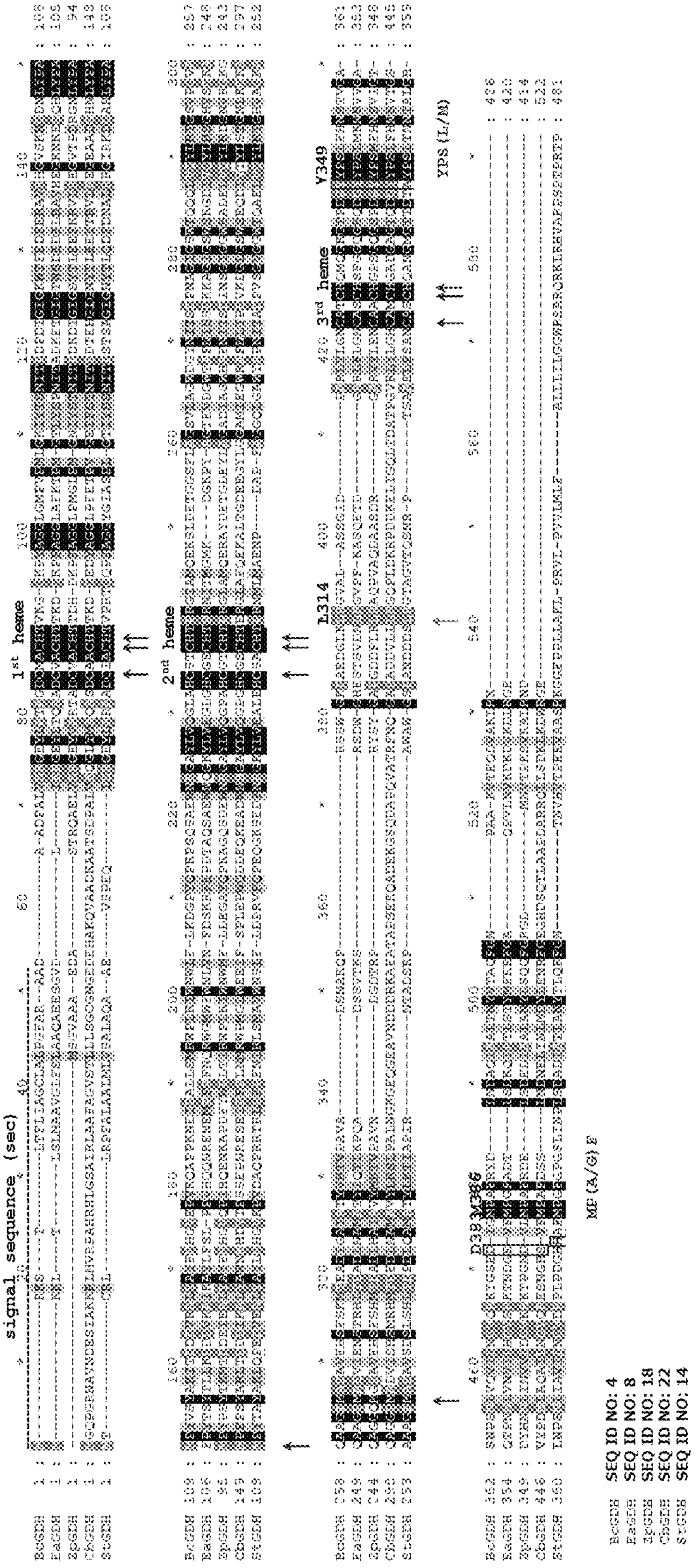
FIG. 19 shows the sequence alignment of the electron transfer subunit subunit between *Burkholderia cepacia, Ewingella americana, Silvimonas terrae, Zymobacter palmae* and *Cobetia* sp.

Furthermore, in the case of the electron transfer subunit of *Silvimonas terrae* (SEQ ID NO: 14), as shown in FIG. 19, the aspartic acid residue at position 383 in SEQ ID NO: 4 corresponds to histidine residue at position 382 in SEQ ID NO: 14. The tyrosine residue at position 349 in SEQ ID NO: 4 corresponds to alanine residue at position 347 in SEQ ID NO: 14.

In SEQ ID NO: 14, there are the first heme-binding domain (amino acid positions 43 to 47), second heme-binding domain (amino acid positions 191 to 195), and third heme-binding domain (amino acid positions 332 to 336). Among these, the first heme-binding domain and second heme-binding domain may be deleted, or the region including the first and second heme-binding domains (amino acid positions 43 to 195) may be deleted. Examples of a mutant electron transfer subunit in which the region including the first and second heme-binding domains is deleted include a mutant electron transfer subunit composed of amino acid positions 332 to 481 of SEQ ID NO: 14.

Another embodiment of the electron transfer subunit includes an electron transfer subunit comprising an amino acid sequence having at least 60%, 80%, 90% or 95% identity to SEQ ID NO: 14 or amino acids 332 to 481 of SEQ ID NO: 14 wherein a first cysteine is introduced at the position corresponding to the histidine residue at position 382 in SEQ ID NO: 14 and/or a second cysteine is introduced at the position corresponding to the alanine residue at position 347 in SEQ ID NO: 14.

Furthermore, in the case of the electron transfer subunit of *Zymobacter palmae* (SEQ ID NO: 18), as shown in FIG. 19, the aspartic acid residue at position 383 in SEQ ID NO: 4 corresponds to aspartic acid residue at position 389 in SEQ ID NO: 18. The tyrosine residue at position 349 in SEQ ID NO: 4 corresponds to tyrosine residue at position 355 in SEQ ID NO: 18.

In SEQ ID NO: 18, there are the first heme-binding domain (amino acid positions 49 to 53), second heme-binding domain (amino acid positions 196 to 200), and third heme-binding domain (amino acid positions 340 to 344). Among these, the first heme-binding domain and second heme-binding domain may be deleted, or the region including the first and second heme-binding domains (amino acid positions 49 to 200) may be deleted. Examples of a mutant electron transfer subunit in which the region including the first and second heme-binding domains is deleted include a mutant electron transfer subunit composed of amino acid positions 340 to 433 of SEQ ID NO: 18.

Another embodiment of the electron transfer subunit includes an electron transfer subunit comprising an amino acid sequence having at least 60%, 80%, 90% or 95% identity to SEQ ID NO: 18 or amino acids 340 to 433 of SEQ ID NO: 18 wherein a first cysteine is introduced at the position corresponding to the aspartic acid residue at position 389 in SEQ ID NO: 18 and/or a second cysteine is introduced at the position corresponding to the tyrosine residue at position 355 in SEQ ID NO: 18.

Furthermore, in the case of the electron transfer subunit of *Cobetia* sp. (SEQ ID NO: 22), as shown in FIG. 19, the aspartic acid residue at position 383 in SEQ ID NO: 4 corresponds to serine residue at position 467 in SEQ ID NO: 22. The tyrosine residue at position 349 in SEQ ID NO: 4 corresponds to tyrosine residue at position 433 in SEQ ID NO: 22.

In SEQ ID NO: 22, there are the first heme-binding domain (amino acid positions 84 to 88), second heme-binding domain (amino acid positions 231 to 235), and third heme-binding domain (amino acid positions 418 to 422). Among these, the first heme-binding domain and second heme-binding domain may be deleted, or the region including the first and second heme-binding domains (amino acid positions 84 to 235) may be deleted. Examples of a mutant electron transfer subunit in which the region including the first and second heme-binding domains is deleted include a mutant electron transfer subunit composed of amino acid positions 418 to 522 of SEQ ID NO: 22.

Another embodiment of the electron transfer subunit includes an electron transfer subunit comprising an amino acid sequence having at least 60%, 80%, 90% or 95% identity to SEQ ID NO: 22 or amino acids 418 to 522 of SEQ ID NO: 22 wherein a first cysteine is introduced at the position corresponding to the seine residue at position 467 in SEQ ID NO: 22 and/or a second cysteine is introduced at the position corresponding to the tyrosine residue at position 433 in SEQ ID NO: 22.

<Hitchhiker Subunit>

The glucose dehydrogenase also includes a hitchhiker subunit. The hitchhiker subunit is also called γ subunit, and has a function of forming a complex with the α subunit and β subunit, and being secreted into periplasm. The hitchhiker subunit is not limited as long as it has the function. γ subunits derived from various organisms, including known γ subunits, may be used. The hitchhiker subunit may be derived from the same microorganism as the microorganism from which the catalytic subunit or electron transfer subunit is derived. Examples of the hitchhiker subunit include the hitchhiker subunit of GDH of *Burkholderia cepacia.*

SEQ ID NO:2 is an amino acid sequence of the GDH hitchhiker subunit of the *Burkholderia cepacia* KS1 strain. The following description is given with reference to this sequence.

As described above, the hitchhiker subunit may contain a cysteine residue introduced therein for formation of a disulfide bond with the electron transfer subunit.

The cysteine introduction site in the amino acid sequence of the hitchhiker subunit is preferably in a region forming the interface with the electron transfer subunit. For example, cysteine is introduced to a position in the region of amino acid positions 140 to 160 in the amino acid sequence of SEQ ID NO:2. Thus, an amino acid residue in the region of amino acid positions 140 to 160 of SEQ ID NO:2 is substituted with cysteine. This region in the hitchhiker subunit is a region located on the interface with the electron transfer subunit in the spatial structure of GDH.

Specific examples of the amino acid in this region include the threonine residue at position 145, asparagine residue at position 154, and lysine residue at position 155 in the amino acid sequence of SEQ ID NO:2. Introduction of cysteine residue includes substitution by cysteine and insertion of cysteine. For example, any of the above-described amino acid residues may be substituted with a cysteine residue. Alternatively, when a cysteine residue is inserted, the cysteine residue may be inserted at a position immediately before or immediately after these residues.

Among the above-described residues, the lysine residue at position 155 is preferably substituted by a cysteine residue. This amino acid residue exists at a position one amino acid before the amino acid motif "PXXWXXXP" (SEQ ID NO: 29). In one embodiment, a cysteine residue is introduced to substitute the amino acid residue one amino acid before this motif, and thereby the hitchhiker subunit of the mutant glucose dehydrogenase such as one having an amino acid sequence at least 60, 70, 80, 90, or 95% identical to the amino acid sequence of SEQ ID NO:2, 6, 12, 16 or 20 comprises the amino acid sequence of "CPXXWXXXP" (SEQ ID NO: 30).

The above-described positions of amino acid substitution mutation are positions in SEQ ID NO:2. However, the amino acid sequence of the hitchhiker subunit to which the mutation is to be introduced may have a length different from the length of SEQ ID NO:2. For example, in cases where the amino acid sequence of the hitchhiker subunit to which the mutation is to be introduced is longer by two amino acids in the N-terminal side compared to SEQ ID NO:2, the threonine residue at position 145 of SEQ ID NO:2 corresponds to the threonine at position 147 of the amino acid sequence. Such a case is also regarded as substitution of the threonine residue corresponding to the "threonine residue at position 145", and included in a mode of the present invention. The same applies to other residues.

Examples of a preferred combination of the cysteine introduction site for disulfide formation with the hitchhiker subunit in the electron transfer subunit (the region of amino acid positions 341 to 350 of SEQ ID NO:4) and the cysteine introduction site in the hitchhiker subunit (the region of amino acid positions 140 to 160 of SEQ ID NO:2) include the combination of the threonine at position 345 of the electron transfer subunit and the asparagine at position 154 of the hitchhiker subunit, and the combination of the tyrosine at position 349 of the electron transfer subunit and the lysine at position 155 of the hitchhiker subunit. These combinations of residues are combinations of residues having a distance of about 5 Å from each other in the spatial structure of FAD-GDH, and capable of more efficient formation of a disulfide bond.

The hitchhiker subunit may also comprise another mutation in addition to the mutation that introduces cysteine.

GDH is known also in other microorganisms. In the amino acid sequence of their hitchhiker subunit, for example, in an amino acid sequence having an identity of at least 60%, at least 80%, at least 90%, or at least 95% to SEQ ID NO:2, cysteine may be introduced into the region described above, or to the position of the amino acid residue corresponding to the specific amino acid residue described above.

Specifically, the amino acid sequence of the hitchhiker subunit to which the mutation is to be introduced may be aligned with the amino acid sequence of SEQ ID NO:2, and the amino acid whose position corresponds to the position of the threonine residue at position 145, asparagine residue at position 154, or lysine residue at position 155 of SEQ ID NO:2 may be substituted with cysteine.

Any polypeptide having some degree of a sequence identity to SEQ ID NO:2 or the other sequence of the hitchhiker subunit described below can be used to prepare a hitchhiker subunit of the mutant glucose dehydrogenase as long as it maintains the function of the hitchhiker subunit, i.e. forming a complex with the catalytic subunit and the electron transfer subunit and being secreted into periplasm.

Examples of the amino acid sequence of the GDH hitchhiker subunit having an identity of at least 60% to SEQ ID NO:2 include the sequence of the γ subunit of each of the following: *Burkholderia cenocepacia* J2315 strain (WP_006482974), *Burkholderia thailandensis* TXDOH strain (WP_009900299), *Ralstonia pickettii* 12D strain (WP_012761507), *Ralstonia solanacearum* IPO1609 strain (WP_003265142), *Burkholderia phytofirmans* PsJN strain (WP_012428611), *Ralstonia* sp. (WP_048931990), *Moraxellaceae bacterium* (WP_114899538), *Pseudomonas knackmussii* (WP_043248523), *Yersinia nurmii* (WP_049596849), *Edaphovirga cremea* (WP_114193340), *Silvimonas terrae* (WP_184102399), *Zymobacter palmae* (BBG29837), *Cobetia* sp. (WP_158773852), *Halomonas* sp. (WP_107334715) and *Ewingella americana* (WP_034788279).

As described above, the region and residues to which the cysteine residue is introduced in these hitchhiker subunits can be determined by aligning the sequence of each hitchhiker subunit with that of *B. cepacia* (SEQ ID NO: 2).

Figure 9:
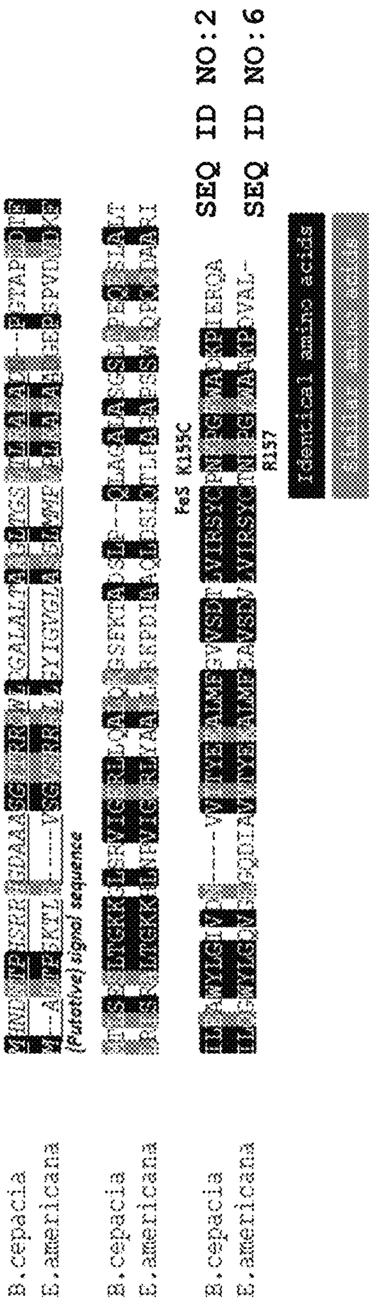
FIG. 9 shows the sequence alignment of the hitchhiker subunit between *Burkholderia cepacia* and *Ewingella americana*.

For example, in the case of the hitchhiker subunit of *E. americana* (SEQ ID NO: 6), as shown in FIG. 9, the region 140 to 160 in SEQ ID NO: 2 is located in the region 142-162 of in SEQ ID NO: 6, and the threonine residue at position 145, asparagine residue at position 154, and lysine residue at position 155 respectively correspond to valine residue at position 147, asparagine residue at position 156, and arginine residue at position 157 in SEQ ID NO: 6.

Another embodiment of the hitchhiker subunit includes a hitchhiker subunit comprising an amino acid sequence having at least 60%, 80%, 90% or 95% identity to SEQ ID NO: 6 wherein cysteine is introduced at the position corresponding to the valine residue at position 147, asparagine residue at position 156, or arginine residue at position 157 in SEQ ID NO: 6.

Figure 20:
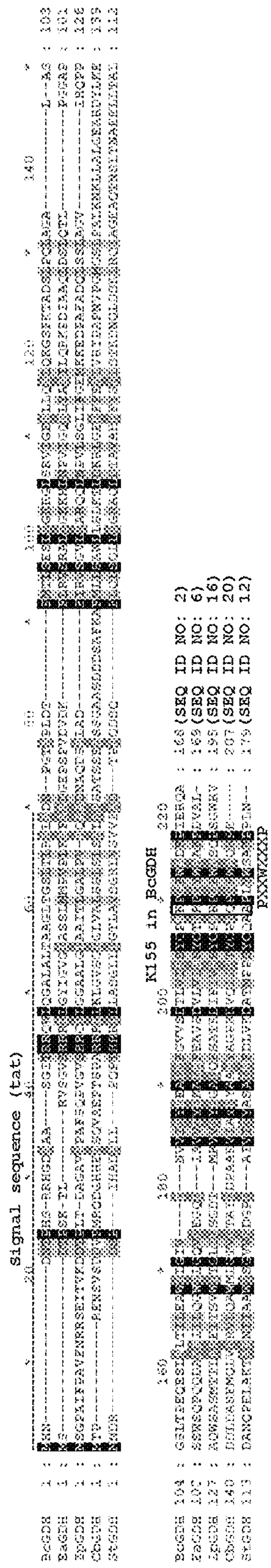
FIG. 20 shows the sequence alignment of the hitchhiker between *Burkholderia cepacia, Ewingella americana, Silvimonas terrae, Zymobacter palmae*, and *Cobetia* sp.

For example, in the case of the hitchhiker subunit of *Silvimonas terrae* (SEQ ID NO: 12), as shown in FIG. 20, the lysine residue at position 155 corresponds to the alanine residue at position 168 in SEQ ID NO: 12.

Another embodiment of the hitchhiker subunit includes a hitchhiker subunit comprising an amino acid sequence having at least 60%, 80%, 90% or 95% identity to SEQ ID NO: 12 wherein cysteine is introduced at the position corresponding to the alanine residue at position 168 in SEQ ID NO: 12.

For example, in the case of the hitchhiker subunit of *Zymobacter palmae* (SEQ ID NO: 16), as shown in FIG. 20, the lysine residue at position 155 corresponds to the arginine residue at position 182 in SEQ ID NO: 16.

Another embodiment of the hitchhiker subunit includes a hitchhiker subunit comprising an amino acid sequence having at least 60%, 80%, 90% or 95% identity to SEQ ID NO: 16 or amino acids 19 to 195 of SEQ ID NO: 16 wherein cysteine is introduced at the position corresponding to the arginine residue at position 182 in SEQ ID NO: 16.

For example, in the case of the hitchhiker subunit of *Cobetia* sp. (SEQ ID NO: 20), as shown in FIG. 20, the lysine residue at position 155 corresponds to the glutamine residue at position 198 in SEQ ID NO: 20.

Another embodiment of the hitchhiker subunit includes a hitchhiker subunit comprising an amino acid sequence having at least 60%, 80%, 90% or 95% identity to SEQ ID NO: 20 or amino acids 14 to 207 of SEQ ID NO: 20 wherein cysteine is introduced at the position corresponding to the glutamine residue at position 198 in SEQ ID NO: 20.

In one embodiment of a mutant FAD-dependent glucose dehydrogenase,

- the catalytic subunit comprises an amino acid sequence having at least 60%, 70%, 80%, 90% or 95% identity to SEQ ID NO: 3 wherein cysteine is introduced at the position corresponding to the proline residue at position 205 in SEQ ID NO: 3,
- the electron transfer subunit comprises an amino acid sequence having at least 60%, 70%, 80%, 90% or 95% identity to SEQ ID NO: 4 or amino acids 330 to 425 of SEQ ID NO: 4 wherein a first cysteine is introduced at the position corresponding to the aspartic acid residue at position 383 in SEQ ID NO: 4 and a second cysteine is introduced at the position corresponding to the threonine residue at position 345 in SEQ ID NO: 4, and
- the hitchhiker subunit comprises an amino acid sequence having at least 60%, 70%, 80%, 90% or 95% identity to SEQ ID NO: 2 wherein cysteine is introduced at the position corresponding to the asparagine residue at position 154 in SEQ ID NO: 2.

In one embodiment of a mutant FAD-dependent glucose dehydrogenase,

- the catalytic subunit comprises an amino acid sequence having at least 60%, 70%, 80%, 90% or 95% identity to SEQ ID NO: 3 wherein cysteine is introduced at the position corresponding to the proline residue at position 205 in SEQ ID NO: 3,
- the electron transfer subunit comprises an amino acid sequence having at least 60%, 70%, 80%, 90% or 95% identity to SEQ ID NO: 4 or amino acids 330 to 425 of SEQ ID NO: 4 wherein a first cysteine is introduced at the position corresponding to the aspartic acid residue at position 383 in SEQ ID NO: 4 and a second cysteine is introduced at the position corresponding to the tyrosine residue at position 349 in SEQ ID NO: 4, and the hitchhiker subunit comprises an amino acid sequence having at least 60%, 70%, 80%, 90% or 95% identity to SEQ ID NO: 2 wherein cysteine is introduced at the position corresponding to the lysine residue at position 155 in SEQ ID NO: 2.

In one embodiment of a mutant FAD-dependent glucose dehydrogenase, the catalytic subunit comprises an amino acid sequence having at least 60%, 70%, 80%, 90% or 95% identity to SEQ ID NO: 7 wherein cysteine is introduced at the position corresponding to the proline residue at position 202 in SEQ ID NO: 7, the electron transfer subunit comprises an amino acid sequence having at least 60%, 70%, 80%, 90% or 95% identity to SEQ ID NO: 8 or amino acids 326 to 420 of SEQ ID NO: 8 wherein a first cysteine is introduced at the position corresponding to the glutamic acid residue at position 375 in SEQ ID NO: 8 and a second cysteine is introduced at the position corresponding to the tyrosine residue at position 341 in SEQ ID NO: 8, and the hitchhiker subunit comprises an amino acid sequence having at least 60%, 70%, 80%, 90% or 95% identity to SEQ ID NO: 6 wherein cysteine is introduced at the position corresponding to the arginine residue at position 157 in SEQ ID NO: 6.

In one embodiment of a mutant FAD-dependent glucose dehydrogenase, the catalytic subunit comprises an amino acid sequence having at least 60%, 70%, 80%, 90% or 95% identity to SEQ ID NO: 13 wherein cysteine is introduced at the position corresponding to the proline residue at position 204 in SEQ ID NO: 13, the electron transfer subunit comprises an amino acid sequence having at least 60%, 70%, 80%, 90% or 95% identity to SEQ ID NO: 14 or amino acids 332 to 481 of SEQ ID NO: 14 wherein a first cysteine is introduced at the position corresponding to the histidine residue at position 382 in SEQ ID NO: 14 and a second cysteine is introduced at the position corresponding to the alanine residue at position 347 in SEQ ID NO: 14, and the hitchhiker subunit comprises an amino acid sequence having at least 60%, 70%, 80%, 90% or 95% identity to SEQ ID NO: 12 wherein cysteine is introduced at the position corresponding to the alanine residue at position 168 in SEQ ID NO: 12.

In one embodiment of a mutant FAD-dependent glucose dehydrogenase, the catalytic subunit comprises an amino acid sequence having at least 60%, 70%, 80%, 90% or 95% identity to SEQ ID NO: 17 wherein cysteine is introduced at the position corresponding to the proline residue at position 200 in SEQ ID NO: 17, the electron transfer subunit comprises an amino acid sequence having at least 60%, 70%, 80%, 90% or 95% identity to SEQ ID NO: 18 or amino acids 340 to 465 of SEQ ID NO: 18 wherein a first cysteine is introduced at the position corresponding to the aspartic acid residue at position 389 in SEQ ID NO: 18 and a second cysteine is introduced at the position corresponding to the tyrosine residue at position 355 in SEQ ID NO: 18, and the hitchhiker subunit comprises an amino acid sequence having at least 60%, 70%, 80%, 90% or 95% identity to SEQ ID NO: 16 or amino acids 19 to 195 of SEQ ID NO: 16 wherein cysteine is introduced at the position corresponding to the arginine residue at position 182 in SEQ ID NO: 16.

In one embodiment of a mutant FAD-dependent glucose dehydrogenase, the catalytic subunit comprises an amino acid sequence having at least 60%, 70%, 80%, 90% or 95% identity to SEQ ID NO: 21 wherein cysteine is introduced at the position corresponding to the proline residue at position 204 in SEQ ID NO: 21, the electron transfer subunit comprises an amino acid sequence having at least 60%, 70%, 80%, 90% or 95% identity to SEQ ID NO: 22 or amino acids 418 to 522 of SEQ ID NO: 22 wherein a first cysteine is introduced at the position corresponding to the serine residue at position 467 in SEQ ID NO: 22 and a second cysteine is introduced at the position corresponding to the tyrosine residue at position 433 in SEQ ID NO: 22, and the hitchhiker subunit comprises an amino acid sequence having at least 60%, 70%, 80%, 90% or 95% identity to SEQ ID NO: 20 or amino acids 14 to 207 of SEQ ID NO: 20 wherein cysteine is introduced at the position corresponding to the glutamine residue at position 198 in SEQ ID NO: 20.

The mutant GDH according to one embodiment of the present invention can be obtained by genetic engineering. More specifically, the mutant GDH can be obtained by introducing the mutations of interest by site-directed mutagenesis or the like to the gene encoding GDH, and expressing the resulting mutant GDH gene in an arbitrary host cell or cell-free translation system.

The gene encoding the GDH catalytic (a) subunit is not limited as long as it has a nucleotide sequence corresponding to the amino acid sequence of the GDH α subunit. Specific examples of the gene include a DNA composed of nucleotide positions 764 to 2380 of SEQ ID NO:1. The α-subunit gene may be a DNA having the nucleotide sequence composed of nucleotide positions 764 to 2380 of the nucleotide sequence of SEQ ID NO:1, or a DNA which hybridizes, under stringent conditions, with a probe that can be prepared from this sequence, which DNA encodes a protein having the GDH activity.

Specific examples of the gene encoding the GDH electron transfer (β) subunit include a DNA containing the nucleotide sequence composed of nucleotide positions 2386 to 3660 of SEQ ID NO: 1. The β-subunit gene may be a DNA having the nucleotide sequence composed of nucleotide positions 2386 to 3660 of SEQ ID NO: 1, or a DNA which hybridizes, under stringent conditions, with a probe that can be prepared from this sequence, which DNA encodes a protein capable of functioning as the β subunit.

Specific examples of the gene encoding the GDH hitchhiker subunit (γ) subunit include a DNA containing the nucleotide sequence composed of nucleotide positions 258 to 761 of SEQ ID NO:1. The α-subunit gene may be a DNA having the nucleotide sequence composed of nucleotide positions 258 to 761 of SEQ ID NO:1, or a DNA which hybridizes, under stringent conditions, with a probe that can be prepared from this sequence, which DNA encodes a protein capable of functioning as the γ subunit.

Examples of the stringent conditions described above include conditions that allow hybridization of DNAs having an identity of preferably at least 80%, more preferably at least 90%, especially preferably at least 95%, with each other and does not allow hybridization of DNAs having an identity of less than 80%, less than 90% or less than 95%.

Specific examples of the stringent conditions include those in which washing is carried out with 0.1×SSC and 0.1% SDS at 60° C., 65° C., or 68° C.

The α-subunit gene, β-subunit gene, and γ-subunit gene can be obtained by, for example, PCR using chromosomal DNA of the *Burkholderia cepacia* KS1 strain as a template. The PCR primers therefor can be prepared by chemical synthesis based on the above-described nucleotide sequences. Alternatively, the genes can be obtained from chromosomal DNA of the *Burkholderia cepacia* KS1 strain by hybridization using, as probes, oligonucleotides prepared based on the above-described sequences. Strains other than the KS1 strain, such as the *Burkholderia cenocepacia* J2315 strain, *Burkholderia thailandensis* TXDOH strain, *Ralstonia pickettii* 12D strain, *Ralstonia solanacearum* IPO1609 strain, and *Burkholderia phytofirmans* PsJN strain, may also be used.

Each of the GDH α-subunit, β-subunit, and γ-subunit having a desired mutation(s) can be obtained by introducing a nucleotide mutation(s) corresponding to the desired amino acid mutation(s) (such as the substitution with a cysteine residue) to a DNA encoding the GDH subunit by site-directed mutagenesis, and expressing the resulting mutant DNA using an appropriate expression system. Further, by allowing expression from the DNA encoding the mutant GDH α subunit, and also from the DNA encoding the mutant β subunit and the DNA encoding the mutant γ subunit, a mutant GDH can be obtained. The introduction of the mutation(s) to the DNA encoding each subunit may be carried out using a polycistronic DNA fragment encoding the γ subunit, α subunit, and β subunit in this order.

The polycistronic DNA fragment encoding the γ subunit, α subunit, and β subunit in this order can be obtained by, for example, PCR using chromosomal DNA of the *Burkholderia cepacia* KS1 strain as a template, and oligonucleotides having the nucleotide sequences of SEQ ID NOs:9 and 10 as primers.

The vector used for obtaining the genes of the GDH subunits, introducing the mutations, expressing the genes, and the like include vectors capable of functioning in bacteria belonging to the genus *Escherichia*, such as pTrc99A, pBR322, pUC18, pUC118, pUC19, pUC119, pACYC184, and pBBR122. Examples of the promoter to be used for the gene expression include lac, trp, tac, trc, PL, tet, and PhoA. By introducing the γ subunit gene, α subunit gene, and β subunit gene to an appropriate site in an expression vector containing a promoter, insertion of the genes into the vector and linking of the promoter can be carried out in the same single process. Examples of such an expression vector include pTrc99A, pBluescript, and pKK223-3.

The γ subunit gene, α subunit gene, and β subunit gene may be incorporated in the chromosomal DNA of the host microorganism in a form which allows the expression. Examples of the method of transformation of the microorganism with the recombinant vector include the competent cell method by calcium treatment, the protoplast method, and the electroporation method.

Examples of the host microorganism include, but are not limited to, bacteria belonging to the genus *Bacillus* such as *Bacillus subtilis*; yeasts such as *Saccharomyces cerevisiae*; and filamentous fungi such as *Aspergillus niger*. Any host microorganism suitable for production of a foreign protein may be used.

The transformant such as a microorganism transformed with the mutant GDH genes may be cultured by an appropriate culture method depending on the type of the transformant. Examples of the conditions for the culture include culturing at 30 to 37° C. for 12 to 24 hours.

The mutant GDH may be used also after purification. The mutant GDH may contain an additional sequence such as a tag sequence for purification.

The mutant GDH according to one embodiment of the present invention, or the microorganism which expresses the mutant GDH, may be used as a component of an enzyme electrode of a glucose sensor. Specific examples of the glucose sensor include glucose sensors that use, as a working electrode, an enzyme electrode formed by immobilization of the mutant GDH on a surface of an electrode such as a gold electrode, platinum electrode, or carbon electrode. The sensor means a measurement system for electrochemically measuring the concentration of a test substance of interest, and usually contains three electrodes, which are a working electrode (enzyme electrode), counter electrode (platinum or the like), and reference electrode (Ag/AgCl or the like). The sensor may also be a two-electrode system constituted by a working electrode and a counter electrode, such as those used in conventional, simple blood glucose level systems. The sensor preferably further contains: a constant-temperature cell in which a buffer and a test sample are to be placed; a power source for applying a voltage to the working electrode; an ammeter; a recorder; and/or the like. The sensor may be either a batch-type sensor or flow-type sensor. In particular, the flow-type sensor may be a sensor capable of continuous measurement of the blood glucose level. More specifically, the sensor may be a sensor having a two-electrode system or three-electrode system on which the enzyme of the present invention is immobilized, which electrode system is inserted into a blood sample or dialysis sample that is continuously supplied, or into blood or interstitial fluid, to perform the measurement. The structure of such an enzyme sensor is well known in the art, and described in, for example, Biosensors—Fundamental and Applications—Anthony P F. Turner, Isao Karube and George S. Wilson, Oxford University Press 1987.

The sensor according to one mode of the present invention may be a direct electron transfer-type sensor containing no electron-transfer mediator.

The method of immobilizing the enzyme (mutant GDH) on the electrode is not limited. Examples of the method include a method in which enzyme molecules are chemically immobilized on the electrode using a cross-linking agent or the like, a method in which enzyme molecules are indirectly immobilized on the electrode using a binder or the like, and a method by physical adsorption of enzyme molecules to the electrode.

The method in which the enzyme is chemically immobilized on the electrode using a cross-linking agent or the like may be a method in which the enzyme is directly immobilized on the electrode. Alternatively, a method such as the one disclosed in U.S. Ser. No. 10/563,242B2 may be used. More specifically, this method is a method in which a monolayer (SAM)-forming molecule is immobilized on the electrode, and a molecular recognition element containing the enzyme is immobilized through the SAM-forming molecule.

The monolayer-forming molecule is a compound capable of binding to the electrode, and of allowing binding of the enzyme molecule thereto. By binding a plurality of molecules of the compound in the same direction on the electrode surface, a monolayer film can be formed. By using the monolayer-forming molecule, the distance between the electrode and the enzyme molecule can be controlled.

The monolayer-forming molecule preferably contains: a first functional group having affinity to the electrode, a spacer region, and a second functional group reactive with a functional group contained in the enzyme molecule. More preferably, the monolayer-forming molecule has a structure in which the first functional group having affinity to the electrode is bound to a first end of the spacer region, and in which the second functional group reactive with a functional group contained in the enzyme molecule is bound to a second end of the spacer region. Here, examples of the first functional group having affinity to the electrode include a thiol group and dithiol group in cases where the electrode is a metal; and pyrene and porphyrin in cases where the electrode is carbon. On the other hand, examples of the second functional group reactive with a functional group contained in the enzyme molecule include a succinimide group in cases of reaction with an amino group (including a terminal amino group and side-chain amino group) contained in the enzyme molecule; and an oxazoline group in cases of reaction with a carboxyl group (including a terminal carboxyl group and side-chain carboxyl group) contained in the enzyme molecule. Examples of a monolayer-forming molecule containing a thiol group or dithiol group, and succinimide group, include DSH as described later in Examples.

The measurement of the glucose concentration using the glucose sensor of the present invention can be carried out as follows. A buffer is placed in a constant-temperature cell of the sensor, and the temperature of the cell is kept constant. As a working electrode, an enzyme electrode on which the mutant GDH is immobilized is used. As a counter electrode, for example, a platinum electrode is used. As a reference electrode, for example, an Ag/AgCl electrode is used. A constant voltage is applied to the working electrode. After the electric current becomes constant, a sample containing glucose is placed in the constant-temperature cell, and the increase in the electric current is measured. According to a calibration curve prepared using glucose solutions having standard concentrations, the glucose concentration in the sample can be calculated.

The mutant GDH according to one embodiment of the present invention can also be used as a component of a glucose assay kit. The glucose assay kit may contain a coloring or luminescence reagent, a dilution buffer, a standard substance, manufacturer's instructions, and/or the like in addition to the mutant GDH.

For example, a glucose sensor and a glucose assay kit using a wild-type GDH of *Burkholderia cepacia* are described in US 2004/0023330 A1. The mutant GDH can be applied in the similarly manner.

EXAMPLES

The present invention is described below more specifically by showing non-limiting Examples.

Example 1

Expression of Mutant GDH

As a GDH comprising a cytochrome C-containing subunit, a CyGDH derived from *B. cepacia* was used. The CyGDH derived from *B. cepacia* is an oligomer enzyme composed of the γ, a, and β subunits. These three subunits are encoded in the gene having the nucleotide sequence of SEQ ID NO:1. Based on this sequence, pTrc99Aγα(QYY)β, which contains a polynucleotide modified such that the encoded α subunit has a QYY mutation, and pTrc99Aγα(QYY)β330-His, which contains a polynucleotide modified such that the α subunit has the QYY mutation, and such that the encoded β subunit is a deletion-type β subunit composed of amino acid positions 330 to 425, were used (US 2019-0010215).

With these vectors, site-directed mutagenesis was carried out such that the following amino acid substitutions were introduced to the subunits. Mutant 1 is a mutant in which position 154 of the γ subunit is substituted with a cysteine; position 345 of the β subunit is substituted with a cysteine; and a disulfide bond is formed between these cysteines. Mutant 2 is a mutant in which position 155 of the γ subunit is substituted with a cysteine; position 349 of the β subunit is substituted with a cysteine; and a disulfide bond is formed between these cysteines. Mutant 3 is a mutant in which position 205 of the α subunit is substituted with a cysteine; position 383 of the β subunit is substituted with a cysteine; and a disulfide bond is formed between these cysteines. Mutant 4 is a mutant in which position 205 of the α subunit is substituted with a cysteine; position 383 of the β subunit is substituted with a cysteine; a disulfide bond (α-β disulfide bond) is formed between these cysteines; position 345 of the β subunit is substituted with a cysteine; position 154 of the γ subunit is substituted with a cysteine; and a disulfide bond (β-γ disulfide bond) is formed between these cysteines. Mutant 5 is a mutant in which position 205 of the α subunit is substituted with a cysteine; position 383 of the β subunit is substituted with a cysteine; a disulfide bond (α-β disulfide bond) is formed between these cysteines; position 349 of the β subunit is substituted with a cysteine; position 155 of the γ subunit is substituted with a cysteine; and a disulfide bond (β-γ disulfide bond) is formed between these cysteines.

| | α | β | γ |
|---|---|---|---|
| Mutant 1 | | 345 | 154 |
| Mutant 2 | | 349 | 155 |
| Mutant 3 | 205 | 383 | |
| Mutant 4 | 205 | 383 & 345 | 154 |
| Mutant 5 | 205 | 383 & 349 | 155 |

*E. coli* was transformed with each vector obtained, and the resulting transformant was cultured to allow expression of each mutant GDH.

The culture and purification of glucose dehydrogenase were carried out by the method described in US 2019-0010215.

Measurement of Enzyme Activity

Each mutant GDH was heat-treated at each temperature for 15 minutes, and then the enzyme activity was measured according to the method described in US 2019-0010215 with a system using PMS/DCIP.

The results are shown in FIG. 1. As a result, QYY with no introduction of a cysteine residue showed a sharp decrease in the activity from 55° C., while the activity was maintained even at 55° C. and 65° C. in the cases of Mutant 1, Mutant 2, and Mutant 3.

Figure 2:
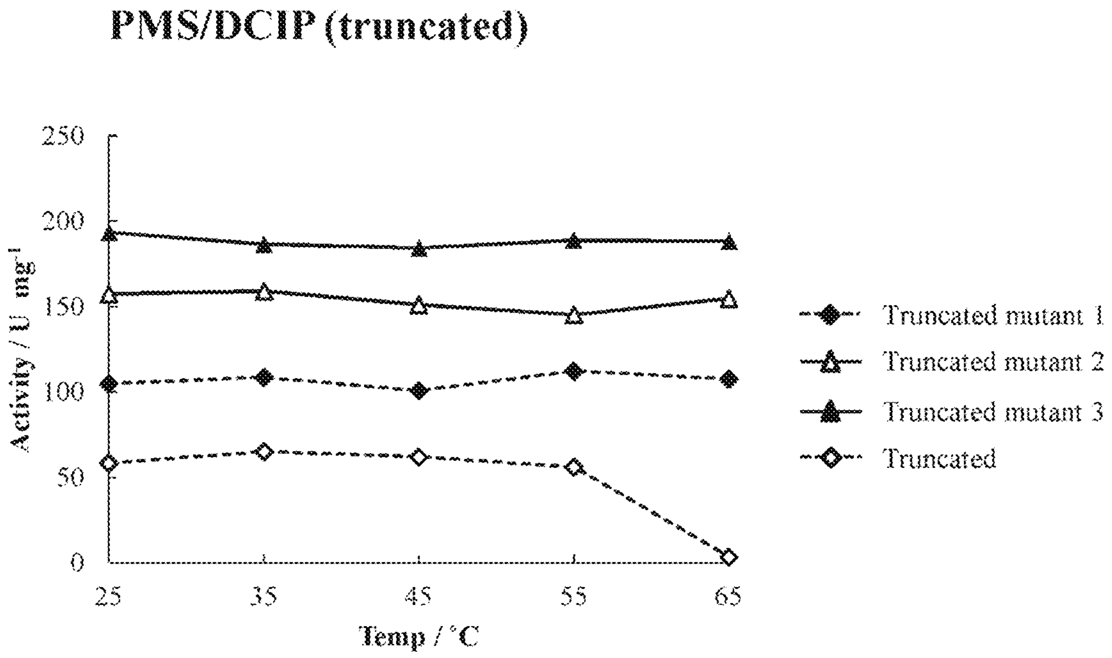
FIG. 2 is a graph illustrating the enzyme activity of each GDH from *Burkholderia cepacia* (wild type or mutants 1 to 3 with a truncated β subunit) at 25° C. to 65° C.

As shown in FIG. 2, in the cases where the deletion-type β subunit was used, and cysteine was introduced thereto, a decrease in the activity was hardly observed.

Subsequently, the thermal stability was evaluated for Mutants 4 and 5, in which cysteine was introduced not only to the α subunit, but also to the γ subunit, to form the α-β and β-γ disulfide bonds.

Figure 3:
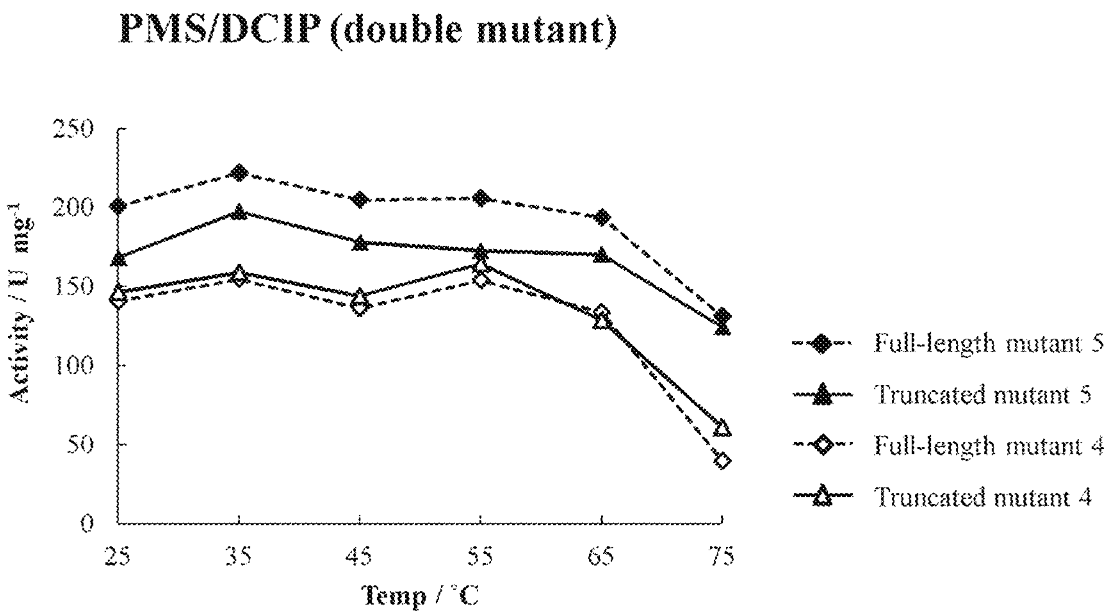
FIG. 3 is a graph illustrating the enzyme activity of each GDH from *Burkholderia cepacia* (mutants 4 and 5, with a full-length or truncated β subunit) at 25° C. to 75° C.
Figure 4:
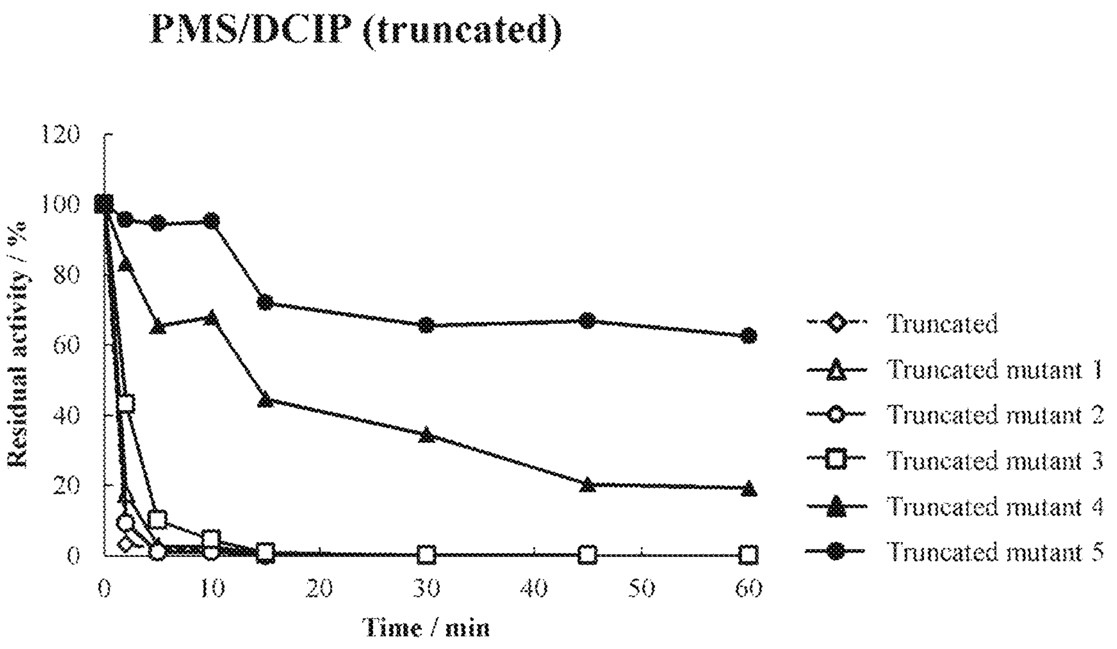
FIG. 4 is a graph illustrating the enzyme activity of each GDH from *Burkholderia cepacia* (wild type or mutants 1 to 5 with a truncated β subunit) at 75° C.

As a result, as shown in FIG. 3, Mutant 4 showed a decrease in the activity to about ⅓ relative to the original activity at 75° C. In contrast, Mutant 5, with either the normal-type β subunit or the deletion-type subunit, showed maintenance of about 70% of the original activity at 75° C., showing that its enzyme performance is less likely to decrease even at high temperature.

Subsequently, the activity was investigated after performing heat treatment at 75° C. for different lengths of time. As a result, Mutants 4 and 5 showed maintenance of the activity even after 60 minutes of the heat treatment. In particular Mutant 5 was found to be an enzyme having high thermal stability with which not less than 60% of the original activity can be maintained even after 60 minutes of the heat treatment.

Preparation of Enzyme Electrode and Measurement of Glucose

Subsequently, an enzyme electrode was prepared using Mutant 5, and used for measurement of the glucose concentration.

First, an enzyme electrode was prepared by immobilizing the Mutant, on a gold surface through a monolayer-forming molecule. As the monolayer-forming molecule, DSH, shown below, was used.

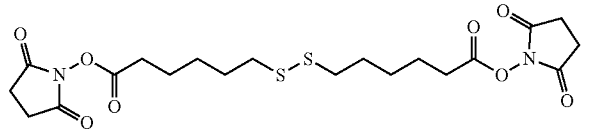

Dithiobis(succinimidyl hexanoate): DSH

Specifically, a gold wire (diameter, 0.5 mm; length, 6 to 7 cm) was immersed in Piranha solution (200 μl) at room temperature for 2 hours, and then washed with acetone. The wire was then immersed in a solution of DSH in acetone (concentration, 20 μM), and incubated at 25° C. for 24 hours to allow binding of the thiol groups of DSH to the gold surface. Subsequently, the wire was washed with acetone, and then immersed in phosphate buffer (300 μl) containing the Mutant GDH (concentration, 0.03 mg/ml), followed by incubation at 4° C. overnight to allow binding of the Mutant GDH through a functional group of DSH, thereby obtaining an enzyme electrode in which the Mutant GDH was immobilized on the surface.

Using the enzyme electrode prepared as described above, the response current value for 0 mM (background), 1 mM, 2 mM, 5 mM, 10 mM, 20 mM, or 50 mM aqueous glucose solution was measured by chronoamperometry. The glucose measurement was carried out at 37° C. using a counter electrode (Pt wire) and a reference electrode (silver/silver chloride) by application of an electric potential of +0.4 V (vs. silver/silver chloride) to the working electrode.

Figure 5:
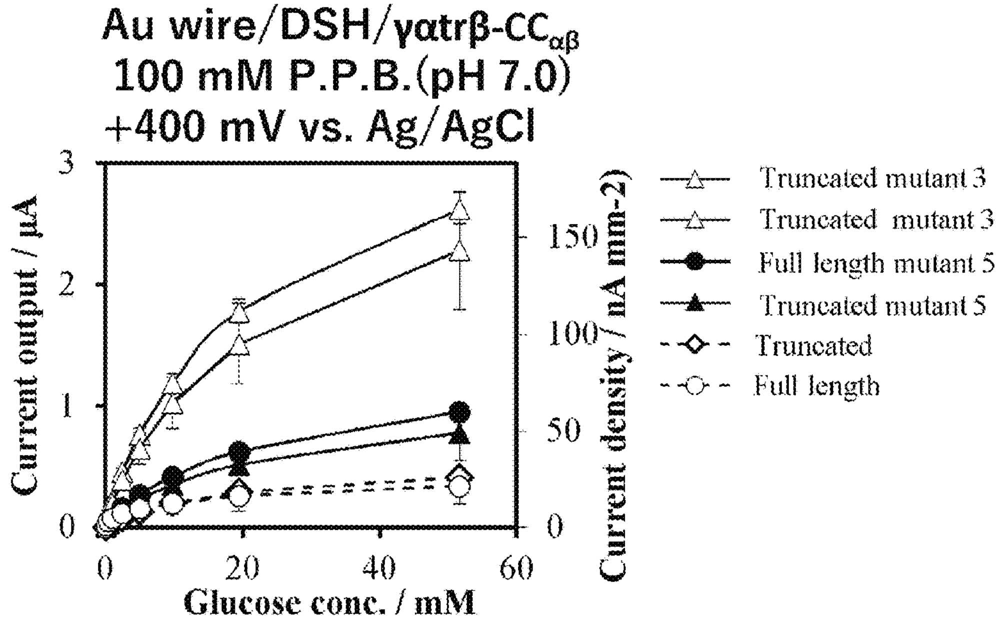
FIG. 5 is a diagram illustrating the result of measurement of the glucose-dependent electric current using an enzyme electrode comprising each GDH (wild type or mutants 3 and 5 with a full-length or truncated β subunit) from *Burkholderia cepacia*.

As a result, as shown in FIG. 5, glucose concentration dependency of the response current was found.

Thus, it was shown that the glucose concentration can be measured with a sensor using a GDH in which cysteines are introduced to bind subunits to each other by disulfide bonding. Further, it was surprisingly found that the introduction of the cysteines led to improvement of the electrode properties.

Continuous Measurement of the Response Current

Figure 6:
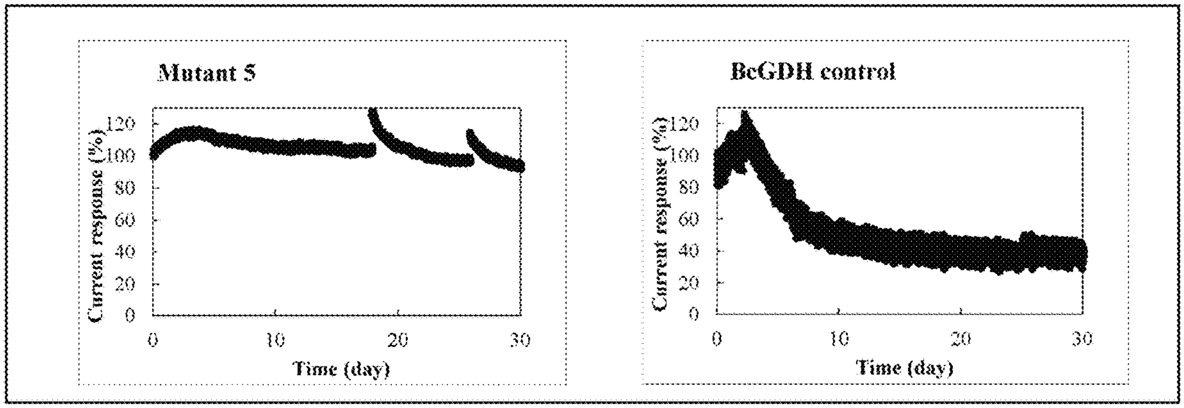
FIG. 6 is a diagram illustrating the result of continuous measurement of the electric current response using an enzyme electrode comprising a mutant GDH (Mutant 5: QYY $\alpha_{205}C\beta_{383}C$-$\gamma_{155}C\beta_{349}C$) or QYY GDH (control) from *Burkholderia cepacia*.

The enzyme electrode carrying Mutant 5 prepared as described above was immersed in a 20 mM glucose solution at room temperature together with a counter electrode (Pt wire) and a reference electrode (silver/silver chloride). The current response was continuously measured for four weeks by application of an electric potential of +0.2 V (vs. silver/silver chloride) to the working electrode and the results were compared to the enzyme electrode carrying QYY GDH with no introduction of a cysteine residue. As a result, as shown in FIG. 6, the current response of the enzyme electrode carrying Mutant 5 was maintained at high level for four weeks whereas the current response of the enzyme electrode carrying QYY GDH decreased to about 40%.

Figure 7:
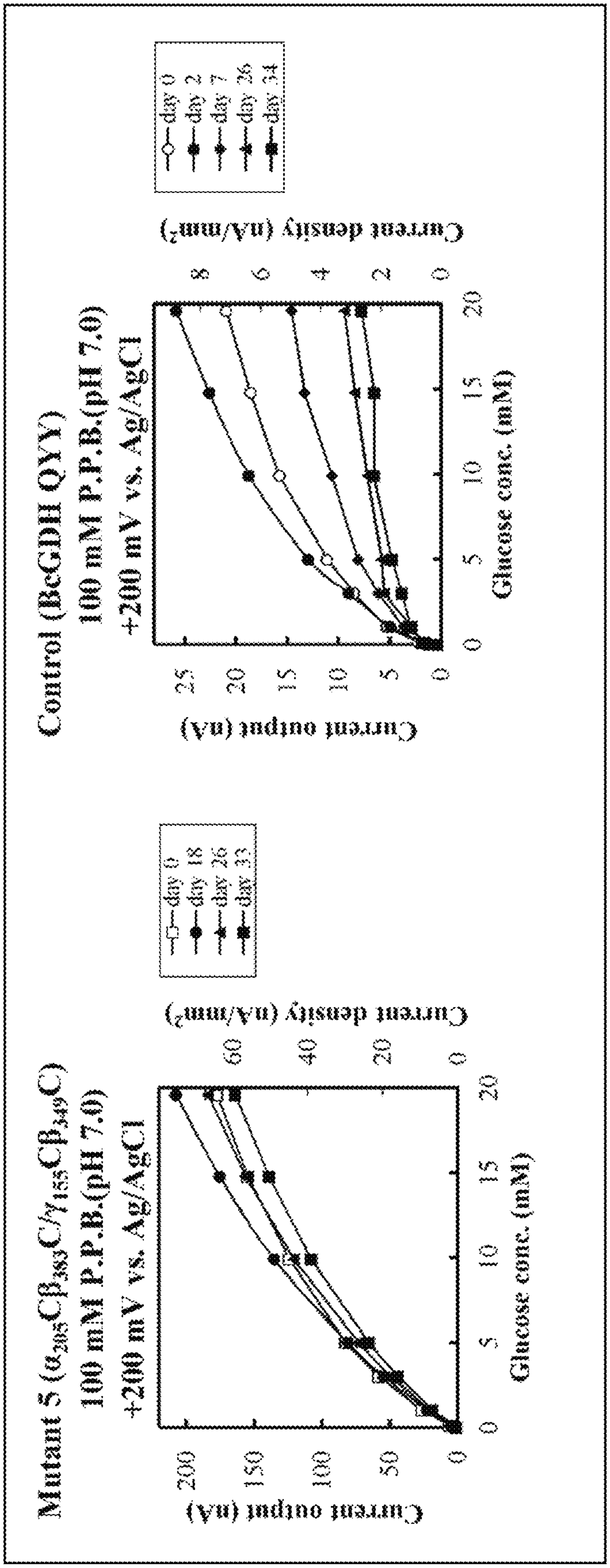
FIG. 7 is a diagram illustrating the result of measurement of the glucose-dependent electric current response on each day using an enzyme electrode comprising a mutant GDH (Mutant 5: QYY $\alpha_{205}C\beta_{383}C$-$\gamma_{155}C\beta_{349}C$) or QYY GDH (control) from *Burkholderia cepacia*.

Next, the enzyme electrode carrying Mutant 5 was immersed in a glucose solution (0, 1, 3, 5, 10, 15 and 20 mM) at room temperature together with a counter electrode (Pt wire) and a reference electrode (silver/silver chloride). The electric potential of +0.2 V (vs. silver/silver chloride) was continuously applied to the working electrode and the response current was measured over time and plotted and the results were compared to the enzyme electrode carrying QYY GDH with no introduction of a cysteine residue. As a result, as shown in FIG. 7, the glucose concentration-dependency of the current response of the enzyme electrode carrying Mutant 5 was maintained for about five weeks whereas glucose concentration-dependency of the current response of the enzyme electrode carrying QYY GDH was almost lost on Day 26 and Day 34.

These data clearly show that the enzyme having introduced cysteine residues has high stability and can be suitably used for a long-term measurement of glucose.

Example 2

Preparation of Mutant GDH from *E. americana* and Evaluation of Heat Resistance

As a GDH comprising a cytochrome C-containing subunit, a CyGDH derived from *E. americana* was used. The CyGDH derived from *E. americana* is an oligomer enzyme composed of the γ, α, and β subunits. These three subunits are encoded in the gene having the nucleotide sequence of SEQ ID NO:5. The CyGDH gene was inserted into pTrc99A.

With this vector, site-directed mutagenesis was carried out such that the following amino acid substitutions were introduced to the subunits. Mutant E is a mutant in which position 202 of the α subunit is substituted with a cysteine; position 375 of the β subunit is substituted with a cysteine; a disulfide bond (α-β disulfide bond) is formed between these cysteines; position 341 of the β subunit is substituted with a cysteine; position 157 of the γ subunit is substituted with a cysteine; and a disulfide bond (β-γ disulfide bond) is formed between these cysteines.

*E. coli* was transformed with each vector obtained, and the resulting transformant was cultured to allow expression of the mutant GDH.

The culture and purification of glucose dehydrogenase were carried out by the method described in US 2019-0010215.

Measurement of Enzyme Activity

The mutant GDH was heat-treated at 65° C., and the enzyme activity was measured according to the method described in US 2019-0010215 with a system using PMS/DCIP and the time-dependent change of the enzyme activity was plotted.

Figure 8:
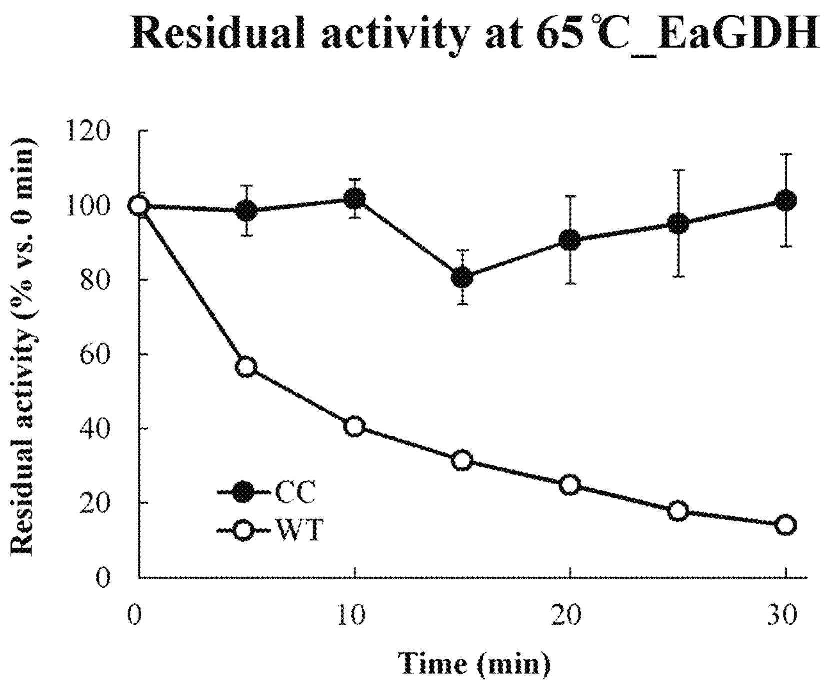
FIG. 8 is a graph illustrating the enzyme activity of GDH from *Ewingella americana* (Ea) (disulfide-formed mutant or wild type) at 65° C.

The results are shown in FIG. 8. As a result, the wild-type GDH with no introduction of a cysteine residue showed a sharp decrease in the activity at 65° C., while the activity of the Mutant GDH having α-β disulfide bond and β-γ disulfide bond was maintained for 30 minutes at 65° C.

These data clearly show that the disulfide bond formation is also effective for enhancing stability of oligomeric GDH enzymes of various origin.

Example 3

Preparation of Mutant GDHs from *Silvimonas terrae* and Evaluation of Heat Resistance As a GDH comprising a cytochrome C-containing subunit, a CyGDH derived from *Silvimonas terrae* was used. The CyGDH derived from *Silvimonas terrae* is an oligomer enzyme composed of the γ, α, and β subunits. These three subunits are encoded in the gene having the nucleotide sequence of SEQ ID NO: 11. The CyGDH gene was inserted into pTrc99A.

With this vector, site-directed mutagenesis was carried out such that the following amino acid substitutions were introduced to the subunits. Two mutant CyGDHs were prepared: One is a mutant in which proline at position 204 of the α subunit is substituted with a cysteine; histidine at position 382 of the β subunit is substituted with a cysteine; a disulfide bond (α-β disulfide bond) is formed between these cysteines; alanine at position 347 of the β subunit is substituted with a cysteine; alanine at position 168 of the γ subunit is substituted with a cysteine; and a disulfide bond (β-γ disulfide bond) is formed between these cysteines (αP204CβH382C-γA168CβA347C).
The other is a mutant in which proline at position 204 of the α subunit is substituted with a cysteine; histidine at position 382 of the β subunit is substituted with a cysteine; a disulfide bond (α-β disulfide bond) is formed between these cysteines (αP204CβH382C).

*E. coli* was transformed with each vector obtained, and the resulting transformants were cultured to allow expression of the mutant GDHs.

The culture and purification of glucose dehydrogenase were carried out by the method described in US 2019-0010215.

Measurement of Enzyme Activity

The mutant GDHs as wells as the wild type GDH were heat-treated at 60° C., and the enzyme activity was measured according to the method described in US 2019-0010215 with a system using Ru/MTT and the time-dependent change of the enzyme activity was plotted.

Figure 12:
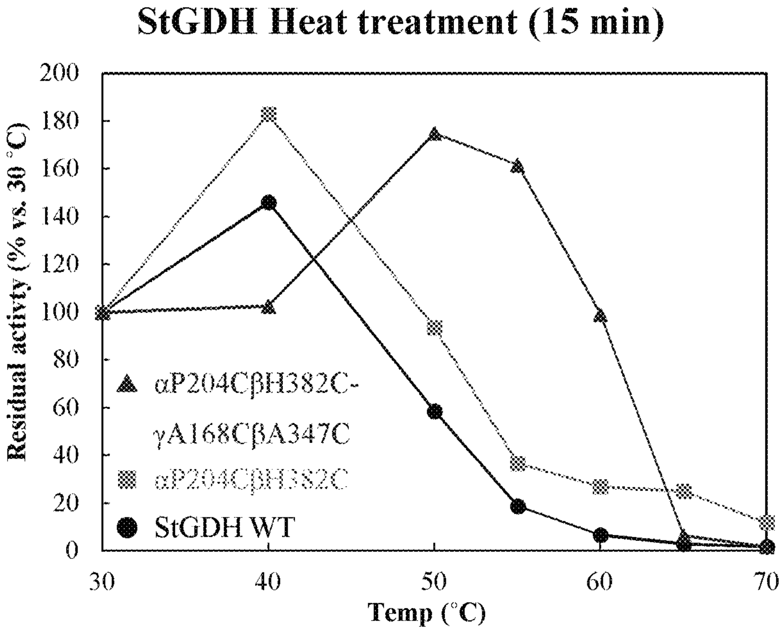
FIG. 12 is a graph illustrating the enzyme activity of each of GDH from *Silvimonas terrae* (St) (wild type, αP204CβH382C and αP204CβH382C-γA168CβA347C) at 30° C. to 70° C.
Figure 13:
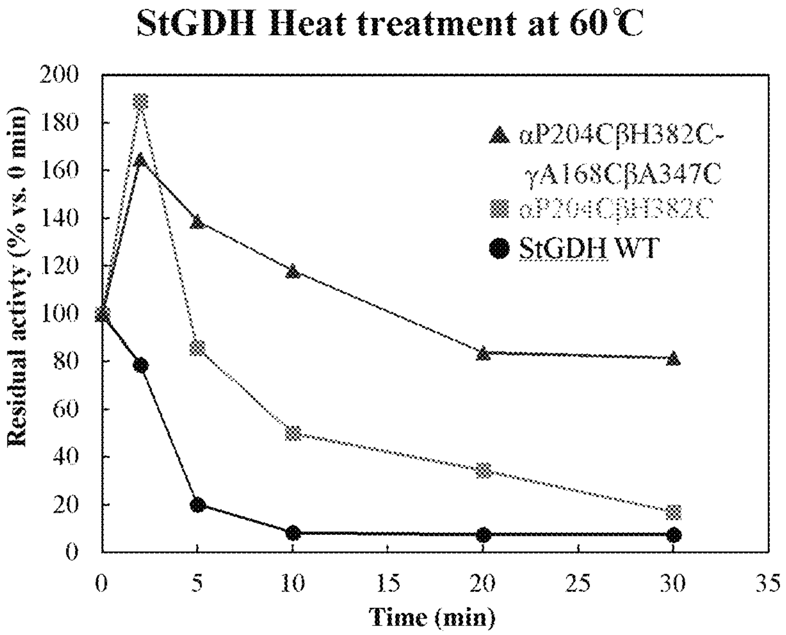
FIG. 13 is a graph illustrating the enzyme activity of GDH from *Silvimonas terrae* (St) (wild type, αP204CβH382C and αP204CβH382C-γA168CβA347C) at 60° C.

As shown in FIG. 12, the wild-type GDH with no introduction of a cysteine residue showed a sharp decrease in the activity as the temperature increased, while the activity of the Mutant GDH having α-β disulfide bond showed an enhanced thermal stability and the activity of the Mutant GDH having α-β disulfide bond and β-γ disulfide bond was maintained up to 60° C. Furthermore, as shown in FIG. 13, the wild-type GDH with no introduction of a cysteine residue showed a sharp decrease in the activity at 60° C., while the activity of the Mutant GDH having α-β disulfide bond showed an enhanced thermal stability and the activity of the Mutant GDH having α-β disulfide bond and β-γ disulfide bond was maintained for 30 minutes at 60° C.

Example 4

Preparation of Mutant GDHs from *Zymobacter palmae* and Evaluation of Heat Resistance As a GDH comprising a cytochrome C-containing subunit, a CyGDH derived from *Zymobacter palmae* was used. The CyGDH derived from *Zymobacter palmae* is an oligomer enzyme composed of the γ, α, and β subunits. These three subunits are encoded in the gene having the nucleotide sequence of SEQ ID NO: 15. A modified CyGDH gene in which the nucleotide "g" at position 55 is replaced with "a" such that Val at position 19 in SEQ ID NO: 16 is changed to Met and the γ subunit is translated from this position was inserted into pTrc99A.

With this vector, site-directed mutagenesis was carried out such that the following amino acid substitutions were introduced to the subunits. Two mutant CyGDHs were prepared: One is a mutant in which proline at position 200 of the α subunit is substituted with a cysteine; aspartic acid at position 389 of the β subunit is substituted with a cysteine; a disulfide bond (α-β disulfide bond) is formed between these cysteines; tyrosine at position 355 of the β subunit is substituted with a cysteine; arginine at position 164 of the γ subunit which corresponds to arginine at position 182 in SEQ ID NO: 16 is substituted with a cysteine; and a disulfide bond (β-γ disulfide bond) is formed between these cysteines (αP200CβD389C-γR182CβY355C). The other is a mutant in which proline at position 200 of the α subunit is substituted with a cysteine; aspartic acid at position 389 of the β subunit is substituted with a cysteine; a disulfide bond (α-β disulfide bond) is formed between these cysteines (αP200CβD389C).

*E. coli* was transformed with each vector obtained, and the resulting transformants were cultured to allow expression of the mutant GDHs.

The culture and purification of glucose dehydrogenase were carried out by the method described in US 2019-0010215.

Measurement of Enzyme Activity

The mutant GDHs as wells as the wild type GDH were heat-treated at 60° C., and the enzyme activity was measured according to the method described in US 2019-0010215 with a system using Ru/MTT and the time-dependent change of the enzyme activity was plotted.

Figure 14:
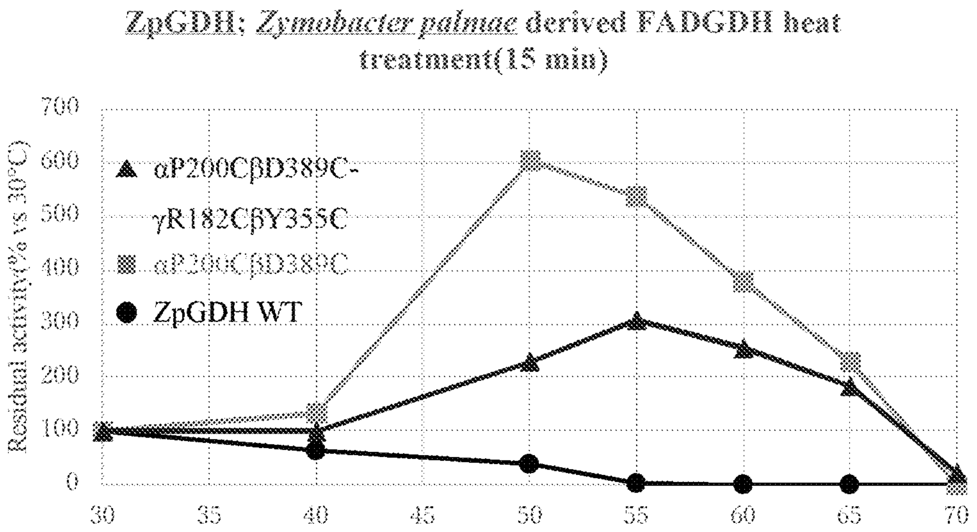
FIG. 14 is a graph illustrating the enzyme activity of each GDH from *Zymobacter palmae* (Zp) (wild type, αP200CβD389C and αP200CβD389C-γR182CβY355C) at 30° C. to 70° C.
Figure 15:
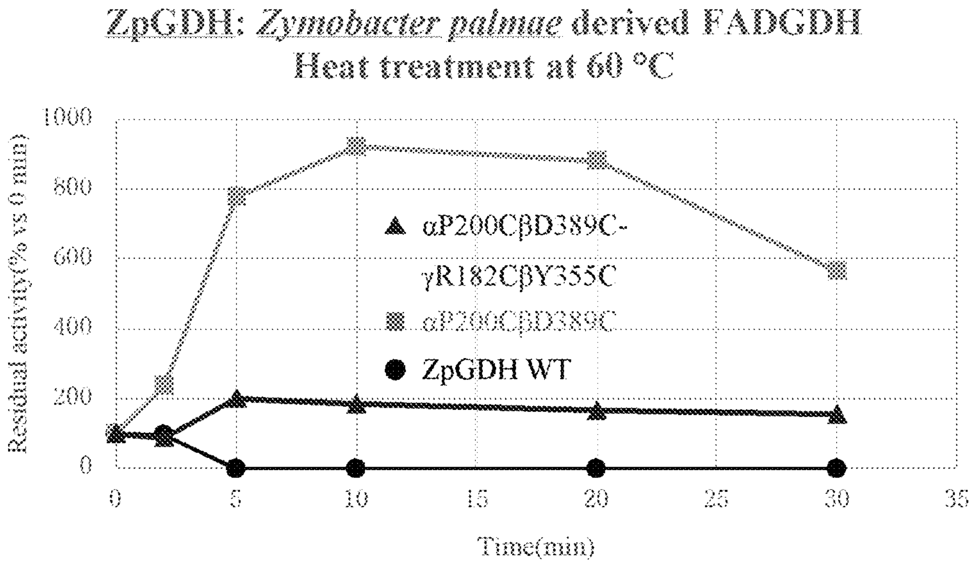
FIG. 15 is a graph illustrating the enzyme activity of GDH from *Zymobacter palmae* (Zp) (wild type, αP200CβD389C and αP200CβD389C-γR182CβY355C) at 60° C.

As shown in FIG. 14, the wild-type GDH with no introduction of a cysteine residue showed a decrease in the activity as the temperature increased, while the activity of the Mutant GDH having α-β disulfide bond and the activity of the Mutant GDH having α-β disulfide bond and β-γ disulfide bond were maintained at high levels up to 65° C. Furthermore, as shown in FIG. 15, the wild-type GDH with no introduction of a cysteine residue showed a sharp decrease to zero in the activity at 60° C., while the activity of the Mutant GDH having α-β disulfide bond and the activity of the Mutant GDH having α-β disulfide bond and β-γ disulfide bond were maintained at high levels for 30 minutes at 60° C.

Example 5

Preparation of Mutant GDHs from *Cobetia* sp. and Evaluation of Heat Resistance

As a GDH comprising a cytochrome C-containing subunit, a CyGDH derived from *Cobetia* sp. was used. The CyGDH derived from *Cobetia* sp. is an oligomer enzyme composed of the γ, α, and β subunits. These three subunits are encoded in the gene having the nucleotide sequence of SEQ ID NO: 19. A CyGDH gene in which the γ subunit (amino acids 14-207 of SEQ ID NO: 20) is translated from the "atg" codon at positions 40-42 in SEQ ID NO: 19 was inserted into pTrc99A.

With this vector, site-directed mutagenesis was carried out such that the following amino acid substitutions were introduced to the subunits. One mutant CyGDH was prepared which is a mutant in which proline at position 204 of the α subunit is substituted with a cysteine; serine at position 467 of the β subunit is substituted with a cysteine; a disulfide bond (α-β disulfide bond) is formed between these cysteines; tyrosine at position 433 of the β subunit is substituted with a cysteine; glutamine at position 185 of the γ subunit which corresponds to glutamine at position 198 in SEQ ID NO: 20 is substituted with a cysteine; and a disulfide bond (β-γ disulfide bond) is formed between these cysteines (αP204CβS467C-γQ198CβY433C).

*E. coli* was transformed with each vector obtained, and the resulting transformants were cultured to allow expression of the mutant GDHs.

The culture and purification of glucose dehydrogenase were carried out by the method described in US 2019-0010215.

Measurement of Enzyme Activity

The mutant GDH as wells as the wild type GDH were heat-treated at 60° C., and the enzyme activity was measured according to the method described in US 2019-0010215 with a system using Ru/MTT and the time-dependent change of the enzyme activity was plotted.

Figure 16:
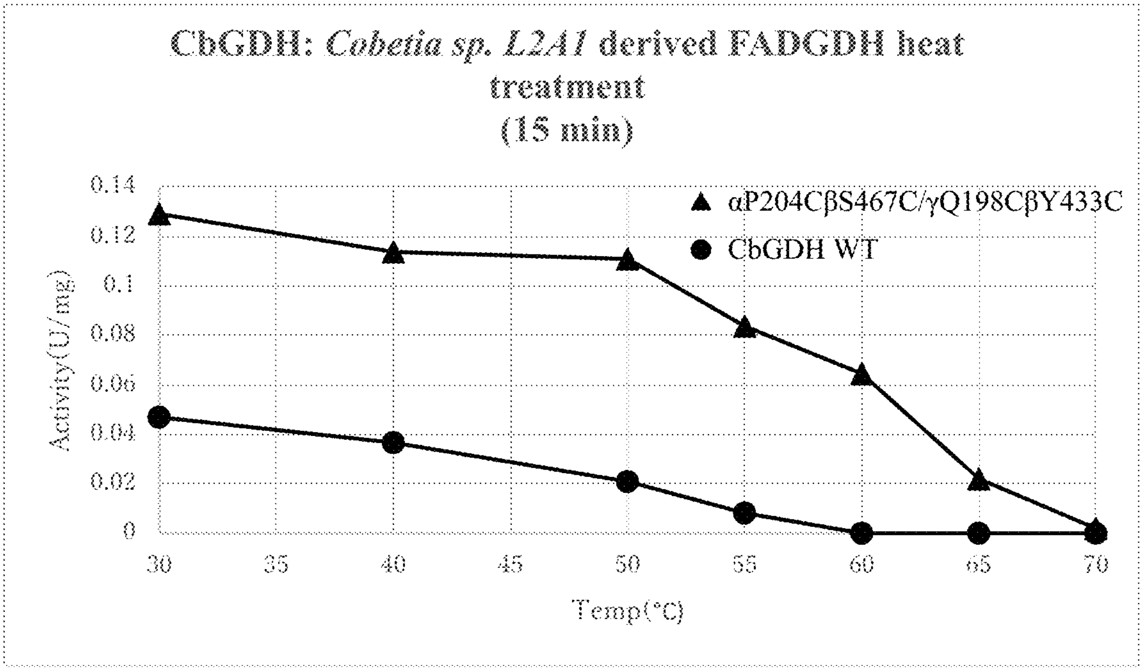
FIG. 16 is a graph illustrating the enzyme activity of each GDH from *Cobetia* sp. (Cb) L2A1 strain (wild type, and αP204CβS467C-γQ198CβY433C) at 30° C. to 70° C.
Figure 17:
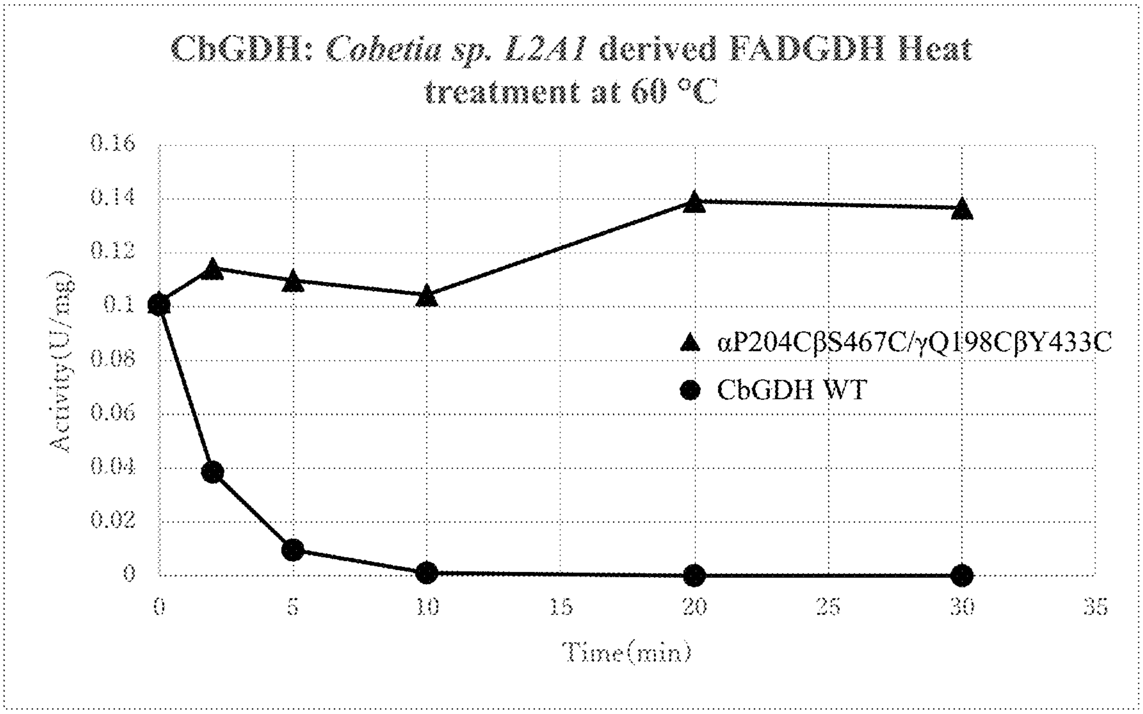
FIG. 17 is a graph illustrating the enzyme activity of GDH from *Cobetia* sp. (Cb) L2A1 strain (wild type, and αP204CβS467C-γQ198CβY433C) at 60° C.

As shown in FIG. 16, the wild-type GDH with no introduction of a cysteine residue showed a decrease in the activity as the temperature increased, while the activity of the Mutant GDH having α-β disulfide bond and β-γ disulfide bond was maintained at high levels up to 60° C. Furthermore, as shown in FIG. 17, the wild-type GDH with no introduction of a cysteine residue showed a sharp decrease to zero in the activity at 60° C., while t the activity of the Mutant GDH having α-β disulfide bond and β-γ disulfide bond were maintained at high levels for 30 minutes at 60° C.

These data clearly show that the disulfide bond formation is also effective for enhancing stability of oligomeric GDH enzymes of various origin.

The contents of all publications including patents and patent applications as well as non-patent documents cited in the present description are hereby incorporated by reference to the same extent as if all contents were clearly described.

What is claimed is:

1. A mutant FAD-dependent glucose dehydrogenase comprising:

a catalytic subunit;

an electron transfer subunit; and a hitchhiker subunit;

wherein each of the amino acid sequence of the catalytic subunit and the amino acid sequence of the electron transfer subunit comprises a cysteine residue introduced therein, the catalytic subunit and the electron transfer subunit being bound to each other through a disulfide bond between the cysteine residues, wherein the cysteine residue introduced in the catalytic subunit is at an amino acid residue corresponding to a proline residue at position 205 of SEQ ID NO:3, and the cysteine residue introduced in the electron transfer subunit is at an amino acid residue corresponding to an aspartic acid residue at position 383 of SEQ ID NO:4; or the cysteine residue introduced in the catalytic subunit is at an amino acid residue corresponding to an asparagine residue at position 215 of SEQ ID NO:3, and the cysteine residue introduced in the electron transfer subunit is at an amino acid residue corresponding to a threonine residue at position 336 of SEQ ID NO:4.

2. The mutant FAD-dependent glucose dehydrogenase according to claim 1, wherein the amino acid sequence of the electron transfer subunit comprises a second cysteine residue introduced therein, and the amino acid sequence of the hitchhiker subunit comprises a cysteine residue introduced therein, the hitchhiker subunit and the electron transfer subunit being bound to each other through a disulfide bond between the cysteine residues, wherein the second cysteine residue is at an amino acid residue corresponding to the threonine residue at position 345 of SEQ ID NO:4, and the cysteine residue introduced in the hitchhiker subunit is at an amino acid residue corresponding to the asparagine residue at position 154 of SEQ ID NO:2; or the second cysteine residue is at an amino acid residue corresponding to tyrosine residue at position 349 of SEQ ID NO:4, and the cysteine residue introduced in the hitchhiker subunit is at an amino acid residue corresponding to the lysine residue at position 155 of SEQ ID NO:2.

3. The mutant FAD-dependent glucose dehydrogenase according to claim 1, wherein the amino acid sequence of the catalytic subunit has an identity of at least 60% to SEQ ID NO: 3.

4. The mutant FAD-dependent glucose dehydrogenase according to claim 1, wherein the amino acid sequence of the electron transfer subunit has an identity of at least 60% to the amino acid sequence of SEQ ID NO:4, or the amino acid sequence of amino acid positions 314 to 425 of SEQ ID NO:4.

5. The mutant FAD-dependent glucose dehydrogenase according to claim 1, wherein the amino acid sequence of the hitchhiker subunit has an identity of at least 60% to SEQ ID NO: 2.

6. The mutant FAD-dependent glucose dehydrogenase according to claim 2, wherein the catalytic subunit comprises an amino acid sequence having at least 60% identity to SEQ ID NO: 7 wherein cysteine is introduced at the position corresponding to the proline residue at position 202 in SEQ ID NO: 7, the electron transfer subunit comprises an amino acid sequence having at least 60% identity to SEQ ID NO: 8 or amino acids 306 to 420 of SEQ ID NO: 8 wherein a first cysteine is introduced at the position corresponding to the glutamic acid residue at position 375 in SEQ ID NO: 8 and a second cysteine is introduced at the position corresponding to the tyrosine residue at position 341 in SEQ ID NO: 8, and the hitchhiker subunit comprises an amino acid sequence having at least 60% identity to SEQ ID NO: 6 wherein cysteine is introduced at the position corresponding to the arginine residue at position 157 in SEQ ID NO: 6.

7. The mutant FAD-dependent glucose dehydrogenase according to claim 2, wherein the catalytic subunit comprises an amino acid sequence having at least 60% identity to SEQ ID NO: 13 wherein cysteine is introduced at the position corresponding to the proline residue at position 204 in SEQ ID NO: 13, the electron transfer subunit comprises an amino acid sequence having at least 60% identity to SEQ ID NO: 14 or amino acids 332 to 481 of SEQ ID NO: 14 wherein a first cysteine is introduced at the position corresponding to the histidine residue at position 382 in SEQ ID NO: 14 and a second cysteine is introduced at the position corresponding to the alanine residue at position 347 in SEQ ID NO: 14, and the hitchhiker subunit comprises an amino acid sequence having at least 60% identity to SEQ ID NO: 12 wherein cysteine is introduced at the position corresponding to the alanine residue at position 168 in SEQ ID NO: 12.

8. The mutant FAD-dependent glucose dehydrogenase according to claim 2, wherein the catalytic subunit comprises an amino acid sequence having at least 60% identity to SEQ ID NO: 17 wherein cysteine is introduced at the position corresponding to the proline residue at position 200 in SEQ ID NO: 17, the electron transfer subunit comprises an amino acid sequence having at least 60% identity to SEQ ID NO: 18 or amino acids 340 to 465 of SEQ ID NO: 18 wherein a first cysteine is introduced at the position corresponding to the aspartic acid residue at position 389 in SEQ ID NO: 18 and a second cysteine is introduced at the position corresponding to the tyrosine residue at position 355 in SEQ ID NO: 18, and the hitchhiker subunit comprises an amino acid sequence having at least 60% identity to SEQ ID NO: 16 or amino acids 19 to 195 of SEQ ID NO: 16 wherein cysteine is introduced at the position corresponding to the arginine residue at position 182 in SEQ ID NO: 16.

9. The mutant FAD-dependent glucose dehydrogenase according to claim 2, wherein the catalytic subunit comprises an amino acid sequence having at least 60% identity to SEQ ID NO: 21 wherein cysteine is introduced at the position corresponding to the proline residue at position 204 in SEQ ID NO: 21, the electron transfer subunit comprises an amino acid sequence having at least 60% identity to SEQ ID NO: 22 or amino acids 418 to 522 of SEQ ID NO: 22 wherein a first cysteine is introduced at the position corresponding to the serine residue at position 467 in SEQ ID NO: 22 and a second cysteine is introduced at the position corresponding to the tyrosine residue at position 433 in SEQ ID NO: 22, and the hitchhiker subunit comprises an amino acid sequence having at least 60% identity to SEQ ID NO: 20 or amino acids 14 to 207 of SEQ ID NO: 20 wherein cysteine is introduced at the position corresponding to the glutamine residue at position 198 in SEQ ID NO: 20.

10. An enzyme electrode comprising the FAD-dependent glucose dehydrogenase according to claim 1.

11. A biosensor comprising the enzyme electrode according to claim 10.

12. The mutant FAD-dependent glucose dehydrogenase according to claim 1, wherein the amino acid sequence of the catalytic subunit comprises a cysteine residue introduced at an amino acid residue corresponding to the proline residue at position 205 of SEQ ID NO:3, and the amino acid sequence of the electron transfer subunit comprises a cysteine residue introduced at an amino acid residue corresponding to the aspartic acid residue at position 383 of SEQ ID NO:4.

13. The mutant FAD-dependent glucose dehydrogenase according to claim 1, wherein the amino acid sequence of the catalytic subunit comprises a cysteine residue introduced at an amino acid residue corresponding to asparagine residue at position 215 of SEQ ID NO:3, and the amino acid sequence of the electron transfer subunit comprises a cysteine residue introduced at an amino acid residue corresponding to the threonine residue at position 336 of SEQ ID NO:4.

14. The mutant FAD-dependent glucose dehydrogenase according to claim 2, wherein the second cysteine residue is at an amino acid residue corresponding to the threonine residue at position 345 of SEQ ID NO:4, and the cysteine residue introduced in the hitchhiker subunit is at an amino acid residue corresponding to the asparagine residue at position 154 of SEQ ID NO:2.

15. The mutant FAD-dependent glucose dehydrogenase according to claim 2, wherein the second cysteine residue is at an amino acid residue corresponding to tyrosine residue at position 349 of SEQ ID NO:4, and the cysteine residue introduced in the hitchhiker subunit is at an amino acid residue corresponding to the lysine residue at position 155 of SEQ ID NO:2.

* * * * *

```
                         SEQUENCE LISTING


<160> NUMBER OF SEQ ID NOS: 31

<210> SEQ ID NO 1
<211> LENGTH: 3706
<212> TYPE: DNA
<213> ORGANISM: Burkholderia cepacia
<220> FEATURE:
<221> NAME/KEY: CDS
<222> LOCATION: (258)..(761)
<220> FEATURE:
<221> NAME/KEY: CDS
<222> LOCATION: (764)..(2380)
<220> FEATURE:
<221> NAME/KEY: CDS
<222> LOCATION: (2386)..(3660)

<400> SEQUENCE: 1

aagctttctg tttgattgca cgcgattcta accgagcgtc tgtgaggcgg aacgcgacat      60

gcttcgtgtc gcacacgtgt cgcgccgacg acacaaaaat gcagcgaaat ggctgatcgt     120

tacgaatggc tgacacattg aatggactat aaaaccattg tccgttccgg aatgtgcgcg     180

tacatttcag gtccgcgccg atttttgaga aatatcaagc gtggttttcc cgaatccggt     240

gttcgagaga aggaaac atg cac aac gac aac act ccc cac tcg cgt cgc        290
                   Met His Asn Asp Asn Thr Pro His Ser Arg Arg
                   1               5                   10

cac ggc gac gca gcc gca tca ggc atc acg cgg cgt caa tgg ttg caa       338
His Gly Asp Ala Ala Ala Ser Gly Ile Thr Arg Arg Gln Trp Leu Gln
            15                  20                  25

ggc gcg ctg gcg ctg acc gca gcg ggc ctc acg ggt tcg ctg aca ttg       386
Gly Ala Leu Ala Leu Thr Ala Ala Gly Leu Thr Gly Ser Leu Thr Leu
        30                  35                  40

cgg gcg ctt gca gac aac ccc ggc act gcg ccg ctc gat acg ttc atg       434
Arg Ala Leu Ala Asp Asn Pro Gly Thr Ala Pro Leu Asp Thr Phe Met
    45                  50                  55

acg ctt tcc gaa tcg ctg acc ggc aag aaa ggg ctc agc cgc gtg atc       482
Thr Leu Ser Glu Ser Leu Thr Gly Lys Lys Gly Leu Ser Arg Val Ile
60                  65                  70                  75

ggc gag cgc ctg ctg cag gcg ctg cag aag ggc tcg ttc aag acg gcc       530
Gly Glu Arg Leu Leu Gln Ala Leu Gln Lys Gly Ser Phe Lys Thr Ala
                80                  85                  90

gac agc ctg ccg cag ctc gcc ggc gcg ctc gcg tcc ggt tcg ctg acg       578
Asp Ser Leu Pro Gln Leu Ala Gly Ala Leu Ala Ser Gly Ser Leu Thr
            95                  100                 105
```

-continued

```
cct gaa cag gaa tcg ctc gca ctg acg atc ctc gag gcc tgg tat ctc      626
Pro Glu Gln Glu Ser Leu Ala Leu Thr Ile Leu Glu Ala Trp Tyr Leu
        110                 115                 120

ggc atc gtc gac aac gtc gtg att acg tac gag gaa gca tta atg ttc      674
Gly Ile Val Asp Asn Val Val Ile Thr Tyr Glu Glu Ala Leu Met Phe
    125                 130                 135

ggc gtc gtg tcc gat acg ctc gtg atc cgt tcg tat tgc ccc aac aaa      722
Gly Val Val Ser Asp Thr Leu Val Ile Arg Ser Tyr Cys Pro Asn Lys
140                 145                 150                 155

ccc ggc ttc tgg gcc gac aaa ccg atc gag agg caa gcc tg atg gcc       769
Pro Gly Phe Trp Ala Asp Lys Pro Ile Glu Arg Gln Ala    Met Ala
                160                 165                    170

gat acc gat acg caa aag gcc gac gtc gtc gtc gtt gga tcg ggt gtc      817
Asp Thr Asp Thr Gln Lys Ala Asp Val Val Val Val Gly Ser Gly Val
                175                 180                 185

gcg ggc gcg atc gtc gcg cat cag ctc gcg atg gcg ggc aag gcg gtg      865
Ala Gly Ala Ile Val Ala His Gln Leu Ala Met Ala Gly Lys Ala Val
            190                 195                 200

atc ctg ctc gaa gcg ggc ccg cgc atg ccg cgc tgg gaa atc gtc gag      913
Ile Leu Leu Glu Ala Gly Pro Arg Met Pro Arg Trp Glu Ile Val Glu
        205                 210                 215

cgc ttc cgc aat cag ccc gac aag atg gac ttc atg gcg ccg tac ccg      961
Arg Phe Arg Asn Gln Pro Asp Lys Met Asp Phe Met Ala Pro Tyr Pro
    220                 225                 230

tcg agc ccc tgg gcg ccg cat ccc gag tac ggc ccg ccg aac gac tac     1009
Ser Ser Pro Trp Ala Pro His Pro Glu Tyr Gly Pro Pro Asn Asp Tyr
235                 240                 245                 250

ctg atc ctg aag ggc gag cac aag ttc aac tcg cag tac atc cgc gcg     1057
Leu Ile Leu Lys Gly Glu His Lys Phe Asn Ser Gln Tyr Ile Arg Ala
                255                 260                 265

gtg ggc ggc acg acg tgg cac tgg gcc gcg tcg gcg tgg cgc ttc att     1105
Val Gly Gly Thr Thr Trp His Trp Ala Ala Ser Ala Trp Arg Phe Ile
            270                 275                 280

ccg aac gac ttc aag atg aag agc gtg tac ggc gtc ggc cgc gac tgg     1153
Pro Asn Asp Phe Lys Met Lys Ser Val Tyr Gly Val Gly Arg Asp Trp
        285                 290                 295

ccg atc cag tac gac gat ctc gag ccg tac tat cag cgc gcg gag gaa     1201
Pro Ile Gln Tyr Asp Asp Leu Glu Pro Tyr Tyr Gln Arg Ala Glu Glu
    300                 305                 310

gag ctc ggc gtg tgg ggc ccg ggc ccc gag gaa gat ctg tac tcg ccg     1249
Glu Leu Gly Val Trp Gly Pro Gly Pro Glu Glu Asp Leu Tyr Ser Pro
315                 320                 325                 330

cgc aag cag ccg tat ccg atg ccg ccg ctg ccg ttg tcg ttc aac gag     1297
Arg Lys Gln Pro Tyr Pro Met Pro Pro Leu Pro Leu Ser Phe Asn Glu
                335                 340                 345

cag acc atc aag acg gcg ctg aac aac tac gat ccg aag ttc cat gtc     1345
Gln Thr Ile Lys Thr Ala Leu Asn Asn Tyr Asp Pro Lys Phe His Val
            350                 355                 360

gtg acc gag ccg gtc gcg cgc aac agc cgc ccg tac gac ggc cgc ccg     1393
Val Thr Glu Pro Val Ala Arg Asn Ser Arg Pro Tyr Asp Gly Arg Pro
        365                 370                 375

act tgt tgc ggc aac aac aac tgc atg ccg atc tgc ccg atc ggc gcg     1441
Thr Cys Cys Gly Asn Asn Asn Cys Met Pro Ile Cys Pro Ile Gly Ala
    380                 385                 390

atg tac aac ggc atc gtg cac gtc gag aag gcc gaa cgc gcc ggc gcg     1489
Met Tyr Asn Gly Ile Val His Val Glu Lys Ala Glu Arg Ala Gly Ala
395                 400                 405                 410

aag ctg atc gag aac gcg gtc gtc tac aag ctc gag acg ggc ccg gac     1537
Lys Leu Ile Glu Asn Ala Val Val Tyr Lys Leu Glu Thr Gly Pro Asp
                415                 420                 425
```

-continued

```
aag cgc atc gtc gcg gcg ctc tac aag gac aag acg ggc gcc gag cat     1585
Lys Arg Ile Val Ala Ala Leu Tyr Lys Asp Lys Thr Gly Ala Glu His
            430                 435                 440

cgc gtc gaa ggc aag tat ttc gtg ctc gcc gcg aac ggc atc gag acg     1633
Arg Val Glu Gly Lys Tyr Phe Val Leu Ala Ala Asn Gly Ile Glu Thr
        445                 450                 455

ccg aag atc ctg ctg atg tcc gcg aac cgc gat ttc ccg aac ggt gtc     1681
Pro Lys Ile Leu Leu Met Ser Ala Asn Arg Asp Phe Pro Asn Gly Val
    460                 465                 470

gcg aac agc tcg gac atg gtc ggc cgc aac ctg atg gac cat ccg ggc     1729
Ala Asn Ser Ser Asp Met Val Gly Arg Asn Leu Met Asp His Pro Gly
475                 480                 485                 490

acc ggc gtg tcg ttc tat gcg agc gag aag ctg tgg ccg ggc cgc ggc     1777
Thr Gly Val Ser Phe Tyr Ala Ser Glu Lys Leu Trp Pro Gly Arg Gly
                495                 500                 505

ccg cag gag atg acg tcg ctg atc ggt ttc cgc gac ggt ccg ttc cgc     1825
Pro Gln Glu Met Thr Ser Leu Ile Gly Phe Arg Asp Gly Pro Phe Arg
            510                 515                 520

gcg acc gaa gcg gcg aag aag atc cac ctg tcg aac ctg tcg cgc atc     1873
Ala Thr Glu Ala Ala Lys Lys Ile His Leu Ser Asn Leu Ser Arg Ile
        525                 530                 535

gac cag gag acg cag aag atc ttc aag gcc ggc aag ctg atg aag ccc     1921
Asp Gln Glu Thr Gln Lys Ile Phe Lys Ala Gly Lys Leu Met Lys Pro
    540                 545                 550

gac gag ctc gac gcg cag atc cgc gac cgt tcc gca cgc tac gtg cag     1969
Asp Glu Leu Asp Ala Gln Ile Arg Asp Arg Ser Ala Arg Tyr Val Gln
555                 560                 565                 570

ttc gac tgc ttc cac gaa atc ctg ccg caa ccc gag aac cgc atc gtg     2017
Phe Asp Cys Phe His Glu Ile Leu Pro Gln Pro Glu Asn Arg Ile Val
                575                 580                 585

ccg agc aag acg gcg acc gat gcg atc ggc att ccg cgc ccc gag atc     2065
Pro Ser Lys Thr Ala Thr Asp Ala Ile Gly Ile Pro Arg Pro Glu Ile
            590                 595                 600

acg tat gcg atc gac gac tac gtg aag cgc ggc gcc gcg cat acg cgc     2113
Thr Tyr Ala Ile Asp Asp Tyr Val Lys Arg Gly Ala Ala His Thr Arg
        605                 610                 615

gag gtc tac gcg acc gcc gcg aag gtg ctc ggc ggc acg gac gtc gtg     2161
Glu Val Tyr Ala Thr Ala Ala Lys Val Leu Gly Gly Thr Asp Val Val
    620                 625                 630

ttc aac gac gaa ttc gcg ccg aac aat cac atc acg ggc tcg acg atc     2209
Phe Asn Asp Glu Phe Ala Pro Asn Asn His Ile Thr Gly Ser Thr Ile
635                 640                 645                 650

atg ggc gcc gat gcg cgc gac tcc gtc gtc gac aag gac tgc cgc acg     2257
Met Gly Ala Asp Ala Arg Asp Ser Val Val Asp Lys Asp Cys Arg Thr
                655                 660                 665

ttc gac cat ccg aac ctg ttc att tcg agc agc gcg acg atg ccg acc     2305
Phe Asp His Pro Asn Leu Phe Ile Ser Ser Ser Ala Thr Met Pro Thr
            670                 675                 680

gtc ggt acc gta aac gtg acg ctg acg atc gcc gcg ctc gcg ctg cgg     2353
Val Gly Thr Val Asn Val Thr Leu Thr Ile Ala Ala Leu Ala Leu Arg
        685                 690                 695

atg tcg gac acg ctg aag aag gaa gtc tgacc gtg cgg aaa tct act ctc   2403
Met Ser Asp Thr Leu Lys Lys Glu Val       Val Arg Lys Ser Thr Leu
    700                 705                     710

act ttc ctc atc gcc ggc tgc ctc gcg ttg ccg ggc ttc gcg cgc gcg     2451
Thr Phe Leu Ile Ala Gly Cys Leu Ala Leu Pro Gly Phe Ala Arg Ala
    715                 720                 725

gcc gat gcg gcc gat ccg gcg ctg gtc aag cgc ggc gaa tac ctc gcg     2499
Ala Asp Ala Ala Asp Pro Ala Leu Val Lys Arg Gly Glu Tyr Leu Ala
```

-continued

```
730                 735                 740                 745

acc gcc ggc gac tgc atg gcc tgc cac acc gtg aag ggc ggc aag ccg      2547
Thr Ala Gly Asp Cys Met Ala Cys His Thr Val Lys Gly Gly Lys Pro
                750                 755                 760

tac gcg ggc ggc ctt ggc atg ccg gta ccg atg ctc ggc aag atc tac      2595
Tyr Ala Gly Gly Leu Gly Met Pro Val Pro Met Leu Gly Lys Ile Tyr
            765                 770                 775

acg agc aac atc acg ccc gat ccc gat acg ggc atc ggc aaa tgg acg      2643
Thr Ser Asn Ile Thr Pro Asp Pro Asp Thr Gly Ile Gly Lys Trp Thr
        780                 785                 790

ttc gag gac ttc gag cgc gcg gtg cgg cac ggc gtg tcg aag aac ggc      2691
Phe Glu Asp Phe Glu Arg Ala Val Arg His Gly Val Ser Lys Asn Gly
    795                 800                 805

gac aac ctg tat ccg gcg atg ccg tac gtg tcg tac gcg aag atc acg      2739
Asp Asn Leu Tyr Pro Ala Met Pro Tyr Val Ser Tyr Ala Lys Ile Thr
810                 815                 820                 825

gac gac gac gta cgc gcg ctg tac gcc tac ttc atg cac ggc gtc gag      2787
Asp Asp Asp Val Arg Ala Leu Tyr Ala Tyr Phe Met His Gly Val Glu
                830                 835                 840

ccg gtc aag cag gcg ccg ccg aag aac gag att ccc gcg ctg ctc agc      2835
Pro Val Lys Gln Ala Pro Pro Lys Asn Glu Ile Pro Ala Leu Leu Ser
            845                 850                 855

atg cgc tgg ccg ctg aag atc tgg aac tgg ctg ttc ctg aag gac ggc      2883
Met Arg Trp Pro Leu Lys Ile Trp Asn Trp Leu Phe Leu Lys Asp Gly
        860                 865                 870

ccg tac cag ccg aag ccg tcg cag agc gcc gaa tgg aat cgc ggc gcg      2931
Pro Tyr Gln Pro Lys Pro Ser Gln Ser Ala Glu Trp Asn Arg Gly Ala
    875                 880                 885

tat ctg gtg cag ggt ctc gcg cac tgc agc acg tgc cac acg ccg cgc      2979
Tyr Leu Val Gln Gly Leu Ala His Cys Ser Thr Cys His Thr Pro Arg
890                 895                 900                 905

ggc atc gcg atg cag gag aag tcg ctc gac gaa acc ggc ggc agc ttc      3027
Gly Ile Ala Met Gln Glu Lys Ser Leu Asp Glu Thr Gly Gly Ser Phe
                910                 915                 920

ctc gcg ggg tcg gtg ctc gcc ggc tgg gac ggc tac aac atc acg tcg      3075
Leu Ala Gly Ser Val Leu Ala Gly Trp Asp Gly Tyr Asn Ile Thr Ser
            925                 930                 935

gac ccg aat gcg ggg atc ggc agc tgg acg cag cag cag ctc gtg cag      3123
Asp Pro Asn Ala Gly Ile Gly Ser Trp Thr Gln Gln Gln Leu Val Gln
        940                 945                 950

tat ttg cgc acc ggc agc gtg ccg ggc gtc gcg cag gcg gcc ggg ccg      3171
Tyr Leu Arg Thr Gly Ser Val Pro Gly Val Ala Gln Ala Ala Gly Pro
    955                 960                 965

atg gcc gag gcg gtc gag cac agc ttc tcg aag atg acc gaa gcg gac      3219
Met Ala Glu Ala Val Glu His Ser Phe Ser Lys Met Thr Glu Ala Asp
970                 975                 980                 985

atc ggt gcg atc gcc acg tac gtc cgc acg gtg ccg gcc gtt gcc  gac     3267
Ile Gly Ala Ile Ala Thr Tyr Val Arg Thr Val Pro Ala Val Ala  Asp
                990                 995                 1000

agc aac gcg aag  cag ccg cgg tcg tcg  tgg ggc aag ccg gcc  gag      3312
Ser Asn Ala Lys  Gln Pro Arg Ser Ser  Trp Gly Lys Pro Ala  Glu
            1005                 1010                 1015

gac ggg ctg aag  ctg cgc ggt gtc gcg  ctc gcg tcg tcg ggc  atc      3357
Asp Gly Leu Lys  Leu Arg Gly Val Ala  Leu Ala Ser Ser Gly  Ile
            1020                 1025                 1030

gat ccg gcg cgg  ctg tat ctc ggc aac  tgc gcg acg tgc cac  cag      3402
Asp Pro Ala Arg  Leu Tyr Leu Gly Asn  Cys Ala Thr Cys His  Gln
            1035                 1040                 1045

atg cag ggc aag  ggc acg ccg gac ggc  tat tac ccg tcg ctg  ttc      3447
```

```
Met Gln Gly Lys  Gly Thr Pro Asp Gly  Tyr Tyr Pro Ser Leu  Phe
            1050                 1055                 1060

cac aac tcc acc  gtc ggc gcg tcg aat  ccg tcg aac ctc gtg  cag      3492
His Asn Ser Thr  Val Gly Ala Ser Asn  Pro Ser Asn Leu Val  Gln
            1065                 1070                 1075

gtg atc ctg aac  ggc gtg cag cgc aag  atc ggc agc gag gat  atc      3537
Val Ile Leu Asn  Gly Val Gln Arg Lys  Ile Gly Ser Glu Asp  Ile
            1080                 1085                 1090

ggg atg ccc gct  ttc cgc tac gat ctg  aac gac gcg cag atc  gcc      3582
Gly Met Pro Ala  Phe Arg Tyr Asp Leu  Asn Asp Ala Gln Ile  Ala
            1095                 1100                 1105

gcg ctg acg aac  tac gtg acc gcg cag  ttc ggc aat ccg gcg  gcg      3627
Ala Leu Thr Asn  Tyr Val Thr Ala Gln  Phe Gly Asn Pro Ala  Ala
            1110                 1115                 1120

aag gtg acg gag  cag gac gtc gcg aag  ctg cgc tgacatagtc            3670
Lys Val Thr Glu  Gln Asp Val Ala Lys  Leu Arg
            1125                 1130

gggcgcgccg acacggcgca accgatagga caggag                             3706


<210> SEQ ID NO 2
<211> LENGTH: 168
<212> TYPE: PRT
<213> ORGANISM: Burkholderia cepacia

<400> SEQUENCE: 2

Met His Asn Asp Asn Thr Pro His Ser Arg Arg His Gly Asp Ala Ala
1               5                   10                  15

Ala Ser Gly Ile Thr Arg Arg Gln Trp Leu Gln Gly Ala Leu Ala Leu
            20                  25                  30

Thr Ala Ala Gly Leu Thr Gly Ser Leu Thr Leu Arg Ala Leu Ala Asp
        35                  40                  45

Asn Pro Gly Thr Ala Pro Leu Asp Thr Phe Met Thr Leu Ser Glu Ser
    50                  55                  60

Leu Thr Gly Lys Lys Gly Leu Ser Arg Val Ile Gly Glu Arg Leu Leu
65                  70                  75                  80

Gln Ala Leu Gln Lys Gly Ser Phe Lys Thr Ala Asp Ser Leu Pro Gln
                85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
        115                 120                 125

Val Val Ile Thr Tyr Glu Glu Ala Leu Met Phe Gly Val Val Ser Asp
    130                 135                 140

Thr Leu Val Ile Arg Ser Tyr Cys Pro Asn Lys Pro Gly Phe Trp Ala
145                 150                 155                 160

Asp Lys Pro Ile Glu Arg Gln Ala
                165


<210> SEQ ID NO 3
<211> LENGTH: 539
<212> TYPE: PRT
<213> ORGANISM: Burkholderia cepacia

<400> SEQUENCE: 3

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30
```

-continued

```
Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445
```

-continued

```
Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535


<210> SEQ ID NO 4
<211> LENGTH: 425
<212> TYPE: PRT
<213> ORGANISM: Burkholderia cepacia

<400> SEQUENCE: 4

Met Arg Lys Ser Thr Leu Thr Phe Leu Ile Ala Gly Cys Leu Ala Leu
1               5                   10                  15

Pro Gly Phe Ala Arg Ala Ala Asp Ala Ala Asp Pro Ala Leu Val Lys
            20                  25                  30

Arg Gly Glu Tyr Leu Ala Thr Ala Gly Asp Cys Met Ala Cys His Thr
        35                  40                  45

Val Lys Gly Gly Lys Pro Tyr Ala Gly Gly Leu Gly Met Pro Val Pro
    50                  55                  60

Met Leu Gly Lys Ile Tyr Thr Ser Asn Ile Thr Pro Asp Pro Asp Thr
65                  70                  75                  80

Gly Ile Gly Lys Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
            100                 105                 110

Ser Tyr Ala Lys Ile Thr Asp Asp Asp Val Arg Ala Leu Tyr Ala Tyr
        115                 120                 125

Phe Met His Gly Val Glu Pro Val Lys Gln Ala Pro Pro Lys Asn Glu
    130                 135                 140

Ile Pro Ala Leu Leu Ser Met Arg Trp Pro Leu Lys Ile Trp Asn Trp
145                 150                 155                 160

Leu Phe Leu Lys Asp Gly Pro Tyr Gln Pro Lys Pro Ser Gln Ser Ala
                165                 170                 175

Glu Trp Asn Arg Gly Ala Tyr Leu Val Gln Gly Leu Ala His Cys Ser
            180                 185                 190

Thr Cys His Thr Pro Arg Gly Ile Ala Met Gln Glu Lys Ser Leu Asp
        195                 200                 205

Glu Thr Gly Gly Ser Phe Leu Ala Gly Ser Val Leu Ala Gly Trp Asp
    210                 215                 220

Gly Tyr Asn Ile Thr Ser Asp Pro Asn Ala Gly Ile Gly Ser Trp Thr
225                 230                 235                 240

Gln Gln Gln Leu Val Gln Tyr Leu Arg Thr Gly Ser Val Pro Gly Val
                245                 250                 255

Ala Gln Ala Ala Gly Pro Met Ala Glu Ala Val Glu His Ser Phe Ser
            260                 265                 270

Lys Met Thr Glu Ala Asp Ile Gly Ala Ile Ala Thr Tyr Val Arg Thr
        275                 280                 285
```

-continued

```
Val Pro Ala Val Ala Asp Ser Asn Ala Lys Gln Pro Arg Ser Ser Trp
    290                 295                 300

Gly Lys Pro Ala Glu Asp Gly Leu Lys Leu Arg Gly Val Ala Leu Ala
305                 310                 315                 320

Ser Ser Gly Ile Asp Pro Ala Arg Leu Tyr Leu Gly Asn Cys Ala Thr
                325                 330                 335

Cys His Gln Met Gln Gly Lys Gly Thr Pro Asp Gly Tyr Tyr Pro Ser
            340                 345                 350

Leu Phe His Asn Ser Thr Val Gly Ala Ser Asn Pro Ser Asn Leu Val
        355                 360                 365

Gln Val Ile Leu Asn Gly Val Gln Arg Lys Ile Gly Ser Glu Asp Ile
    370                 375                 380

Gly Met Pro Ala Phe Arg Tyr Asp Leu Asn Asp Ala Gln Ile Ala Ala
385                 390                 395                 400

Leu Thr Asn Tyr Val Thr Ala Gln Phe Gly Asn Pro Ala Ala Lys Val
                405                 410                 415

Thr Glu Gln Asp Val Ala Lys Leu Arg
            420                 425


<210> SEQ ID NO 5
<211> LENGTH: 3399
<212> TYPE: DNA
<213> ORGANISM: Ewingella americana
<220> FEATURE:
<221> NAME/KEY: CDS
<222> LOCATION: (1)..(507)
<220> FEATURE:
<221> NAME/KEY: CDS
<222> LOCATION: (521)..(2131)
<220> FEATURE:
<221> NAME/KEY: CDS
<222> LOCATION: (2137)..(3396)

<400> SEQUENCE: 5

atg tct gat acc cct tcg aag acg ctt cgc gtc agc ggc gtt tca cgt       48
Met Ser Asp Thr Pro Ser Lys Thr Leu Arg Val Ser Gly Val Ser Arg
1               5                   10                  15

cgt cgc tta ttg ggt tat atc ggc gtc gga ctg gcc agc agc ctg atg       96
Arg Arg Leu Leu Gly Tyr Ile Gly Val Gly Leu Ala Ser Ser Leu Met
            20                  25                  30

atg ccc gtt ccg ctt aaa gcg ttt gcc gcc gac gga gaa cct tcg ccg      144
Met Pro Val Pro Leu Lys Ala Phe Ala Ala Asp Gly Glu Pro Ser Pro
        35                  40                  45

gtt gat gtc gat aaa ttc ttg cgc att tcc cgc gcg cta act ggc aaa      192
Val Asp Val Asp Lys Phe Leu Arg Ile Ser Arg Ala Leu Thr Gly Lys
    50                  55                  60

aag cac ctc aac ccg gtg att ggt caa cgc ctg tat gct gcg att ttg      240
Lys His Leu Asn Pro Val Ile Gly Gln Arg Leu Tyr Ala Ala Ile Leu
65                  70                  75                  80

cag cgc aaa cct gac atc gcc gcg cag ttg gac tca cta caa acc ctg      288
Gln Arg Lys Pro Asp Ile Ala Ala Gln Leu Asp Ser Leu Gln Thr Leu
                85                  90                  95

cct gcc ggt gcg ccg tcg agc tgg tct cag cct cag cag gac gcc gcg      336
Pro Ala Gly Ala Pro Ser Ser Trp Ser Gln Pro Gln Gln Asp Ala Ala
            100                 105                 110

cgc atc atc ctg caa ggc tgg tat ttg ggt cag gtg ggt gag ggg caa      384
Arg Ile Ile Leu Gln Gly Trp Tyr Leu Gly Gln Val Gly Glu Gly Gln
        115                 120                 125

gac att gca gtc gtg act tat gaa aaa gcg ctg atg ttt gag gcg gtc      432
Asp Ile Ala Val Val Thr Tyr Glu Lys Ala Leu Met Phe Glu Ala Val
```

-continued

```
    130                 135                 140

tcc gat gtg ctg gtg atc cgc tct tac tgt acc aat cgt cct ggc tac      480
Ser Asp Val Leu Val Ile Arg Ser Tyr Cys Thr Asn Arg Pro Gly Tyr
145                 150                 155                 160

tgg gct gcc aag ccc gat gtc gcg ctt taattaagga aaa atg aac atg       529
Trp Ala Ala Lys Pro Asp Val Ala Leu                Met Asn Met
                165                                170

gct gac aca tta aaa gct gac gtc gtt gtc att ggc tca ggc gtt gcc      577
Ala Asp Thr Leu Lys Ala Asp Val Val Val Ile Gly Ser Gly Val Ala
        175                 180                 185

ggt ggt tta gtg gca aac gaa ctg gcg aag gcg ggg aaa aac gtc tta      625
Gly Gly Leu Val Ala Asn Glu Leu Ala Lys Ala Gly Lys Asn Val Leu
    190                 195                 200

att ttg gaa gca ggc ccg cgc ctg tct cgc tgg gaa atc gtc gag aat      673
Ile Leu Glu Ala Gly Pro Arg Leu Ser Arg Trp Glu Ile Val Glu Asn
205                 210                 215                 220

ttc cgc aat cag gcc gac aag tcg gac aac atg aag ccg tac ccg tct      721
Phe Arg Asn Gln Ala Asp Lys Ser Asp Asn Met Lys Pro Tyr Pro Ser
                225                 230                 235

acc gac tac gcg ccg cat cct gaa gcg aac cca agc aat aac tat ctg      769
Thr Asp Tyr Ala Pro His Pro Glu Ala Asn Pro Ser Asn Asn Tyr Leu
            240                 245                 250

att cag aag ggt gag cac ccg tac gac gcc cag ttt atc cgc gtg gtg      817
Ile Gln Lys Gly Glu His Pro Tyr Asp Ala Gln Phe Ile Arg Val Val
        255                 260                 265

ggt ggc aca acc tgg cac tgg gcg gcc tcc gcg tgg cgc ttc ctg ccg      865
Gly Gly Thr Thr Trp His Trp Ala Ala Ser Ala Trp Arg Phe Leu Pro
    270                 275                 280

aac gac ttc aag att aaa tct ctg tac ggc gta ggc cgc gac tgg ccg      913
Asn Asp Phe Lys Ile Lys Ser Leu Tyr Gly Val Gly Arg Asp Trp Pro
285                 290                 295                 300

atg gag tac ggc gag ctg gag aaa tgg tac ttc cgc gcc gag caa gag      961
Met Glu Tyr Gly Glu Leu Glu Lys Trp Tyr Phe Arg Ala Glu Gln Glu
                305                 310                 315

ctg ggc gtg tgg ggg cca aac aat gaa gag ctg ggt tcg ccg cgc agt     1009
Leu Gly Val Trp Gly Pro Asn Asn Glu Glu Leu Gly Ser Pro Arg Ser
            320                 325                 330

gcg cca tac ccg atg gaa cct ctg ccg ctc tct tat aac gaa cag cgc     1057
Ala Pro Tyr Pro Met Glu Pro Leu Pro Leu Ser Tyr Asn Glu Gln Arg
        335                 340                 345

ctg aaa acc gtg ctc aac aac aac ggt tac tac gtg gtg acc gag ccg     1105
Leu Lys Thr Val Leu Asn Asn Asn Gly Tyr Tyr Val Val Thr Glu Pro
    350                 355                 360

gtg gcg cgt aac agc cgc cct tat gat ggc cgc ccg acg tgc tgt ggt     1153
Val Ala Arg Asn Ser Arg Pro Tyr Asp Gly Arg Pro Thr Cys Cys Gly
365                 370                 375                 380

aac aac aac tgc atg ccg att tgc ccg att ggc gcg atg tac aac ggc     1201
Asn Asn Asn Cys Met Pro Ile Cys Pro Ile Gly Ala Met Tyr Asn Gly
                385                 390                 395

atc acg cac gtt gag aaa gct gag aaa aac ggc gcc gtg ctg cgc cct     1249
Ile Thr His Val Glu Lys Ala Glu Lys Asn Gly Ala Val Leu Arg Pro
            400                 405                 410

gag tcg gtg gtg tac aag ctg gaa gtc aac gac aag cag gag atc acc     1297
Glu Ser Val Val Tyr Lys Leu Glu Val Asn Asp Lys Gln Glu Ile Thr
        415                 420                 425

gcc gcg ctg ttc aaa gac ccg cag ggc aat gag cac cgc gcc gaa gcc     1345
Ala Ala Leu Phe Lys Asp Pro Gln Gly Asn Glu His Arg Ala Glu Ala
    430                 435                 440

aaa tac ttc gtg ctg gcg gcg aac ggc att gaa atc cct aaa ctg atg     1393
```

-continued

```
Lys Tyr Phe Val Leu Ala Ala Asn Gly Ile Glu Ile Pro Lys Leu Met
445                 450                 455                 460

ctg atg tcc acc aac gac aag aac cct aac ggc gtg ggt aac agc tct     1441
Leu Met Ser Thr Asn Asp Lys Asn Pro Asn Gly Val Gly Asn Ser Ser
                465                 470                 475

gac caa gtg ggc cgt aac ttg atg gac cat ccg ggc gtc ggc gtt gag     1489
Asp Gln Val Gly Arg Asn Leu Met Asp His Pro Gly Val Gly Val Glu
            480                 485                 490

ttc tac gcc aac gag ccg ctg tgg ccg ggg cgc ggg ccg cag gag atg     1537
Phe Tyr Ala Asn Glu Pro Leu Trp Pro Gly Arg Gly Pro Gln Glu Met
        495                 500                 505

acc tct atg gtt ggc ttc cgc gac ggc gat ttc cgt aaa gag tac gcc     1585
Thr Ser Met Val Gly Phe Arg Asp Gly Asp Phe Arg Lys Glu Tyr Ala
    510                 515                 520

gcg aag aaa atc cac ctg tcg aac gtt tcc cgt acc gat cag gaa gca     1633
Ala Lys Lys Ile His Leu Ser Asn Val Ser Arg Thr Asp Gln Glu Ala
525                 530                 535                 540

ggg cgt ctg ctc agc caa aaa ggt gag ttg atc ctt ggg cca gac ctc     1681
Gly Arg Leu Leu Ser Gln Lys Gly Glu Leu Ile Leu Gly Pro Asp Leu
                545                 550                 555

gac aag cgc att cgt gac cgt tcg tcg cgc tac gtg cgt ttt gac agc     1729
Asp Lys Arg Ile Arg Asp Arg Ser Ser Arg Tyr Val Arg Phe Asp Ser
            560                 565                 570

ttc cac gag atc ttg ccg cac gcg gaa aac cgc atc att ccg agt acc     1777
Phe His Glu Ile Leu Pro His Ala Glu Asn Arg Ile Ile Pro Ser Thr
        575                 580                 585

acg gag aaa gac aaa ctg ggc att ccg aag ccg gag ttc tac tac gcg     1825
Thr Glu Lys Asp Lys Leu Gly Ile Pro Lys Pro Glu Phe Tyr Tyr Ala
    590                 595                 600

atg gat gac tac gtg cgt aaa agt gcc gag cac act tac aaa gtc tat     1873
Met Asp Asp Tyr Val Arg Lys Ser Ala Glu His Thr Tyr Lys Val Tyr
605                 610                 615                 620

gcc gat gcg gct cgc ctg atg ggc ggc acc gac atc act tac ttc aaa     1921
Ala Asp Ala Ala Arg Leu Met Gly Gly Thr Asp Ile Thr Tyr Phe Lys
                625                 630                 635

gac ttc gcc aac aac aac cac att acc ggc acc acc atc atg ggc cac     1969
Asp Phe Ala Asn Asn Asn His Ile Thr Gly Thr Thr Ile Met Gly His
            640                 645                 650

gac ccg aaa gac tcg gtg gta gat acc gat tgc cgt act cac gac cac     2017
Asp Pro Lys Asp Ser Val Val Asp Thr Asp Cys Arg Thr His Asp His
        655                 660                 665

aaa aac ctg ttt atc gcc agc agc gcg gtc atg ccg act gtc ggc tcg     2065
Lys Asn Leu Phe Ile Ala Ser Ser Ala Val Met Pro Thr Val Gly Ser
    670                 675                 680

gta aac tgt act ttg act atc gcg gcg ctc tcg ctg cgg att gca gac     2113
Val Asn Cys Thr Leu Thr Ile Ala Ala Leu Ser Leu Arg Ile Ala Asp
685                 690                 695                 700

acg tta aag gcg gag gtg taacc atg aaa aag tta acc ctt agc ctg atg   2163
Thr Leu Lys Ala Glu Val       Met Lys Lys Leu Thr Leu Ser Leu Met
                705                       710                 715

gct gct gtt ggt ctg ttt agc ttg gcg gcg cag gcc gaa gag tct ggc     2211
Ala Ala Val Gly Leu Phe Ser Leu Ala Ala Gln Ala Glu Glu Ser Gly
                720                 725                 730

gtg gac ctg att aag cgc ggt gaa tac ctg acg cag gcc gcg gac tgc     2259
Val Asp Leu Ile Lys Arg Gly Glu Tyr Leu Thr Gln Ala Ala Asp Cys
            735                 740                 745

gtg gcg tgt cac acc act aaa gac ggc aaa cct ttt gcc ggc gga ctg     2307
Val Ala Cys His Thr Thr Lys Asp Gly Lys Pro Phe Ala Gly Gly Leu
        750                 755                 760
```

-continued

```
gct ttt aag acg cca atg ggc acg ctc tac tcg cca aac atc acg gcg     2355
Ala Phe Lys Thr Pro Met Gly Thr Leu Tyr Ser Pro Asn Ile Thr Ala
    765                 770                 775

gat aaa gag acg ggc att ggc act tgg agc gac gag gac ttc ctg cgc     2403
Asp Lys Glu Thr Gly Ile Gly Thr Trp Ser Asp Glu Asp Phe Leu Arg
780                 785                 790                 795

gcg gtt cac gaa ggt aag aac aaa gag ggc cag cac ctc tat ccg gcc     2451
Ala Val His Glu Gly Lys Asn Lys Glu Gly Gln His Leu Tyr Pro Ala
                800                 805                 810

ttc ccg tat acc tct tac acg ctg ttg aaa gat gac gac gtg aag gct     2499
Phe Pro Tyr Thr Ser Tyr Thr Leu Leu Lys Asp Asp Asp Val Lys Ala
            815                 820                 825

atc aag gct tac ttg ttc agc ctg ccg ccg gtg cat cag caa aat cgt     2547
Ile Lys Ala Tyr Leu Phe Ser Leu Pro Pro Val His Gln Gln Asn Arg
        830                 835                 840

gaa aac gag atg ccg ttc ccg ttc aac cag cgc tgg ggc atg tgg ttc     2595
Glu Asn Glu Met Pro Phe Pro Phe Asn Gln Arg Trp Gly Met Trp Phe
    845                 850                 855

tgg aat ctg gtg aat ttc gac agc aag cgt ttt gag cca gac acc gcg     2643
Trp Asn Leu Val Asn Phe Asp Ser Lys Arg Phe Glu Pro Asp Thr Ala
860                 865                 870                 875

cag tct gcc gag tgg aat cag ggt aaa tat ctg gtc gaa ggc tta ggc     2691
Gln Ser Ala Glu Trp Asn Gln Gly Lys Tyr Leu Val Glu Gly Leu Gly
                880                 885                 890

cac tgc ggc gag tgc cat acc ccg cgt aac atc acg atg ggg atg aaa     2739
His Cys Gly Glu Cys His Thr Pro Arg Asn Ile Thr Met Gly Met Lys
            895                 900                 905

gac ggc aag ccg tac gcc gga acc gag gtt gac ggc tgg acc gcg ttt     2787
Asp Gly Lys Pro Tyr Ala Gly Thr Glu Val Asp Gly Trp Thr Ala Phe
        910                 915                 920

aac atc tct tcc gac aag aaa gcc ggg att ggt agc tgg agc aaa ggc     2835
Asn Ile Ser Ser Asp Lys Lys Ala Gly Ile Gly Ser Trp Ser Lys Gly
    925                 930                 935

gac atc gtg cag tat ctg cgt tct ggt cac gtc agt ggc aaa gcg cag     2883
Asp Ile Val Gln Tyr Leu Arg Ser Gly His Val Ser Gly Lys Ala Gln
940                 945                 950                 955

gcc gct ggc ccg atg gcg gaa gtt atc gag aac agt acc cgc cat ctg     2931
Ala Ala Gly Pro Met Ala Glu Val Ile Glu Asn Ser Thr Arg His Leu
                960                 965                 970

acc gat gcc gac ctg aac gcg atg gcg acc tac atc cag acg ctg aag     2979
Thr Asp Ala Asp Leu Asn Ala Met Ala Thr Tyr Ile Gln Thr Leu Lys
            975                 980                 985

ccg cag gca gat tct tcc gtc acc aag agc cgt tct gat  tgg ggc cat    3027
Pro Gln Ala Asp Ser Ser Val Thr Lys Ser Arg Ser Asp  Trp Gly His
        990                 995                 1000

gag agc  acc agc gta gac aac  ctg cgc ggc gtg cca  ttc aaa gcc     3072
Glu Ser  Thr Ser Val Asp Asn  Leu Arg Gly Val Pro  Phe Lys Ala
    1005                 1010                 1015

agc caa  gaa acc gac ggc gcg  cgt ttg ttc ctc ggc  aac tgc gca     3117
Ser Gln  Glu Thr Asp Gly Ala  Arg Leu Phe Leu Gly  Asn Cys Ala
    1020                 1025                 1030

agc tgc  cac agc ttc ggc ggt  cag ggc agc caa gac  ggt tac tac     3162
Ser Cys  His Ser Phe Gly Gly  Gln Gly Ser Gln Asp  Gly Tyr Tyr
    1035                 1040                 1045

cca tcg  ctg atg aaa aac agc  gtg gtg ggt gcc cag  aca cca aac     3207
Pro Ser  Leu Met Lys Asn Ser  Val Val Gly Ala Gln  Thr Pro Asn
    1050                 1055                 1060

aac ttg  gtc aac gtt atc ctg  cac ggc gta tcg cgc  aag acc aac     3252
Asn Leu  Val Asn Val Ile Leu  His Gly Val Ser Arg  Lys Thr Asn
    1065                 1070                 1075
```

-continued

```
gac ggc  gaa gtg ttc atg ccg  ggc ttt gcc gac acc  ctg agc gac      3297
Asp Gly  Glu Val Phe Met Pro  Gly Phe Ala Asp Thr  Leu Ser Asp
    1080                 1085                 1090

aag cag  atc gcc acg ctg agc  acc tat atg ttt aaa  gag ttt ggc      3342
Lys Gln  Ile Ala Thr Leu Ser  Thr Tyr Met Phe Lys  Glu Phe Gly
    1095                 1100                 1105

gcc cag  ccg gtg ttg aat gtg  aaa gat aaa gat gtg  aag gat ttg      3387
Ala Gln  Pro Val Leu Asn Val  Lys Asp Lys Asp Val  Lys Asp Leu
    1110                 1115                 1120

cgc ggg  gag tga                                                    3399
Arg Gly  Glu
    1125


<210> SEQ ID NO 6
<211> LENGTH: 169
<212> TYPE: PRT
<213> ORGANISM: Ewingella americana

<400> SEQUENCE: 6

Met Ser Asp Thr Pro Ser Lys Thr Leu Arg Val Ser Gly Val Ser Arg
1               5                   10                  15

Arg Arg Leu Leu Gly Tyr Ile Gly Val Gly Leu Ala Ser Ser Leu Met
            20                  25                  30

Met Pro Val Pro Leu Lys Ala Phe Ala Ala Asp Gly Glu Pro Ser Pro
        35                  40                  45

Val Asp Val Asp Lys Phe Leu Arg Ile Ser Arg Ala Leu Thr Gly Lys
    50                  55                  60

Lys His Leu Asn Pro Val Ile Gly Gln Arg Leu Tyr Ala Ala Ile Leu
65                  70                  75                  80

Gln Arg Lys Pro Asp Ile Ala Ala Gln Leu Asp Ser Leu Gln Thr Leu
                85                  90                  95

Pro Ala Gly Ala Pro Ser Ser Trp Ser Gln Pro Gln Gln Asp Ala Ala
            100                 105                 110

Arg Ile Ile Leu Gln Gly Trp Tyr Leu Gly Gln Val Gly Glu Gly Gln
        115                 120                 125

Asp Ile Ala Val Val Thr Tyr Glu Lys Ala Leu Met Phe Glu Ala Val
    130                 135                 140

Ser Asp Val Leu Val Ile Arg Ser Tyr Cys Thr Asn Arg Pro Gly Tyr
145                 150                 155                 160

Trp Ala Ala Lys Pro Asp Val Ala Leu
                165


<210> SEQ ID NO 7
<211> LENGTH: 537
<212> TYPE: PRT
<213> ORGANISM: Ewingella americana

<400> SEQUENCE: 7

Met Asn Met Ala Asp Thr Leu Lys Ala Asp Val Val Val Ile Gly Ser
1               5                   10                  15

Gly Val Ala Gly Gly Leu Val Ala Asn Glu Leu Ala Lys Ala Gly Lys
            20                  25                  30

Asn Val Leu Ile Leu Glu Ala Gly Pro Arg Leu Ser Arg Trp Glu Ile
        35                  40                  45

Val Glu Asn Phe Arg Asn Gln Ala Asp Lys Ser Asp Asn Met Lys Pro
    50                  55                  60

Tyr Pro Ser Thr Asp Tyr Ala Pro His Pro Glu Ala Asn Pro Ser Asn
```

-continued

```
65                  70                  75                  80

Asn Tyr Leu Ile Gln Lys Gly Glu His Pro Tyr Asp Ala Gln Phe Ile
                85                  90                  95

Arg Val Val Gly Gly Thr Thr Trp His Trp Ala Ala Ser Ala Trp Arg
            100                 105                 110

Phe Leu Pro Asn Asp Phe Lys Ile Lys Ser Leu Tyr Gly Val Gly Arg
        115                 120                 125

Asp Trp Pro Met Glu Tyr Gly Glu Leu Glu Lys Trp Tyr Phe Arg Ala
    130                 135                 140

Glu Gln Glu Leu Gly Val Trp Gly Pro Asn Asn Glu Glu Leu Gly Ser
145                 150                 155                 160

Pro Arg Ser Ala Pro Tyr Pro Met Glu Pro Leu Pro Leu Ser Tyr Asn
                165                 170                 175

Glu Gln Arg Leu Lys Thr Val Leu Asn Asn Asn Gly Tyr Tyr Val Val
            180                 185                 190

Thr Glu Pro Val Ala Arg Asn Ser Arg Pro Tyr Asp Gly Arg Pro Thr
        195                 200                 205

Cys Cys Gly Asn Asn Asn Cys Met Pro Ile Cys Pro Ile Gly Ala Met
    210                 215                 220

Tyr Asn Gly Ile Thr His Val Glu Lys Ala Glu Lys Asn Gly Ala Val
225                 230                 235                 240

Leu Arg Pro Glu Ser Val Val Tyr Lys Leu Glu Val Asn Asp Lys Gln
                245                 250                 255

Glu Ile Thr Ala Ala Leu Phe Lys Asp Pro Gln Gly Asn Glu His Arg
            260                 265                 270

Ala Glu Ala Lys Tyr Phe Val Leu Ala Ala Asn Gly Ile Glu Ile Pro
        275                 280                 285

Lys Leu Met Leu Met Ser Thr Asn Asp Lys Asn Pro Asn Gly Val Gly
    290                 295                 300

Asn Ser Ser Asp Gln Val Gly Arg Asn Leu Met Asp His Pro Gly Val
305                 310                 315                 320

Gly Val Glu Phe Tyr Ala Asn Glu Pro Leu Trp Pro Gly Arg Gly Pro
                325                 330                 335

Gln Glu Met Thr Ser Met Val Gly Phe Arg Asp Gly Asp Phe Arg Lys
            340                 345                 350

Glu Tyr Ala Ala Lys Lys Ile His Leu Ser Asn Val Ser Arg Thr Asp
        355                 360                 365

Gln Glu Ala Gly Arg Leu Leu Ser Gln Lys Gly Glu Leu Ile Leu Gly
    370                 375                 380

Pro Asp Leu Asp Lys Arg Ile Arg Asp Arg Ser Ser Arg Tyr Val Arg
385                 390                 395                 400

Phe Asp Ser Phe His Glu Ile Leu Pro His Ala Glu Asn Arg Ile Ile
                405                 410                 415

Pro Ser Thr Thr Glu Lys Asp Lys Leu Gly Ile Pro Lys Pro Glu Phe
            420                 425                 430

Tyr Tyr Ala Met Asp Asp Tyr Val Arg Lys Ser Ala Glu His Thr Tyr
        435                 440                 445

Lys Val Tyr Ala Asp Ala Ala Arg Leu Met Gly Gly Thr Asp Ile Thr
    450                 455                 460

Tyr Phe Lys Asp Phe Ala Asn Asn Asn His Ile Thr Gly Thr Thr Ile
465                 470                 475                 480

Met Gly His Asp Pro Lys Asp Ser Val Val Asp Thr Asp Cys Arg Thr
                485                 490                 495
```

```
His Asp His Lys Asn Leu Phe Ile Ala Ser Ser Ala Val Met Pro Thr
            500                 505                 510

Val Gly Ser Val Asn Cys Thr Leu Thr Ile Ala Ala Leu Ser Leu Arg
        515                 520                 525

Ile Ala Asp Thr Leu Lys Ala Glu Val
    530                 535


<210> SEQ ID NO 8
<211> LENGTH: 420
<212> TYPE: PRT
<213> ORGANISM: Ewingella americana

<400> SEQUENCE: 8

Met Lys Lys Leu Thr Leu Ser Leu Met Ala Ala Val Gly Leu Phe Ser
1               5                   10                  15

Leu Ala Ala Gln Ala Glu Glu Ser Gly Val Asp Leu Ile Lys Arg Gly
            20                  25                  30

Glu Tyr Leu Thr Gln Ala Ala Asp Cys Val Ala Cys His Thr Thr Lys
        35                  40                  45

Asp Gly Lys Pro Phe Ala Gly Gly Leu Ala Phe Lys Thr Pro Met Gly
    50                  55                  60

Thr Leu Tyr Ser Pro Asn Ile Thr Ala Asp Lys Glu Thr Gly Ile Gly
65                  70                  75                  80

Thr Trp Ser Asp Glu Asp Phe Leu Arg Ala Val His Glu Gly Lys Asn
                85                  90                  95

Lys Glu Gly Gln His Leu Tyr Pro Ala Phe Pro Tyr Thr Ser Tyr Thr
            100                 105                 110

Leu Leu Lys Asp Asp Asp Val Lys Ala Ile Lys Ala Tyr Leu Phe Ser
        115                 120                 125

Leu Pro Pro Val His Gln Gln Asn Arg Glu Asn Glu Met Pro Phe Pro
    130                 135                 140

Phe Asn Gln Arg Trp Gly Met Trp Phe Trp Asn Leu Val Asn Phe Asp
145                 150                 155                 160

Ser Lys Arg Phe Glu Pro Asp Thr Ala Gln Ser Ala Glu Trp Asn Gln
                165                 170                 175

Gly Lys Tyr Leu Val Glu Gly Leu Gly His Cys Gly Glu Cys His Thr
            180                 185                 190

Pro Arg Asn Ile Thr Met Gly Met Lys Asp Gly Lys Pro Tyr Ala Gly
        195                 200                 205

Thr Glu Val Asp Gly Trp Thr Ala Phe Asn Ile Ser Ser Asp Lys Lys
    210                 215                 220

Ala Gly Ile Gly Ser Trp Ser Lys Gly Asp Ile Val Gln Tyr Leu Arg
225                 230                 235                 240

Ser Gly His Val Ser Gly Lys Ala Gln Ala Ala Gly Pro Met Ala Glu
                245                 250                 255

Val Ile Glu Asn Ser Thr Arg His Leu Thr Asp Ala Asp Leu Asn Ala
            260                 265                 270

Met Ala Thr Tyr Ile Gln Thr Leu Lys Pro Gln Ala Asp Ser Ser Val
        275                 280                 285

Thr Lys Ser Arg Ser Asp Trp Gly His Glu Ser Thr Ser Val Asp Asn
    290                 295                 300

Leu Arg Gly Val Pro Phe Lys Ala Ser Gln Glu Thr Asp Gly Ala Arg
305                 310                 315                 320

Leu Phe Leu Gly Asn Cys Ala Ser Cys His Ser Phe Gly Gly Gln Gly
```

```
                325                 330                 335

Ser Gln Asp Gly Tyr Tyr Pro Ser Leu Met Lys Asn Ser Val Val Gly
            340                 345                 350

Ala Gln Thr Pro Asn Asn Leu Val Asn Val Ile Leu His Gly Val Ser
        355                 360                 365

Arg Lys Thr Asn Asp Gly Glu Val Phe Met Pro Gly Phe Ala Asp Thr
    370                 375                 380

Leu Ser Asp Lys Gln Ile Ala Thr Leu Ser Thr Tyr Met Phe Lys Glu
385                 390                 395                 400

Phe Gly Ala Gln Pro Val Leu Asn Val Lys Asp Lys Asp Val Lys Asp
                405                 410                 415

Leu Arg Gly Glu
            420


<210> SEQ ID NO 9
<211> LENGTH: 26
<212> TYPE: DNA
<213> ORGANISM: artificial sequence
<220> FEATURE:
<223> OTHER INFORMATION: primer

<400> SEQUENCE: 9

catgccatgg cacacaacga caacac                                          26


<210> SEQ ID NO 10
<211> LENGTH: 30
<212> TYPE: DNA
<213> ORGANISM: artificial sequence
<220> FEATURE:
<223> OTHER INFORMATION: primer

<400> SEQUENCE: 10

gtcgacgatc ttcttccagc cgaacatcac                                      30


<210> SEQ ID NO 11
<211> LENGTH: 3638
<212> TYPE: DNA
<213> ORGANISM: Silvimonas terrae
<220> FEATURE:
<221> NAME/KEY: CDS
<222> LOCATION: (1)..(537)
<220> FEATURE:
<221> NAME/KEY: CDS
<222> LOCATION: (555)..(2174)
<220> FEATURE:
<221> NAME/KEY: CDS
<222> LOCATION: (2193)..(3635)

<400> SEQUENCE: 11

atg aat gat cgt gat tcg ccc att cac gcc gat gcg cta ctc ccc cag       48
Met Asn Asp Arg Asp Ser Pro Ile His Ala Asp Ala Leu Leu Pro Gln
1               5                   10                  15

ccc acc cgc cgc cgt ctg ttg ctg gca tct ggc ttg ctg ctg ggg acg       96
Pro Thr Arg Arg Arg Leu Leu Leu Ala Ser Gly Leu Leu Leu Gly Thr
            20                  25                  30

ctg gcc gtt tcc ggg cga ctg gtc tcg gtg gtc ttt gcc gat acg cct      144
Leu Ala Val Ser Gly Arg Leu Val Ser Val Val Phe Ala Asp Thr Pro
        35                  40                  45

gcg caa gac agc cag ttt ttg cag ctc tcg caa tta ctg acc ggg cgg      192
Ala Gln Asp Ser Gln Phe Leu Gln Leu Ser Gln Leu Leu Thr Gly Arg
    50                  55                  60

gcg caa ctg gat acc gcc gtc gca cac cgt ttt tat tca gcg ctg agc      240
Ala Gln Leu Asp Thr Ala Val Ala His Arg Phe Tyr Ser Ala Leu Ser
```

-continued

```
65                  70                  75                  80

acc aaa gac aat cag ctg gac agc aag ctg cgg cag att gcg ggc gaa      288
Thr Lys Asp Asn Gln Leu Asp Ser Lys Leu Arg Gln Ile Ala Gly Glu
                85                  90                  95

gcg caa acc aac agc ctg acc aat gcc gaa gaa ttg ctc acc gcg ctg      336
Ala Gln Thr Asn Ser Leu Thr Asn Ala Glu Glu Leu Leu Thr Ala Leu
            100                 105                 110

gat gcc aac cag cca gaa ctg gcc aag acc gcg cgc aac atc att gcc      384
Asp Ala Asn Gln Pro Glu Leu Ala Lys Thr Ala Arg Asn Ile Ile Ala
        115                 120                 125

gcg tgg tat tcc ggt gtg gtg ggt gac ggc ccg gat gcc att gtg att      432
Ala Trp Tyr Ser Gly Val Val Gly Asp Gly Pro Asp Ala Ile Val Ile
    130                 135                 140

act tat gcc agc gcc ttg atg ttc gat ctg gtc aaa gac gcc acc atg      480
Thr Tyr Ala Ser Ala Leu Met Phe Asp Leu Val Lys Asp Ala Thr Met
145                 150                 155                 160

ccg ccc tct tac tgc cag gcc gca ccg ctg tac tgg tcg gcc aaa cca      528
Pro Pro Ser Tyr Cys Gln Ala Ala Pro Leu Tyr Trp Ser Ala Lys Pro
                165                 170                 175

ccg ctg aac tgacccggac cctcttc atg agc gca aac aat caa tct gcg       578
Pro Leu Asn                     Met Ser Ala Asn Asn Gln Ser Ala
                                180                 185

gat gtc att gtc att ggt tca ggg gta gcc ggt gcg ctg gtg gcg cat      626
Asp Val Ile Val Ile Gly Ser Gly Val Ala Gly Ala Leu Val Ala His
        190                 195                 200

gat ctc tct gcc gcc ggg gcg tca gtg ctg atg ctg gaa gcc ggc ccc      674
Asp Leu Ser Ala Ala Gly Ala Ser Val Leu Met Leu Glu Ala Gly Pro
    205                 210                 215

cgg ctg gaa cgc tgg cgc att gtc gaa aac tac cgc aat ggc gcc gcc      722
Arg Leu Glu Arg Trp Arg Ile Val Glu Asn Tyr Arg Asn Gly Ala Ala
220                 225                 230                 235

aaa gat gat aac cag cgc ccc tac ccg gcc gcc aga cac gcg ccg cac      770
Lys Asp Asp Asn Gln Arg Pro Tyr Pro Ala Ala Arg His Ala Pro His
                240                 245                 250

ccg gaa tac ggg ccc gac aac aac tat ctg atc ctc aaa ggc ccg gat      818
Pro Glu Tyr Gly Pro Asp Asn Asn Tyr Leu Ile Leu Lys Gly Pro Asp
            255                 260                 265

gcg cag tct tat gcc tcg caa tat ctg cgg gtc gtt ggc ggc acc acc      866
Ala Gln Ser Tyr Ala Ser Gln Tyr Leu Arg Val Val Gly Gly Thr Thr
        270                 275                 280

tgg cac tgg gcc gcg tcc tgt tgg cgc ttt ctg ccc aat gat ttt cat      914
Trp His Trp Ala Ala Ser Cys Trp Arg Phe Leu Pro Asn Asp Phe His
    285                 290                 295

atg aag cag gtc tac ggc gtg ggc cgg gac tgg ggg atc agc tat gcc      962
Met Lys Gln Val Tyr Gly Val Gly Arg Asp Trp Gly Ile Ser Tyr Ala
300                 305                 310                 315

gat ctg gaa ccc tgg tac tac aag gcc gag ctg gaa ctc ggg gtt tcc     1010
Asp Leu Glu Pro Trp Tyr Tyr Lys Ala Glu Leu Glu Leu Gly Val Ser
                320                 325                 330

ggg ccc aac gac ggc aca gac ctg ggc tca ccg cgc aag cag ccc tac     1058
Gly Pro Asn Asp Gly Thr Asp Leu Gly Ser Pro Arg Lys Gln Pro Tyr
            335                 340                 345

ccg atg gat cac ctg ccg ctg tct tac aac gac cag cgg ttc cac gat     1106
Pro Met Asp His Leu Pro Leu Ser Tyr Asn Asp Gln Arg Phe His Asp
        350                 355                 360

gtc ctc aac gcc aac ggg ttc aat ctg gtg gcc gaa ccg gtg gcc cgc     1154
Val Leu Asn Ala Asn Gly Phe Asn Leu Val Ala Glu Pro Val Ala Arg
    365                 370                 375

aac agc cgg ccc tac gac gag cgc ccg acg tgc tgt ggc aac aac aac     1202
```

-continued

```
Asn Ser Arg Pro Tyr Asp Glu Arg Pro Thr Cys Cys Gly Asn Asn Asn
380                 385                 390                 395

tgc atg ccc atc tgc ccg att gcc gcc atg tac agc ggc atc atc cat      1250
Cys Met Pro Ile Cys Pro Ile Ala Ala Met Tyr Ser Gly Ile Ile His
                400                 405                 410

gtg ctc aaa gcc gaa cgc gcg ggt acg cga ttg ctg acc aat gcg gtg      1298
Val Leu Lys Ala Glu Arg Ala Gly Thr Arg Leu Leu Thr Asn Ala Val
            415                 420                 425

gtg tac cgg ctg gaa gta gac gct cac gac aac atc att gct gcg ctc      1346
Val Tyr Arg Leu Glu Val Asp Ala His Asp Asn Ile Ile Ala Ala Leu
        430                 435                 440

tac aaa gac ccg gac ggc aac agt cat cgg gtc acc ggc aag tat ttc      1394
Tyr Lys Asp Pro Asp Gly Asn Ser His Arg Val Thr Gly Lys Tyr Phe
    445                 450                 455

gtg ctg gcg gcc aat gcc ctg gaa tca gcc aaa atc ctg ttg atg tcg      1442
Val Leu Ala Ala Asn Ala Leu Glu Ser Ala Lys Ile Leu Leu Met Ser
460                 465                 470                 475

acc acc gac aaa ttt gcc agt ggc ctg gcc aac agt tca gac cag gta      1490
Thr Thr Asp Lys Phe Ala Ser Gly Leu Ala Asn Ser Ser Asp Gln Val
                480                 485                 490

ggc cgt aat ctg atg gat cac ccc ggc act ggc ata acc ttt ctg gcc      1538
Gly Arg Asn Leu Met Asp His Pro Gly Thr Gly Ile Thr Phe Leu Ala
            495                 500                 505

aat gag ccg ctc tgg ccg ggc cgc ggg ccg atg gag ctg acc tcg att      1586
Asn Glu Pro Leu Trp Pro Gly Arg Gly Pro Met Glu Leu Thr Ser Ile
        510                 515                 520

gtc gat cac cgc gac ggg gat ttc cgg cgg gag tgg gcc agc aag aag      1634
Val Asp His Arg Asp Gly Asp Phe Arg Arg Glu Trp Ala Ser Lys Lys
    525                 530                 535

ttg cac ctc aat aac cag tcc cag acg cgc aag gcc aca gaa aaa gcc      1682
Leu His Leu Asn Asn Gln Ser Gln Thr Arg Lys Ala Thr Glu Lys Ala
540                 545                 550                 555

ttg tcg atg ggg ctg gtg ggc aag aag ctg gat gaa gaa atc cgc tac      1730
Leu Ser Met Gly Leu Val Gly Lys Lys Leu Asp Glu Glu Ile Arg Tyr
                560                 565                 570

cgg gcc gcg cat acg gtc aac atc aac agt ttt cat gac att ttg ccg      1778
Arg Ala Ala His Thr Val Asn Ile Asn Ser Phe His Asp Ile Leu Pro
            575                 580                 585

gag ccg gac aac cgc ctc gtc ctg tca gac cag aaa gac ccg ctg ggc      1826
Glu Pro Asp Asn Arg Leu Val Leu Ser Asp Gln Lys Asp Pro Leu Gly
        590                 595                 600

ctg ccc cgc atg gaa atc acc tac aag att ggg gat tac acc aag cgc      1874
Leu Pro Arg Met Glu Ile Thr Tyr Lys Ile Gly Asp Tyr Thr Lys Arg
    605                 610                 615

agc gcc gaa cat acg cat gag tcc tac gca aaa att gcc cag ttg ttt      1922
Ser Ala Glu His Thr His Glu Ser Tyr Ala Lys Ile Ala Gln Leu Phe
620                 625                 630                 635

ggc ggg acc gag gtg acg ttt gat gac aaa ttt gcc ccc aac aat cac      1970
Gly Gly Thr Glu Val Thr Phe Asp Asp Lys Phe Ala Pro Asn Asn His
                640                 645                 650

ctg atg ggc tcg gtc atc atg gga caa aac ccc aaa gac tcg gtg gtc      2018
Leu Met Gly Ser Val Ile Met Gly Gln Asn Pro Lys Asp Ser Val Val
            655                 660                 665

gat ggc gat tgt cgc gcg cac gac cac gcc aat ctg tat ctg gct acc      2066
Asp Gly Asp Cys Arg Ala His Asp His Ala Asn Leu Tyr Leu Ala Thr
        670                 675                 680

agc ggg gtg atg gcg tcg gcc ggc agt gtg aac tgc acg ctg acc atc      2114
Ser Gly Val Met Ala Ser Ala Gly Ser Val Asn Cys Thr Leu Thr Ile
    685                 690                 695
```

-continued

```
gcc gcg ctg tcc ttg cgt att gcc gac acg ctc aag cgc cag ctt ggg     2162
Ala Ala Leu Ser Leu Arg Ile Ala Asp Thr Leu Lys Arg Gln Leu Gly
700                 705                 710                 715

cgc acc acc agt taagacggga gcgctacc atg acc tgc cgt ctt ctt cgc     2213
Arg Thr Thr Ser                     Met Thr Cys Arg Leu Leu Arg
                                    720                 725

ccc ttt gcc ctt gcg gcc ctg atg ctt gtt tct gcg ctg gcg cag gct     2261
Pro Phe Ala Leu Ala Ala Leu Met Leu Val Ser Ala Leu Ala Gln Ala
            730                 735                 740

gct gag gtc agc ccg gaa cag atc aag cgc ggc gag tat ctg gcc cgc     2309
Ala Glu Val Ser Pro Glu Gln Ile Lys Arg Gly Glu Tyr Leu Ala Arg
        745                 750                 755

gcc gcc gac tgt att gcc tgt cat acc gtg ccg cgt acc ggc cag ccg     2357
Ala Ala Asp Cys Ile Ala Cys His Thr Val Pro Arg Thr Gly Gln Pro
    760                 765                 770

ttt gcg ggt ggt tac ggc att gcc tcg ccg ttg ggc act att tat tcg     2405
Phe Ala Gly Gly Tyr Gly Ile Ala Ser Pro Leu Gly Thr Ile Tyr Ser
775                 780                 785                 790

tcc aac atc acg ccg tcc act tcg gcc ggg att ggc aac tac acg cta     2453
Ser Asn Ile Thr Pro Ser Thr Ser Ala Gly Ile Gly Asn Tyr Thr Leu
                795                 800                 805

caa gat ttc gac aac gcc ttg cgc cgg ggc atc cgc aaa gat ggc gcg     2501
Gln Asp Phe Asp Asn Ala Leu Arg Arg Gly Ile Arg Lys Asp Gly Ala
            810                 815                 820

cac ctc tac ccg gcc atg ccc tac acc gcc tac gcc aag ctg cag cca     2549
His Leu Tyr Pro Ala Met Pro Tyr Thr Ala Tyr Ala Lys Leu Gln Pro
        825                 830                 835

gaa gac gtc gag gcg ctc tat gcc tat ctg atg cat ggc gtg aaa ccg     2597
Glu Asp Val Glu Ala Leu Tyr Ala Tyr Leu Met His Gly Val Lys Pro
    840                 845                 850

gta gat gcc cag cca cgt cgc acg cgg ttg ccg ttt ccg ttc aac atc     2645
Val Asp Ala Gln Pro Arg Arg Thr Arg Leu Pro Phe Pro Phe Asn Ile
855                 860                 865                 870

cgg ctc tcc atg gcc gtc tgg aac agc ttg ttt ctg gac cca cgg gtt     2693
Arg Leu Ser Met Ala Val Trp Asn Ser Leu Phe Leu Asp Pro Arg Val
                875                 880                 885

ttc cag cca gaa caa ggc aag agt gag gac ttc aat cgc ggc aag tat     2741
Phe Gln Pro Glu Gln Gly Lys Ser Glu Asp Phe Asn Arg Gly Lys Tyr
            890                 895                 900

ctg gta gaa gca ctg gaa cat tgc agc gcc tgc cac acg ccc cgc aac     2789
Leu Val Glu Ala Leu Glu His Cys Ser Ala Cys His Thr Pro Arg Asn
        905                 910                 915

atg ctg atg gca gaa aac ccg gac gcg cca ttt gcc ggc ggg caa ctg     2837
Met Leu Met Ala Glu Asn Pro Asp Ala Pro Phe Ala Gly Gly Gln Leu
    920                 925                 930

ggt gca tgg tat gcg ccc aat atc acc gcc gac ccc gtc agc ggc gtt     2885
Gly Ala Trp Tyr Ala Pro Asn Ile Thr Ala Asp Pro Val Ser Gly Val
935                 940                 945                 950

ggc ggc tgg acc cag gcg gaa ctg gtg caa tac ctc aaa acc ggc cat     2933
Gly Gly Trp Thr Gln Ala Glu Leu Val Gln Tyr Leu Lys Thr Gly His
                955                 960                 965

gtc gcg ggc aaa gct gcg gcc gcc ggc ccg atg gcc gaa gcg gtc tct     2981
Val Ala Gly Lys Ala Ala Ala Ala Gly Pro Met Ala Glu Ala Val Ser
            970                 975                 980

gac agc tta agc cat ctg acc gac cca gac ctg cag gcc atg gcg acc     3029
Asp Ser Leu Ser His Leu Thr Asp Pro Asp Leu Gln Ala Met Ala Thr
        985                 990                 995

tac ctc  aaa acc atc gcc ccc  atc cgc aat acc gcc  gac agc aaa     3074
Tyr Leu  Lys Thr Ile Ala Pro  Ile Arg Asn Thr Ala  Asp Ser Lys
    1000                 1005                 1010
```

```
ccc gcc  tgg gca tgg ggt agc  ccg gcc aat gac gac  gat agc ttg      3119
Pro Ala  Trp Ala Trp Gly Ser  Pro Ala Asn Asp Asp  Asp Ser Leu
    1015                 1020                 1025

cgc ggt  acg gcg ggc gtc acc  caa agt aac cgc cca  acc agc gcg      3164
Arg Gly  Thr Ala Gly Val Thr  Gln Ser Asn Arg Pro  Thr Ser Ala
    1030                 1035                 1040

gcc gaa  ttg ttc agc gcc aat  tgc gcc agt tgc cat  caa gcc aat      3209
Ala Glu  Leu Phe Ser Ala Asn  Cys Ala Ser Cys His  Gln Ala Asn
    1045                 1050                 1055

ggc atg  ggc acg acc gac acc  gcc tac cca tcg ctc  acc aac aac      3254
Gly Met  Gly Thr Thr Asp Thr  Ala Tyr Pro Ser Leu  Thr Asn Asn
    1060                 1065                 1070

acg gcg  ttg gga cac ctt aac  ccc agc aac ctg atc  gcc gta atc      3299
Thr Ala  Leu Gly His Leu Asn  Pro Ser Asn Leu Ile  Ala Val Ile
    1075                 1080                 1085

ctg aac  ggg gta gac cgg cca  ctg ccg gac ggc cac  cac gcc ttc      3344
Leu Asn  Gly Val Asp Arg Pro  Leu Pro Asp Gly His  His Ala Phe
    1090                 1095                 1100

atg cct  ggt ttt ggc ccc ggc  agc ctg atc aac ccc  ttg tcg gat      3389
Met Pro  Gly Phe Gly Pro Gly  Ser Leu Ile Asn Pro  Leu Ser Asp
    1105                 1110                 1115

gcg gat  atc gcc acg ctg gcc  aat tac acg ttg caa  cgg ttc ggc      3434
Ala Asp  Ile Ala Thr Leu Ala  Asn Tyr Thr Leu Gln  Arg Phe Gly
    1120                 1125                 1130

aac acc  aac gtc cac gtc acg  ccc gag gag gtc gct  gcc tcg cga      3479
Asn Thr  Asn Val His Val Thr  Pro Glu Glu Val Ala  Ala Ser Arg
    1135                 1140                 1145

aaa ggc  ggt gag ccg cca ctg  ctc gcc aaa ttg ccc  cgt gta ttg      3524
Lys Gly  Gly Glu Pro Pro Leu  Leu Ala Lys Leu Pro  Arg Val Leu
    1150                 1155                 1160

ccg gtc  gtg ctg atg ctg ttt  gcg ctg ttg ctg att  ctg ggc ggc      3569
Pro Val  Val Leu Met Leu Phe  Ala Leu Leu Leu Ile  Leu Gly Gly
    1165                 1170                 1175

tgg cgc  agt gcg cga cag cgc  aaa ttg cgc cat gta  gcg cgc ccc      3614
Trp Arg  Ser Ala Arg Gln Arg  Lys Leu Arg His Val  Ala Arg Pro
    1180                 1185                 1190

tct ccc  acg cca cgc acg cct  tga                                  3638
Ser Pro  Thr Pro Arg Thr Pro
    1195                 1200


<210> SEQ ID NO 12
<211> LENGTH: 179
<212> TYPE: PRT
<213> ORGANISM: Silvimonas terrae

<400> SEQUENCE: 12

Met Asn Asp Arg Asp Ser Pro Ile His Ala Asp Ala Leu Leu Pro Gln
1               5                   10                  15

Pro Thr Arg Arg Arg Leu Leu Leu Ala Ser Gly Leu Leu Leu Gly Thr
            20                  25                  30

Leu Ala Val Ser Gly Arg Leu Val Ser Val Val Phe Ala Asp Thr Pro
        35                  40                  45

Ala Gln Asp Ser Gln Phe Leu Gln Leu Ser Gln Leu Leu Thr Gly Arg
    50                  55                  60

Ala Gln Leu Asp Thr Ala Val Ala His Arg Phe Tyr Ser Ala Leu Ser
65                  70                  75                  80

Thr Lys Asp Asn Gln Leu Asp Ser Lys Leu Arg Gln Ile Ala Gly Glu
                85                  90                  95
```

-continued

```
Ala Gln Thr Asn Ser Leu Thr Asn Ala Glu Glu Leu Leu Thr Ala Leu
            100                 105                 110

Asp Ala Asn Gln Pro Glu Leu Ala Lys Thr Ala Arg Asn Ile Ile Ala
        115                 120                 125

Ala Trp Tyr Ser Gly Val Val Gly Asp Gly Pro Asp Ala Ile Val Ile
    130                 135                 140

Thr Tyr Ala Ser Ala Leu Met Phe Asp Leu Val Lys Asp Ala Thr Met
145                 150                 155                 160

Pro Pro Ser Tyr Cys Gln Ala Ala Pro Leu Tyr Trp Ser Ala Lys Pro
                165                 170                 175

Pro Leu Asn


<210> SEQ ID NO 13
<211> LENGTH: 540
<212> TYPE: PRT
<213> ORGANISM: Silvimonas terrae

<400> SEQUENCE: 13

Met Ser Ala Asn Asn Gln Ser Ala Asp Val Ile Val Ile Gly Ser Gly
1               5                   10                  15

Val Ala Gly Ala Leu Val Ala His Asp Leu Ser Ala Ala Gly Ala Ser
            20                  25                  30

Val Leu Met Leu Glu Ala Gly Pro Arg Leu Glu Arg Trp Arg Ile Val
        35                  40                  45

Glu Asn Tyr Arg Asn Gly Ala Ala Lys Asp Asp Asn Gln Arg Pro Tyr
    50                  55                  60

Pro Ala Ala Arg His Ala Pro His Pro Glu Tyr Gly Pro Asp Asn Asn
65                  70                  75                  80

Tyr Leu Ile Leu Lys Gly Pro Asp Ala Gln Ser Tyr Ala Ser Gln Tyr
                85                  90                  95

Leu Arg Val Val Gly Gly Thr Thr Trp His Trp Ala Ala Ser Cys Trp
            100                 105                 110

Arg Phe Leu Pro Asn Asp Phe His Met Lys Gln Val Tyr Gly Val Gly
        115                 120                 125

Arg Asp Trp Gly Ile Ser Tyr Ala Asp Leu Glu Pro Trp Tyr Tyr Lys
    130                 135                 140

Ala Glu Leu Glu Leu Gly Val Ser Gly Pro Asn Asp Gly Thr Asp Leu
145                 150                 155                 160

Gly Ser Pro Arg Lys Gln Pro Tyr Pro Met Asp His Leu Pro Leu Ser
                165                 170                 175

Tyr Asn Asp Gln Arg Phe His Asp Val Leu Asn Ala Asn Gly Phe Asn
            180                 185                 190

Leu Val Ala Glu Pro Val Ala Arg Asn Ser Arg Pro Tyr Asp Glu Arg
        195                 200                 205

Pro Thr Cys Cys Gly Asn Asn Asn Cys Met Pro Ile Cys Pro Ile Ala
    210                 215                 220

Ala Met Tyr Ser Gly Ile Ile His Val Leu Lys Ala Glu Arg Ala Gly
225                 230                 235                 240

Thr Arg Leu Leu Thr Asn Ala Val Val Tyr Arg Leu Glu Val Asp Ala
                245                 250                 255

His Asp Asn Ile Ile Ala Ala Leu Tyr Lys Asp Pro Asp Gly Asn Ser
            260                 265                 270

His Arg Val Thr Gly Lys Tyr Phe Val Leu Ala Ala Asn Ala Leu Glu
        275                 280                 285
```

Ser Ala Lys Ile Leu Leu Met Ser Thr Thr Asp Lys Phe Ala Ser Gly
    290                 295                 300

Leu Ala Asn Ser Ser Asp Gln Val Gly Arg Asn Leu Met Asp His Pro
305                 310                 315                 320

Gly Thr Gly Ile Thr Phe Leu Ala Asn Glu Pro Leu Trp Pro Gly Arg
                325                 330                 335

Gly Pro Met Glu Leu Thr Ser Ile Val Asp His Arg Asp Gly Asp Phe
            340                 345                 350

Arg Arg Glu Trp Ala Ser Lys Lys Leu His Leu Asn Asn Gln Ser Gln
        355                 360                 365

Thr Arg Lys Ala Thr Glu Lys Ala Leu Ser Met Gly Leu Val Gly Lys
    370                 375                 380

Lys Leu Asp Glu Glu Ile Arg Tyr Arg Ala Ala His Thr Val Asn Ile
385                 390                 395                 400

Asn Ser Phe His Asp Ile Leu Pro Glu Pro Asp Asn Arg Leu Val Leu
                405                 410                 415

Ser Asp Gln Lys Asp Pro Leu Gly Leu Pro Arg Met Glu Ile Thr Tyr
            420                 425                 430

Lys Ile Gly Asp Tyr Thr Lys Arg Ser Ala Glu His Thr His Glu Ser
        435                 440                 445

Tyr Ala Lys Ile Ala Gln Leu Phe Gly Gly Thr Glu Val Thr Phe Asp
    450                 455                 460

Asp Lys Phe Ala Pro Asn Asn His Leu Met Gly Ser Val Ile Met Gly
465                 470                 475                 480

Gln Asn Pro Lys Asp Ser Val Val Asp Gly Asp Cys Arg Ala His Asp
                485                 490                 495

His Ala Asn Leu Tyr Leu Ala Thr Ser Gly Val Met Ala Ser Ala Gly
            500                 505                 510

Ser Val Asn Cys Thr Leu Thr Ile Ala Ala Leu Ser Leu Arg Ile Ala
        515                 520                 525

Asp Thr Leu Lys Arg Gln Leu Gly Arg Thr Thr Ser
    530                 535                 540

<210> SEQ ID NO 14
<211> LENGTH: 481
<212> TYPE: PRT
<213> ORGANISM: Silvimonas terrae

<400> SEQUENCE: 14

Met Thr Cys Arg Leu Leu Arg Pro Phe Ala Leu Ala Ala Leu Met Leu
1               5                   10                  15

Val Ser Ala Leu Ala Gln Ala Ala Glu Val Ser Pro Glu Gln Ile Lys
            20                  25                  30

Arg Gly Glu Tyr Leu Ala Arg Ala Ala Asp Cys Ile Ala Cys His Thr
        35                  40                  45

Val Pro Arg Thr Gly Gln Pro Phe Ala Gly Gly Tyr Gly Ile Ala Ser
    50                  55                  60

Pro Leu Gly Thr Ile Tyr Ser Ser Asn Ile Thr Pro Ser Thr Ser Ala
65                  70                  75                  80

Gly Ile Gly Asn Tyr Thr Leu Gln Asp Phe Asp Asn Ala Leu Arg Arg
                85                  90                  95

Gly Ile Arg Lys Asp Gly Ala His Leu Tyr Pro Ala Met Pro Tyr Thr
            100                 105                 110

Ala Tyr Ala Lys Leu Gln Pro Glu Asp Val Glu Ala Leu Tyr Ala Tyr
        115                 120                 125

-continued

```
Leu Met His Gly Val Lys Pro Val Asp Ala Gln Pro Arg Arg Thr Arg
    130                 135                 140

Leu Pro Phe Pro Phe Asn Ile Arg Leu Ser Met Ala Val Trp Asn Ser
145                 150                 155                 160

Leu Phe Leu Asp Pro Arg Val Phe Gln Pro Glu Gln Gly Lys Ser Glu
                165                 170                 175

Asp Phe Asn Arg Gly Lys Tyr Leu Val Glu Ala Leu Glu His Cys Ser
            180                 185                 190

Ala Cys His Thr Pro Arg Asn Met Leu Met Ala Glu Asn Pro Asp Ala
        195                 200                 205

Pro Phe Ala Gly Gly Gln Leu Gly Ala Trp Tyr Ala Pro Asn Ile Thr
    210                 215                 220

Ala Asp Pro Val Ser Gly Val Gly Gly Trp Thr Gln Ala Glu Leu Val
225                 230                 235                 240

Gln Tyr Leu Lys Thr Gly His Val Ala Gly Lys Ala Ala Ala Ala Gly
                245                 250                 255

Pro Met Ala Glu Ala Val Ser Asp Ser Leu Ser His Leu Thr Asp Pro
            260                 265                 270

Asp Leu Gln Ala Met Ala Thr Tyr Leu Lys Thr Ile Ala Pro Ile Arg
        275                 280                 285

Asn Thr Ala Asp Ser Lys Pro Ala Trp Ala Trp Gly Ser Pro Ala Asn
    290                 295                 300

Asp Asp Asp Ser Leu Arg Gly Thr Ala Gly Val Thr Gln Ser Asn Arg
305                 310                 315                 320

Pro Thr Ser Ala Ala Glu Leu Phe Ser Ala Asn Cys Ala Ser Cys His
                325                 330                 335

Gln Ala Asn Gly Met Gly Thr Thr Asp Thr Ala Tyr Pro Ser Leu Thr
            340                 345                 350

Asn Asn Thr Ala Leu Gly His Leu Asn Pro Ser Asn Leu Ile Ala Val
        355                 360                 365

Ile Leu Asn Gly Val Asp Arg Pro Leu Pro Asp Gly His His Ala Phe
    370                 375                 380

Met Pro Gly Phe Gly Pro Gly Ser Leu Ile Asn Pro Leu Ser Asp Ala
385                 390                 395                 400

Asp Ile Ala Thr Leu Ala Asn Tyr Thr Leu Gln Arg Phe Gly Asn Thr
                405                 410                 415

Asn Val His Val Thr Pro Glu Glu Val Ala Ala Ser Arg Lys Gly Gly
            420                 425                 430

Glu Pro Pro Leu Leu Ala Lys Leu Pro Arg Val Leu Pro Val Val Leu
        435                 440                 445

Met Leu Phe Ala Leu Leu Leu Ile Leu Gly Gly Trp Arg Ser Ala Arg
    450                 455                 460

Gln Arg Lys Leu Arg His Val Ala Arg Pro Ser Pro Thr Pro Arg Thr
465                 470                 475                 480

Pro
```

<210> SEQ ID NO 15
<211> LENGTH: 3500
<212> TYPE: DNA
<213> ORGANISM: Zymobacter palmae
<220> FEATURE:
<221> NAME/KEY: CDS
<222> LOCATION: (1)..(585)
<220> FEATURE:
<221> NAME/KEY: CDS

```
<222> LOCATION: (592)..(2193)
<220> FEATURE:
<221> NAME/KEY: CDS
<222> LOCATION: (2199)..(3497)

<400> SEQUENCE: 15

atg agt ggg ccg gcc ata ttc ccc gct gtg ttc aat cga cga agc gag       48
Met Ser Gly Pro Ala Ile Phe Pro Ala Val Phe Asn Arg Arg Ser Glu
1               5                   10                  15

atc act gtg aaa gat gac acc ccc ctt acg gat gct ggt gcg gtg gcg       96
Ile Thr Val Lys Asp Asp Thr Pro Leu Thr Asp Ala Gly Ala Val Ala
            20                  25                  30

cct gct ttc tct cag cct gtc ggc gta tcg cgt cgc tgc cta ttg ggt      144
Pro Ala Phe Ser Gln Pro Val Gly Val Ser Arg Arg Cys Leu Leu Gly
        35                  40                  45

ggt gcc gcg ctg gga ctg gca gcg att acg cta ggt gcg ctt ccc gta      192
Gly Ala Ala Leu Gly Leu Ala Ala Ile Thr Leu Gly Ala Leu Pro Val
    50                  55                  60

gcg cag gca gca gac aac gcc caa gat agc gcg ctg gct gac ttc atc      240
Ala Gln Ala Ala Asp Asn Ala Gln Asp Ser Ala Leu Ala Asp Phe Ile
65                  70                  75                  80

cgc gta tca ggt gtg ctg aca gca cgt cag caa ctc aac ccg gtg ctg      288
Arg Val Ser Gly Val Leu Thr Ala Arg Gln Gln Leu Asn Pro Val Leu
                85                  90                  95

tca gga ctc atc ttc ggt gaa atg aag aaa gaa gat ccg gcc ttt gct      336
Ser Gly Leu Ile Phe Gly Glu Met Lys Lys Glu Asp Pro Ala Phe Ala
            100                 105                 110

gat cag ctg tct tcc tta gcg ggc gtt atc cat cag ccg cca gcg cag      384
Asp Gln Leu Ser Ser Leu Ala Gly Val Ile His Gln Pro Pro Ala Gln
        115                 120                 125

tgg agt gct tcc atg acg acg ctg gcg cgt gaa ata acc tcc gtc tgg      432
Trp Ser Ala Ser Met Thr Thr Leu Ala Arg Glu Ile Thr Ser Val Trp
    130                 135                 140

tac acc ggg ttg atc ggg agc gga gac acc atg cgt gtc gtg acg tat      480
Tyr Thr Gly Leu Ile Gly Ser Gly Asp Thr Met Arg Val Val Thr Tyr
145                 150                 155                 160

gaa ggt gcg ctc cag ttt tcg gcg acg aag gat atc ttc att gtg cgc      528
Glu Gly Ala Leu Gln Phe Ser Ala Thr Lys Asp Ile Phe Ile Val Arg
                165                 170                 175

agc tat tgc ccc aat cgt ccc ggt ttc tgg gcc agc caa cct tca gga      576
Ser Tyr Cys Pro Asn Arg Pro Gly Phe Trp Ala Ser Gln Pro Ser Gly
            180                 185                 190

tgg aga gtg tgattc atg gca gga att caa aag gct gac gtt gtc atc       624
Trp Arg Val        Met Ala Gly Ile Gln Lys Ala Asp Val Val Ile
        195                     200                 205

gtt ggc aca ggg gtg gcc ggt gct ctg att gca cat cag ctg gcc aag      672
Val Gly Thr Gly Val Ala Gly Ala Leu Ile Ala His Gln Leu Ala Lys
            210                 215                 220

gcg ggc aag cgt gta ctg atg ctg gaa gcg ggg ccg cgt ctg aca cgt      720
Ala Gly Lys Arg Val Leu Met Leu Glu Ala Gly Pro Arg Leu Thr Arg
        225                 230                 235

ggt gaa att act ggc aac ttt cgt tcc agt gcg ttc aag tcg gat ttt      768
Gly Glu Ile Thr Gly Asn Phe Arg Ser Ser Ala Phe Lys Ser Asp Phe
    240                 245                 250

caa tcg cca tac ccg tgt acc gac tat gcg ccg att ccg acg atg cac      816
Gln Ser Pro Tyr Pro Cys Thr Asp Tyr Ala Pro Ile Pro Thr Met His
255                 260                 265                 270

ccc aag aac gac tac ttc atc caa agc ggt gag cac tcc tac gat gcg      864
Pro Lys Asn Asp Tyr Phe Ile Gln Ser Gly Glu His Ser Tyr Asp Ala
                275                 280                 285
```

-continued

```
cag tac ctg cgc ttg gtt ggt ggt acg act tgg cac tgg gcg gca tcg      912
Gln Tyr Leu Arg Leu Val Gly Gly Thr Thr Trp His Trp Ala Ala Ser
            290                 295                 300

gcg tgg cgc tat ctg ccg gtc gat ttc aag ctg aag agc acc tat ggt      960
Ala Trp Arg Tyr Leu Pro Val Asp Phe Lys Leu Lys Ser Thr Tyr Gly
        305                 310                 315

gtc ggg gtt gac tgg ccc atc gac tac gat gca ctg gag ccg tgg tat     1008
Val Gly Val Asp Trp Pro Ile Asp Tyr Asp Ala Leu Glu Pro Trp Tyr
    320                 325                 330

cag cgt gct gaa gaa gca ctg ggt gtg tgg ggg cct aat gat gaa gag     1056
Gln Arg Ala Glu Glu Ala Leu Gly Val Trp Gly Pro Asn Asp Glu Glu
335                 340                 345                 350

cta ggt tca ccg cgt tcc cag cct tat cca atg acg ccg ctg ccg ctg     1104
Leu Gly Ser Pro Arg Ser Gln Pro Tyr Pro Met Thr Pro Leu Pro Leu
                355                 360                 365

tcc tat aac gaa cac acg atc aag acg cgc ctc aat gcg cag ggg ttc     1152
Ser Tyr Asn Glu His Thr Ile Lys Thr Arg Leu Asn Ala Gln Gly Phe
            370                 375                 380

ggg atc gtg acg gag ccg gtg gcg cgc aat agc cgc ccc tac gat gat     1200
Gly Ile Val Thr Glu Pro Val Ala Arg Asn Ser Arg Pro Tyr Asp Asp
        385                 390                 395

cgc ccc acc tgc tgc ggt aat aac aac tgc atg ccg atc tgc cct att     1248
Arg Pro Thr Cys Cys Gly Asn Asn Asn Cys Met Pro Ile Cys Pro Ile
    400                 405                 410

ggc gcg atg tat ggc ggt atc gtc cat gtc gaa aaa gcc gaa aag gcg     1296
Gly Ala Met Tyr Gly Gly Ile Val His Val Glu Lys Ala Glu Lys Ala
415                 420                 425                 430

ggg gct aaa gtc gtt ccc gag gcg gtg gtg tac cgc atc gag acg ggc     1344
Gly Ala Lys Val Val Pro Glu Ala Val Val Tyr Arg Ile Glu Thr Gly
                435                 440                 445

gat gac aac cgt atc gtg gcg gtg cat tac aag gat ccg aaa ggc gag     1392
Asp Asp Asn Arg Ile Val Ala Val His Tyr Lys Asp Pro Lys Gly Glu
            450                 455                 460

tcg cac cgc gtt gaa ggt aaa tac ttc gtc atc gcg gca aac ggc atc     1440
Ser His Arg Val Glu Gly Lys Tyr Phe Val Ile Ala Ala Asn Gly Ile
        465                 470                 475

gaa acg ccg aag ttg ttg cag att tcg gtc gat agc cgc aat ccg aat     1488
Glu Thr Pro Lys Leu Leu Gln Ile Ser Val Asp Ser Arg Asn Pro Asn
    480                 485                 490

ggt gtg gcc aac agc tct ggc tgg gtg ggt cgc cac ctg atg gac cac     1536
Gly Val Ala Asn Ser Ser Gly Trp Val Gly Arg His Leu Met Asp His
495                 500                 505                 510

ccg ggg atc ggc gta cgc ttc tat gcc aag gaa ccg ttg tgg ccg ggc     1584
Pro Gly Ile Gly Val Arg Phe Tyr Ala Lys Glu Pro Leu Trp Pro Gly
                515                 520                 525

cgt ggg cct cag gaa atg acc tct gcg gtt gcg tgg cgc gat ggg gat     1632
Arg Gly Pro Gln Glu Met Thr Ser Ala Val Ala Trp Arg Asp Gly Asp
            530                 535                 540

ttc cga cgc acg gca gcg ggc aaa aag atc cac cta tcc aac ctg tcg     1680
Phe Arg Arg Thr Ala Ala Gly Lys Lys Ile His Leu Ser Asn Leu Ser
        545                 550                 555

cgt gtc gat cag gtc acc caa gag ctc ctt gcc ggt gat cag ctg att     1728
Arg Val Asp Gln Val Thr Gln Glu Leu Leu Ala Gly Asp Gln Leu Ile
    560                 565                 570

ttc gga aac gcg ctg gaa gag cag atc cgt gat cgc gca gca cgc ttc     1776
Phe Gly Asn Ala Leu Glu Glu Gln Ile Arg Asp Arg Ala Ala Arg Phe
575                 580                 585                 590

gtg cag ttc gac agt ttc cac gaa ata ctg ccg ctt cct gaa aac cgc     1824
Val Gln Phe Asp Ser Phe His Glu Ile Leu Pro Leu Pro Glu Asn Arg
                595                 600                 605
```

-continued

```
att gtg ccg agc aag gtg cat acg gac aaa ctg ggg att ccc aag cct     1872
Ile Val Pro Ser Lys Val His Thr Asp Lys Leu Gly Ile Pro Lys Pro
            610                 615                 620

gaa ttt ttc tac cgc atc gac gat tac gtt aag cgg ggg gca gcg cat     1920
Glu Phe Phe Tyr Arg Ile Asp Asp Tyr Val Lys Arg Gly Ala Ala His
        625                 630                 635

acc cgc gag atg tat gcg cgt gcg gca cag gtc atg ggg ggt acg gat     1968
Thr Arg Glu Met Tyr Ala Arg Ala Ala Gln Val Met Gly Gly Thr Asp
    640                 645                 650

att cag tat gcc gat gac ttt gct aat aac cag cat atc tgc ggt acg     2016
Ile Gln Tyr Ala Asp Asp Phe Ala Asn Asn Gln His Ile Cys Gly Thr
655                 660                 665                 670

gtg atg atg ggg cca acg gcc gaa act ggg gta gtg gat cag cac tgc     2064
Val Met Met Gly Pro Thr Ala Glu Thr Gly Val Val Asp Gln His Cys
                675                 680                 685

cgt acg ttc gat cac gag aac ctg ttt ttg gcc acc agt ggc gtc atg     2112
Arg Thr Phe Asp His Glu Asn Leu Phe Leu Ala Thr Ser Gly Val Met
            690                 695                 700

ccg acg gtg gga acg gtc aac tgt acg ctg act gtg gcg gca ctg tcg     2160
Pro Thr Val Gly Thr Val Asn Cys Thr Leu Thr Val Ala Ala Leu Ser
        705                 710                 715

ctg cgc atg gcc gaa gtc atc aag gcg gag gtg tgatg atg gcg agc aac   2210
Leu Arg Met Ala Glu Val Ile Lys Ala Glu Val       Met Ala Ser Asn
    720                 725                                730

ttt tgg cgg gtg tcg ctg ggt gtg ggg gcg atg gcg gcc ctg tgg atg     2258
Phe Trp Arg Val Ser Leu Gly Val Gly Ala Met Ala Ala Leu Trp Met
    735                 740                 745

agc ggt gtg gcg gca gcg gaa gat gct agt acg cga cag gcc gag ctg     2306
Ser Gly Val Ala Ala Ala Glu Asp Ala Ser Thr Arg Gln Ala Glu Leu
750                 755                 760                 765

gtg aaa cga ggt gag tat gtg gcg cgg acg gcg gac tgt gtg gca tgc     2354
Val Lys Arg Gly Glu Tyr Val Ala Arg Thr Ala Asp Cys Val Ala Cys
                770                 775                 780

cat acc act gat cat gac aag ccc ttt gcg ggt ggt ttg ccg atg ggg     2402
His Thr Thr Asp His Asp Lys Pro Phe Ala Gly Gly Leu Pro Met Gly
            785                 790                 795

ttg ccg atg ggc aac att tat tcg acc aat atc acg ccg gat aag gat     2450
Leu Pro Met Gly Asn Ile Tyr Ser Thr Asn Ile Thr Pro Asp Lys Asp
        800                 805                 810

act ggg atc ggc agc tat acg ttg gag gag ttc aag cgt gtg ctg cgt     2498
Thr Gly Ile Gly Ser Tyr Thr Leu Glu Glu Phe Lys Arg Val Leu Arg
    815                 820                 825

gaa ggg gtg acg ccg gat cga ggc aac ctt tat ccg gcg atg ccg tat     2546
Glu Gly Val Thr Pro Asp Arg Gly Asn Leu Tyr Pro Ala Met Pro Tyr
830                 835                 840                 845

ccg tct tat acc aag atg acc gat gat gaa atc gag gcg ctg tat gcc     2594
Pro Ser Tyr Thr Lys Met Thr Asp Asp Glu Ile Glu Ala Leu Tyr Ala
                850                 855                 860

tat ttc atg cat ggg gtt caa ccg att cat cag gaa aac aag gcg ccg     2642
Tyr Phe Met His Gly Val Gln Pro Ile His Gln Glu Asn Lys Ala Pro
            865                 870                 875

gac ttt tac tgg ccg ctg acc att cgc tgg cct ttg aag ata tgg aac     2690
Asp Phe Tyr Trp Pro Leu Thr Ile Arg Trp Pro Leu Lys Ile Trp Asn
        880                 885                 890

tgg atg ttt ctt gat gaa ggt gcc tat cag ccc aag gcc ggg cag agc     2738
Trp Met Phe Leu Asp Glu Gly Ala Tyr Gln Pro Lys Ala Gly Gln Ser
    895                 900                 905

gat gaa tgg aac cgg ggt gcc tat ctt gtg cag ggg cct gcg cac tgt     2786
Asp Glu Trp Asn Arg Gly Ala Tyr Leu Val Gln Gly Pro Ala His Cys
```

-continued

```
910                 915                 920                 925

ggc acg tgc cat act ccg cgc ggg ctg gca atg cag gag cgc gct tat     2834
Gly Thr Cys His Thr Pro Arg Gly Leu Ala Met Gln Glu Arg Ala Tyr
                930                 935                 940

gat gag aca ggc gac gag tac ttg gcg ggc gct gat atc gcg agc tgg     2882
Asp Glu Thr Gly Asp Glu Tyr Leu Ala Gly Ala Asp Ile Ala Ser Trp
            945                 950                 955

cat gct ttc aac atc act tcg gac atc aac agt ggg atc ggc ggc tgg     2930
His Ala Phe Asn Ile Thr Ser Asp Ile Asn Ser Gly Ile Gly Gly Trp
        960                 965                 970

agt gcc gat gag ctg gtg cag tat ctg aag gat ggc aat gtg cgt ggc     2978
Ser Ala Asp Glu Leu Val Gln Tyr Leu Lys Asp Gly Asn Val Arg Gly
    975                 980                 985

aag ggg cag gcc gga ggg cag atg ggt gag gcg  gtt gaa cac agc ttc    3026
Lys Gly Gln Ala Gly Gly Gln Met Gly Glu Ala  Val Glu His Ser Phe
990                 995                 1000                1005

agt cat atg acc gat  gca gat ctg cat gct  atc gcg gtg tat atg      3071
Ser His Met Thr Asp  Ala Asp Leu His Ala  Ile Ala Val Tyr Met
                1010                 1015                 1020

aag acg gtg cct gcc  gtc aac gat ggc gat  acc cgt cca cgc tat      3116
Lys Thr Val Pro Ala  Val Asn Asp Gly Asp  Thr Arg Pro Arg Tyr
                1025                 1030                 1035

agc tat ggc gct cct  ggc gat gac ttc ctg  cgc ctt cgg gcc cag      3161
Ser Tyr Gly Ala Pro  Gly Asp Asp Phe Leu  Arg Leu Arg Ala Gln
                1040                 1045                 1050

ccc gtt gct caa gat  gcc gca tcg gat cga  ggg gcg cgc gtg tat      3206
Pro Val Ala Gln Asp  Ala Ala Ser Asp Arg  Gly Ala Arg Val Tyr
                1055                 1060                 1065

ctg gag aac tgc gcg  gct tgc cac ggg cct  tcc gga caa ggc tcg      3251
Leu Glu Asn Cys Ala  Ala Cys His Gly Pro  Ser Gly Gln Gly Ser
                1070                 1075                 1080

cct gat ggc tat tat  ccg tcg atg ttc cat  aac agc gtc atc ggt      3296
Pro Asp Gly Tyr Tyr  Pro Ser Met Phe His  Asn Ser Val Ile Gly
                1085                 1090                 1095

acc gat tac cac aac  aac ctc atc aac gtg  gta ttg gat ggc gtg      3341
Thr Asp Tyr His Asn  Asn Leu Ile Asn Val  Val Leu Asp Gly Val
                1100                 1105                 1110

aag cgc aag acc cca  ggc aac gac gtg ctg  atg cca gcc ttc cgc      3386
Lys Arg Lys Thr Pro  Gly Asn Asp Val Leu  Met Pro Ala Phe Arg
                1115                 1120                 1125

gat gag ctg tcc gat  gag gat atc gcg gcg  ttg gct aac tac ctc      3431
Asp Glu Leu Ser Asp  Glu Asp Ile Ala Ala  Leu Ala Asn Tyr Leu
                1130                 1135                 1140

agc cag cag ttc ggg  cgt ggc gat atg aat  gtg acg ccc aaa tcc      3476
Ser Gln Gln Phe Gly  Arg Gly Asp Met Asn  Val Thr Pro Lys Ser
                1145                 1150                 1155

gtc aag gca ctg cgc  aac gat tga                                   3500
Val Lys Ala Leu Arg  Asn Asp
                1160
```

<210> SEQ ID NO 16
<211> LENGTH: 195
<212> TYPE: PRT
<213> ORGANISM: Zymobacter palmae

<400> SEQUENCE: 16

```
Met Ser Gly Pro Ala Ile Phe Pro Ala Val Phe Asn Arg Arg Ser Glu
1               5                   10                  15

Ile Thr Val Lys Asp Asp Thr Pro Leu Thr Asp Ala Gly Ala Val Ala
            20                  25                  30
```

```
Pro Ala Phe Ser Gln Pro Val Gly Val Ser Arg Arg Cys Leu Leu Gly
        35                  40                  45

Gly Ala Ala Leu Gly Leu Ala Ala Ile Thr Leu Gly Ala Leu Pro Val
    50                  55                  60

Ala Gln Ala Ala Asp Asn Ala Gln Asp Ser Ala Leu Ala Asp Phe Ile
65                  70                  75                  80

Arg Val Ser Gly Val Leu Thr Ala Arg Gln Gln Leu Asn Pro Val Leu
                85                  90                  95

Ser Gly Leu Ile Phe Gly Glu Met Lys Lys Glu Asp Pro Ala Phe Ala
            100                 105                 110

Asp Gln Leu Ser Ser Leu Ala Gly Val Ile His Gln Pro Pro Ala Gln
        115                 120                 125

Trp Ser Ala Ser Met Thr Thr Leu Ala Arg Glu Ile Thr Ser Val Trp
    130                 135                 140

Tyr Thr Gly Leu Ile Gly Ser Gly Asp Thr Met Arg Val Val Thr Tyr
145                 150                 155                 160

Glu Gly Ala Leu Gln Phe Ser Ala Thr Lys Asp Ile Phe Ile Val Arg
                165                 170                 175

Ser Tyr Cys Pro Asn Arg Pro Gly Phe Trp Ala Ser Gln Pro Ser Gly
            180                 185                 190

Trp Arg Val
        195


<210> SEQ ID NO 17
<211> LENGTH: 534
<212> TYPE: PRT
<213> ORGANISM: Zymobacter palmae

<400> SEQUENCE: 17

Met Ala Gly Ile Gln Lys Ala Asp Val Val Ile Val Gly Thr Gly Val
1               5                   10                  15

Ala Gly Ala Leu Ile Ala His Gln Leu Ala Lys Ala Gly Lys Arg Val
            20                  25                  30

Leu Met Leu Glu Ala Gly Pro Arg Leu Thr Arg Gly Glu Ile Thr Gly
        35                  40                  45

Asn Phe Arg Ser Ser Ala Phe Lys Ser Asp Phe Gln Ser Pro Tyr Pro
    50                  55                  60

Cys Thr Asp Tyr Ala Pro Ile Pro Thr Met His Pro Lys Asn Asp Tyr
65                  70                  75                  80

Phe Ile Gln Ser Gly Glu His Ser Tyr Asp Ala Gln Tyr Leu Arg Leu
                85                  90                  95

Val Gly Gly Thr Thr Trp His Trp Ala Ala Ser Ala Trp Arg Tyr Leu
            100                 105                 110

Pro Val Asp Phe Lys Leu Lys Ser Thr Tyr Gly Val Gly Val Asp Trp
        115                 120                 125

Pro Ile Asp Tyr Asp Ala Leu Glu Pro Trp Tyr Gln Arg Ala Glu Glu
    130                 135                 140

Ala Leu Gly Val Trp Gly Pro Asn Asp Glu Glu Leu Gly Ser Pro Arg
145                 150                 155                 160

Ser Gln Pro Tyr Pro Met Thr Pro Leu Pro Leu Ser Tyr Asn Glu His
                165                 170                 175

Thr Ile Lys Thr Arg Leu Asn Ala Gln Gly Phe Gly Ile Val Thr Glu
            180                 185                 190

Pro Val Ala Arg Asn Ser Arg Pro Tyr Asp Asp Arg Pro Thr Cys Cys
```

```
        195                 200                 205

Gly Asn Asn Asn Cys Met Pro Ile Cys Pro Ile Gly Ala Met Tyr Gly
    210                 215                 220

Gly Ile Val His Val Glu Lys Ala Glu Lys Ala Gly Ala Lys Val Val
225                 230                 235                 240

Pro Glu Ala Val Val Tyr Arg Ile Glu Thr Gly Asp Asp Asn Arg Ile
                245                 250                 255

Val Ala Val His Tyr Lys Asp Pro Lys Gly Glu Ser His Arg Val Glu
            260                 265                 270

Gly Lys Tyr Phe Val Ile Ala Ala Asn Gly Ile Glu Thr Pro Lys Leu
        275                 280                 285

Leu Gln Ile Ser Val Asp Ser Arg Asn Pro Asn Gly Val Ala Asn Ser
    290                 295                 300

Ser Gly Trp Val Gly Arg His Leu Met Asp His Pro Gly Ile Gly Val
305                 310                 315                 320

Arg Phe Tyr Ala Lys Glu Pro Leu Trp Pro Gly Arg Gly Pro Gln Glu
                325                 330                 335

Met Thr Ser Ala Val Ala Trp Arg Asp Gly Asp Phe Arg Arg Thr Ala
            340                 345                 350

Ala Gly Lys Lys Ile His Leu Ser Asn Leu Ser Arg Val Asp Gln Val
        355                 360                 365

Thr Gln Glu Leu Leu Ala Gly Asp Gln Leu Ile Phe Gly Asn Ala Leu
    370                 375                 380

Glu Glu Gln Ile Arg Asp Arg Ala Ala Arg Phe Val Gln Phe Asp Ser
385                 390                 395                 400

Phe His Glu Ile Leu Pro Leu Pro Glu Asn Arg Ile Val Pro Ser Lys
                405                 410                 415

Val His Thr Asp Lys Leu Gly Ile Pro Lys Pro Glu Phe Phe Tyr Arg
            420                 425                 430

Ile Asp Asp Tyr Val Lys Arg Gly Ala Ala His Thr Arg Glu Met Tyr
        435                 440                 445

Ala Arg Ala Ala Gln Val Met Gly Gly Thr Asp Ile Gln Tyr Ala Asp
    450                 455                 460

Asp Phe Ala Asn Asn Gln His Ile Cys Gly Thr Val Met Met Gly Pro
465                 470                 475                 480

Thr Ala Glu Thr Gly Val Val Asp Gln His Cys Arg Thr Phe Asp His
                485                 490                 495

Glu Asn Leu Phe Leu Ala Thr Ser Gly Val Met Pro Thr Val Gly Thr
            500                 505                 510

Val Asn Cys Thr Leu Thr Val Ala Ala Leu Ser Leu Arg Met Ala Glu
        515                 520                 525

Val Ile Lys Ala Glu Val
    530


<210> SEQ ID NO 18
<211> LENGTH: 433
<212> TYPE: PRT
<213> ORGANISM: Zymobacter palmae

<400> SEQUENCE: 18

Met Ala Ser Asn Phe Trp Arg Val Ser Leu Gly Val Gly Ala Met Ala
1               5                   10                  15

Ala Leu Trp Met Ser Gly Val Ala Ala Ala Glu Asp Ala Ser Thr Arg
            20                  25                  30
```

-continued

```
Gln Ala Glu Leu Val Lys Arg Gly Glu Tyr Val Ala Arg Thr Ala Asp
        35                  40                  45

Cys Val Ala Cys His Thr Thr Asp His Asp Lys Pro Phe Ala Gly Gly
    50                  55                  60

Leu Pro Met Gly Leu Pro Met Gly Asn Ile Tyr Ser Thr Asn Ile Thr
65                  70                  75                  80

Pro Asp Lys Asp Thr Gly Ile Gly Ser Tyr Thr Leu Glu Glu Phe Lys
                85                  90                  95

Arg Val Leu Arg Glu Gly Val Thr Pro Asp Arg Gly Asn Leu Tyr Pro
            100                 105                 110

Ala Met Pro Tyr Pro Ser Tyr Thr Lys Met Thr Asp Asp Glu Ile Glu
        115                 120                 125

Ala Leu Tyr Ala Tyr Phe Met His Gly Val Gln Pro Ile His Gln Glu
    130                 135                 140

Asn Lys Ala Pro Asp Phe Tyr Trp Pro Leu Thr Ile Arg Trp Pro Leu
145                 150                 155                 160

Lys Ile Trp Asn Trp Met Phe Leu Asp Glu Gly Ala Tyr Gln Pro Lys
                165                 170                 175

Ala Gly Gln Ser Asp Glu Trp Asn Arg Gly Ala Tyr Leu Val Gln Gly
            180                 185                 190

Pro Ala His Cys Gly Thr Cys His Thr Pro Arg Gly Leu Ala Met Gln
        195                 200                 205

Glu Arg Ala Tyr Asp Glu Thr Gly Asp Glu Tyr Leu Ala Gly Ala Asp
    210                 215                 220

Ile Ala Ser Trp His Ala Phe Asn Ile Thr Ser Asp Ile Asn Ser Gly
225                 230                 235                 240

Ile Gly Gly Trp Ser Ala Asp Glu Leu Val Gln Tyr Leu Lys Asp Gly
                245                 250                 255

Asn Val Arg Gly Lys Gly Gln Ala Gly Gly Gln Met Gly Glu Ala Val
            260                 265                 270

Glu His Ser Phe Ser His Met Thr Asp Ala Asp Leu His Ala Ile Ala
        275                 280                 285

Val Tyr Met Lys Thr Val Pro Ala Val Asn Asp Gly Asp Thr Arg Pro
    290                 295                 300

Arg Tyr Ser Tyr Gly Ala Pro Gly Asp Asp Phe Leu Arg Leu Arg Ala
305                 310                 315                 320

Gln Pro Val Ala Gln Asp Ala Ala Ser Asp Arg Gly Ala Arg Val Tyr
                325                 330                 335

Leu Glu Asn Cys Ala Ala Cys His Gly Pro Ser Gly Gln Gly Ser Pro
            340                 345                 350

Asp Gly Tyr Tyr Pro Ser Met Phe His Asn Ser Val Ile Gly Thr Asp
        355                 360                 365

Tyr His Asn Asn Leu Ile Asn Val Val Leu Asp Gly Val Lys Arg Lys
    370                 375                 380

Thr Pro Gly Asn Asp Val Leu Met Pro Ala Phe Arg Asp Glu Leu Ser
385                 390                 395                 400

Asp Glu Asp Ile Ala Ala Leu Ala Asn Tyr Leu Ser Gln Gln Phe Gly
                405                 410                 415

Arg Gly Asp Met Asn Val Thr Pro Lys Ser Val Lys Ala Leu Arg Asn
            420                 425                 430

Asp
```

<210> SEQ ID NO 19

<211> LENGTH: 3938
<212> TYPE: DNA
<213> ORGANISM: Cobetia sp.
<220> FEATURE:
<221> NAME/KEY: CDS
<222> LOCATION: (1)..(621)
<220> FEATURE:
<221> NAME/KEY: CDS
<222> LOCATION: (752)..(2362)
<220> FEATURE:
<221> NAME/KEY: CDS
<222> LOCATION: (2368)..(3933)

<400> SEQUENCE: 19

```
atg acc cca cgt gaa aat agt gtt tcg gat gat gtc ccc atg cgc cag       48
Met Thr Pro Arg Glu Asn Ser Val Ser Asp Asp Val Pro Met Arg Gln
1               5                   10                  15

gat ggt cat cat gaa gcg tcc caa gtc gct gag ccg acc agc ccg gca       96
Asp Gly His His Glu Ala Ser Gln Val Ala Glu Pro Thr Ser Pro Ala
            20                  25                  30

cgt cgt cgt ctg ctc aag ctg ggt gtg tcg ggg ctg gga ttg gtg gcg      144
Arg Arg Arg Leu Leu Lys Leu Gly Val Ser Gly Leu Gly Leu Val Ala
        35                  40                  45

ctt tcc agc ctg tca ctt tct gca ctg gcg gcc agt gcc acc tca tca      192
Leu Ser Ser Leu Ser Leu Ser Ala Leu Ala Ala Ser Ala Thr Ser Ser
    50                  55                  60

gag gcg tca tcc ggt gcc gcg tct gat gat gac tca gcc ttc aag gcg      240
Glu Ala Ser Ser Gly Ala Ala Ser Asp Asp Asp Ser Ala Phe Lys Ala
65                  70                  75                  80

ttc atg ctc ctg tca gca tgg tta ctg agc gac aag acg ctg gat aaa      288
Phe Met Leu Leu Ser Ala Trp Leu Leu Ser Asp Lys Thr Leu Asp Lys
                85                  90                  95

cgt ctg ggt gag cgt ttc ttt gag gca ttg gtg cgt atc cct gcc ccc      336
Arg Leu Gly Glu Arg Phe Phe Glu Ala Leu Val Arg Ile Pro Ala Pro
            100                 105                 110

aat gtg cca ggc atg ggt agt ttg ccc gcc ctg aag aac aag ttg ctg      384
Asn Val Pro Gly Met Gly Ser Leu Pro Ala Leu Lys Asn Lys Leu Leu
        115                 120                 125

gca ctt ggc gag gcg cgt gac tat ctg aag gaa gac gat ctc gac gcc      432
Ala Leu Gly Glu Ala Arg Asp Tyr Leu Lys Glu Asp Asp Leu Asp Ala
    130                 135                 140

tcc gag atg cag ttg gtg cga cgt gtc ctc caa gcc tgg atg ctg ggc      480
Ser Glu Met Gln Leu Val Arg Arg Val Leu Gln Ala Trp Met Leu Gly
145                 150                 155                 160

acg gtt ggc act gca att gat gat ccc gcg gcg gaa gtc atc gcc tat      528
Thr Val Gly Thr Ala Ile Asp Asp Pro Ala Ala Glu Val Ile Ala Tyr
                165                 170                 175

gaa tac gcg gcc atg tat gcc ggc cct cgc gat gtg cag atc atc cgc      576
Glu Tyr Ala Ala Met Tyr Ala Gly Pro Arg Asp Val Gln Ile Ile Arg
            180                 185                 190

acc tat tgc cct aac caa ccg ggc ttc tgg gca cag cgt cct gag          621
Thr Tyr Cys Pro Asn Gln Pro Gly Phe Trp Ala Gln Arg Pro Glu
        195                 200                 205

tgatcatgcc tcgtcagtcc tgaccctgat gctgtccctg atacgctttt tgaacttcct    681

gacaacttga ctcgggtact tcccgatcaa gattcacgtc taaaaaatgt tcctctgagg    741

agaatcctgc atg gct gcg gaa tcc cat tcg cat gat gcc gat gtc atc       790
           Met Ala Ala Glu Ser His Ser His Asp Ala Asp Val Ile
                   210                 215                 220

atc gtc ggt tct ggt gtt gct ggc gcc ttg att gcc cac cgg ctt gcc      838
Ile Val Gly Ser Gly Val Ala Gly Ala Leu Ile Ala His Arg Leu Ala
                225                 230                 235
```

-continued

```
gag gca ggt aaa tca gtc atc atg ctt gag gct ggc cct cgc atg cag      886
Glu Ala Gly Lys Ser Val Ile Met Leu Glu Ala Gly Pro Arg Met Gln
            240                 245                 250

cgc tgg cag att gtg gag cgc ttc cgt aat caa gcc gac aag atg gac      934
Arg Trp Gln Ile Val Glu Arg Phe Arg Asn Gln Ala Asp Lys Met Asp
        255                 260                 265

ttc atg ggg cct tat ccg gca agc aag gct gcg cca cac ccg atg ctg      982
Phe Met Gly Pro Tyr Pro Ala Ser Lys Ala Ala Pro His Pro Met Leu
    270                 275                 280

tat ggc gag aat gcc aat tac ctc gtg cag aag ggc gag cag gtc tat     1030
Tyr Gly Glu Asn Ala Asn Tyr Leu Val Gln Lys Gly Glu Gln Val Tyr
285                 290                 295                 300

gac gcg caa tac att cgc gcc gtc ggt ggt act act tgg cac tgg gcg     1078
Asp Ala Gln Tyr Ile Arg Ala Val Gly Gly Thr Thr Trp His Trp Ala
                305                 310                 315

gcg tct gca tgg cgc ttc ctg cct agc gat ttc cgc ttg aaa agc gaa     1126
Ala Ser Ala Trp Arg Phe Leu Pro Ser Asp Phe Arg Leu Lys Ser Glu
            320                 325                 330

tat ggc gtc gga ctg gat tgg ccg att tcc tat gat gac ctg gaa ggc     1174
Tyr Gly Val Gly Leu Asp Trp Pro Ile Ser Tyr Asp Asp Leu Glu Gly
        335                 340                 345

tac tac ttc cgt gcc gag cag gcg ctg ggg gta tgg ggc ccg aat gat     1222
Tyr Tyr Phe Arg Ala Glu Gln Ala Leu Gly Val Trp Gly Pro Asn Asp
    350                 355                 360

gtt gac ctc ggc agc ccg cgc agc gct gat tat ccg atg gca ccg ttg     1270
Val Asp Leu Gly Ser Pro Arg Ser Ala Asp Tyr Pro Met Ala Pro Leu
365                 370                 375                 380

ccg ctg tca tgg aat gag cag cgt gtc agt cag cgg atc aat ccg cat     1318
Pro Leu Ser Trp Asn Glu Gln Arg Val Ser Gln Arg Ile Asn Pro His
                385                 390                 395

ggc ttt gac atg gtc acc gaa cct gtc gcg cgc aac agt cgc ccg tac     1366
Gly Phe Asp Met Val Thr Glu Pro Val Ala Arg Asn Ser Arg Pro Tyr
            400                 405                 410

gac gat cgc ccg acc tgc tgt ggc aac aac aac tgc atg ccg atc tgt     1414
Asp Asp Arg Pro Thr Cys Cys Gly Asn Asn Asn Cys Met Pro Ile Cys
        415                 420                 425

ccg atc ggg gcg atg tac tcc ggc atc atc cat gtc gag aag gcc gaa     1462
Pro Ile Gly Ala Met Tyr Ser Gly Ile Ile His Val Glu Lys Ala Glu
    430                 435                 440

cgt gcg ggt gcc aag ttg atc gac aat gct gtg gtg cac cat ctg gaa     1510
Arg Ala Gly Ala Lys Leu Ile Asp Asn Ala Val Val His His Leu Glu
445                 450                 455                 460

agc gat gcc agc ggc aag atc cgt gaa gtg cgc tat ctc gat ccg cag     1558
Ser Asp Ala Ser Gly Lys Ile Arg Glu Val Arg Tyr Leu Asp Pro Gln
                465                 470                 475

ggc aag gaa cat cgc ctg agc gcg ccc aag gtt gtg ctg gcg gcc aac     1606
Gly Lys Glu His Arg Leu Ser Ala Pro Lys Val Val Leu Ala Ala Asn
            480                 485                 490

ggt atc gaa acg ccc aag ctg atg cag atg tcg gtg aat gca cat acg     1654
Gly Ile Glu Thr Pro Lys Leu Met Gln Met Ser Val Asn Ala His Thr
        495                 500                 505

ccc aat ggt gtc ggc aat cag aat gac atg gtg ggg cgt cac ctg atg     1702
Pro Asn Gly Val Gly Asn Gln Asn Asp Met Val Gly Arg His Leu Met
    510                 515                 520

gat cac ccc ggt acc ggc gtc agc ttc ctg gcc gat gaa gtg ctg tgg     1750
Asp His Pro Gly Thr Gly Val Ser Phe Leu Ala Asp Glu Val Leu Trp
525                 530                 535                 540

gca ggg cgt ggg cct cag gag atg acc tcg atc atc act tgg cgt gat     1798
Ala Gly Arg Gly Pro Gln Glu Met Thr Ser Ile Ile Thr Trp Arg Asp
                545                 550                 555
```

```
ggg gac ttc cgc aag gag tac gcc tcc aag aag ctg cac ctc tcc aac     1846
Gly Asp Phe Arg Lys Glu Tyr Ala Ser Lys Lys Leu His Leu Ser Asn
            560                 565                 570

atg gcg cgt aca cag cag atg acg acg gag gtg ttg tcg gaa acc ccg     1894
Met Ala Arg Thr Gln Gln Met Thr Thr Glu Val Leu Ser Glu Thr Pro
        575                 580                 585

ctg cgc ctg ggc gcc gac ctg cag gcc cag att gac aat cgt gcc agc     1942
Leu Arg Leu Gly Ala Asp Leu Gln Ala Gln Ile Asp Asn Arg Ala Ser
    590                 595                 600

cgt tat gtg caa ctg gat agc ttc cat gag ttg ttg ccg gag ccg tcc     1990
Arg Tyr Val Gln Leu Asp Ser Phe His Glu Leu Leu Pro Glu Pro Ser
605                 610                 615                 620

aat cgc atc acg cca tca aaa aaa cgc gat gcg ctc ggc ctg ccg agg     2038
Asn Arg Ile Thr Pro Ser Lys Lys Arg Asp Ala Leu Gly Leu Pro Arg
                625                 630                 635

cca gaa ttc cgt tat gct atc gat gat tac gtc aag cgc agc gcc gtg     2086
Pro Glu Phe Arg Tyr Ala Ile Asp Asp Tyr Val Lys Arg Ser Ala Val
            640                 645                 650

cat acc cga gaa caa tat gca cgt atc gct cag ctg atg gga ggc acg     2134
His Thr Arg Glu Gln Tyr Ala Arg Ile Ala Gln Leu Met Gly Gly Thr
        655                 660                 665

gat atc gcg ttc cgt gac gaa ttc tcc aac aac cag cat atc tgc ggt     2182
Asp Ile Ala Phe Arg Asp Glu Phe Ser Asn Asn Gln His Ile Cys Gly
    670                 675                 680

acg acc ctg atg gga gac gac ccc aag aag tcc gtg gtg gac cgc gat     2230
Thr Thr Leu Met Gly Asp Asp Pro Lys Lys Ser Val Val Asp Arg Asp
685                 690                 695                 700

tgc cgt gtg cat ggc cat gac aac ctg ttt gtc gcc agc tcc ggc tgc     2278
Cys Arg Val His Gly His Asp Asn Leu Phe Val Ala Ser Ser Gly Cys
                705                 710                 715

atg ccg acc gtt ggg tcg gtc aat tgc acc ctg acc atc gcg gcc ttg     2326
Met Pro Thr Val Gly Ser Val Asn Cys Thr Leu Thr Ile Ala Ala Leu
            720                 725                 730

tct ctc cgt atc gcc gat cag cta gaa cag gaa ata tgagc atg ggc cag   2376
Ser Leu Arg Ile Ala Asp Gln Leu Glu Gln Glu Ile       Met Gly Gln
        735                 740                          745

cca ggt cgt aac gcc gtg aat gat gag agt att gcc aag aaa cgc ctg     2424
Pro Gly Arg Asn Ala Val Asn Asp Glu Ser Ile Ala Lys Lys Arg Leu
        750                 755                 760

atg gtc cgt cct gcg cat cgt cat ctg gga agc gcc att cgt cta gcg     2472
Met Val Arg Pro Ala His Arg His Leu Gly Ser Ala Ile Arg Leu Ala
    765                 770                 775

gca ttt gcc ggc gtc agc aca ctg ctg ttg agt ggt tgt ggc aac ggg     2520
Ala Phe Ala Gly Val Ser Thr Leu Leu Leu Ser Gly Cys Gly Asn Gly
780                 785                 790                 795

gaa gat gag cac gcc aag cag gtt gct gct gac aag gcg gcc acc agt     2568
Glu Asp Glu His Ala Lys Gln Val Ala Ala Asp Lys Ala Ala Thr Ser
                800                 805                 810

gac ccg gcc ttg gtc aag caa ggt ctt tat atg gcg cag gcc agt gac     2616
Asp Pro Ala Leu Val Lys Gln Gly Leu Tyr Met Ala Gln Ala Ser Asp
            815                 820                 825

tgt gct gcc tgc cac acg acc aag gat ggt gaa gac tac gca ggt ggc     2664
Cys Ala Ala Cys His Thr Thr Lys Asp Gly Glu Asp Tyr Ala Gly Gly
        830                 835                 840

ctc ccg ttc gag aca ccg gtc ggt gag att ttc tcc acc aac atc acg     2712
Leu Pro Phe Glu Thr Pro Val Gly Glu Ile Phe Ser Thr Asn Ile Thr
    845                 850                 855

ccg gac acc gag cat ggc atc ggc aac tat acc ctt gag gaa tac acc     2760
Pro Asp Thr Glu His Gly Ile Gly Asn Tyr Thr Leu Glu Glu Tyr Thr
```

-continued

```
860                 865                 870                 875

cgt gtg ctg cgc gaa ggg gaa gca gct gac ggc cat aac ctg tac ccg      2808
Arg Val Leu Arg Glu Gly Glu Ala Ala Asp Gly His Asn Leu Tyr Pro
            880                 885                 890

gcg atg ccg ttc ccg tcc tac gcg cgt ctg acc gat gat gac atc aag      2856
Ala Met Pro Phe Pro Ser Tyr Ala Arg Leu Thr Asp Asp Asp Ile Lys
            895                 900                 905

gcg ctg tat gcg tgg aac atg cat gat gtc acg ccg agc agc gag ccg      2904
Ala Leu Tyr Ala Trp Asn Met His Asp Val Thr Pro Ser Ser Glu Pro
        910                 915                 920

aat cgt gag agc gaa att ccg ttc ccg ctc aac atg cgt tgg ccg atg      2952
Asn Arg Glu Ser Glu Ile Pro Phe Pro Leu Asn Met Arg Trp Pro Met
    925                 930                 935

ggc ctg tgg gaa gaa atc ttc tca ccg ctt gag ccg tgg cag gat gac      3000
Gly Leu Trp Glu Glu Ile Phe Ser Pro Leu Glu Pro Trp Gln Asp Asp
940                 945                 950                 955

gag cag aaa gag gct gac tgg aat cgt ggc gcc tat ctg gtg cag ggc      3048
Glu Gln Lys Glu Ala Asp Trp Asn Arg Gly Ala Tyr Leu Val Gln Gly
            960                 965                 970

ccg ggt cac tgc ggt agc tgc cat acc gaa cgc ggc ctt gcc ttc cag      3096
Pro Gly His Cys Gly Ser Cys His Thr Glu Arg Gly Leu Ala Phe Gln
            975                 980                 985

gag aag gcg ctg acc ggc gat gaa gaa ggg tat ctc ggt  ggt gcg atg     3144
Glu Lys Ala Leu Thr Gly Asp Glu Glu Gly Tyr Leu Gly  Gly Ala Met
        990                 995                 1000

att gaa  ggc tgg cgt gcc ttc  aac ctg acg ccg gac  gtc aag gat      3189
Ile Glu  Gly Trp Arg Ala Phe  Asn Leu Thr Pro Asp  Val Lys Asp
    1005                 1010                 1015

ggc ttg  ggt agc tgg agc gag  cag gat atc gtc acc  tat ctc tcg      3234
Gly Leu  Gly Ser Trp Ser Glu  Gln Asp Ile Val Thr  Tyr Leu Ser
    1020                 1025                 1030

acg ggc  aac ttg aaa ggc aag  gca cag gcg ggt ggc  ccg atg gcg      3279
Thr Gly  Asn Leu Lys Gly Lys  Ala Gln Ala Gly Gly  Pro Met Ala
    1035                 1040                 1045

gat gtc  atc agt cac tcc atg  cgc cat atg act gac  gaa gac ctc      3324
Asp Val  Ile Ser His Ser Met  Arg His Met Thr Asp  Glu Asp Leu
    1050                 1055                 1060

aat gcg  atg gcg gtc tat ctg  aag tca ctg ccc gca  ttg aat ggc      3369
Asn Ala  Met Ala Val Tyr Leu  Lys Ser Leu Pro Ala  Leu Asn Gly
    1065                 1070                 1075

aag ggc  gag cag ggc gag gcg  gtc aat gat gat gac  cgc aag gcg      3414
Lys Gly  Glu Gln Gly Glu Ala  Val Asn Asp Asp Asp  Arg Lys Ala
    1080                 1085                 1090

gag gct  acg gcg cca tct gag  aag cag gcc gac gag  aag ggc tcg      3459
Glu Ala  Thr Ala Pro Ser Glu  Lys Gln Ala Asp Glu  Lys Gly Ser
    1095                 1100                 1105

caa gat  gcc ccg cag gtc gcg  act cgc ttc aat cag  ggc gca ccg      3504
Gln Asp  Ala Pro Gln Val Ala  Thr Arg Phe Asn Gln  Gly Ala Pro
    1110                 1115                 1120

gcc gat  gac gtg ctg ttg ctt  cgt ggg cag ccg ctg  gac aag cgt      3549
Ala Asp  Asp Val Leu Leu Leu  Arg Gly Gln Pro Leu  Asp Lys Arg
    1125                 1130                 1135

ccg gat  gac aag gag ttg atc  ggc cag ctg acg gat  gca acg cct      3594
Pro Asp  Asp Lys Glu Leu Ile  Gly Gln Leu Thr Asp  Ala Thr Pro
    1140                 1145                 1150

ggc gtg  cgt ctg tat ctg ggc  cac tgt gcc atg tgt  cac ggt gct      3639
Gly Val  Arg Leu Tyr Leu Gly  His Cys Ala Met Cys  His Gly Ala
    1155                 1160                 1165

gat ggt  gcg ggt acg caa gac  ggc tac tac ccg tca  ctg ttc cac      3684
```

-continued

```
Asp Gly  Ala Gly Thr Gln Asp  Gly Tyr Tyr Pro Ser  Leu Phe His
    1170                 1175                 1180

aac agt  gtc acc ggc agc gtc  tat ccg gat aat ctg  gcg cag gcc      3729
Asn Ser  Val Thr Gly Ser Val  Tyr Pro Asp Asn Leu  Ala Gln Ala
    1185                 1190                 1195

att ctc  aat ggc gta cag cgt  gag agc aat ggc cac  agt gtc ttc      3774
Ile Leu  Asn Gly Val Gln Arg  Glu Ser Asn Gly His  Ser Val Phe
    1200                 1205                 1210

atg ccg  gcc ttt gac agc agc  ctg aac gac aat gag  ctg atc aat      3819
Met Pro  Ala Phe Asp Ser Ser  Leu Asn Asp Asn Glu  Leu Ile Asn
    1215                 1220                 1225

ctg atg  gac tat ctg gag aat  cgc ttc gga gaa ggc  cat gac agc      3864
Leu Met  Asp Tyr Leu Glu Asn  Arg Phe Gly Glu Gly  His Asp Ser
    1230                 1235                 1240

cag aca  ctg gcc gcg cca gat  gcg cgt cgt cag ctg  ctg agt gac      3909
Gln Thr  Leu Ala Ala Pro Asp  Ala Arg Arg Gln Leu  Leu Ser Asp
    1245                 1250                 1255

aag ctc  aag gat tgg cgt ggc  gag taagc                             3938
Lys Leu  Lys Asp Trp Arg Gly  Glu
    1260                 1265
```

<210> SEQ ID NO 20
<211> LENGTH: 207
<212> TYPE: PRT
<213> ORGANISM: Cobetia sp.

<400> SEQUENCE: 20

```
Met Thr Pro Arg Glu Asn Ser Val Ser Asp Asp Val Pro Met Arg Gln
1               5                   10                  15

Asp Gly His His Glu Ala Ser Gln Val Ala Glu Pro Thr Ser Pro Ala
            20                  25                  30

Arg Arg Arg Leu Leu Lys Leu Gly Val Ser Gly Leu Gly Leu Val Ala
        35                  40                  45

Leu Ser Ser Leu Ser Leu Ser Ala Leu Ala Ala Ser Ala Thr Ser Ser
    50                  55                  60

Glu Ala Ser Ser Gly Ala Ala Ser Asp Asp Asp Ser Ala Phe Lys Ala
65                  70                  75                  80

Phe Met Leu Leu Ser Ala Trp Leu Leu Ser Asp Lys Thr Leu Asp Lys
                85                  90                  95

Arg Leu Gly Glu Arg Phe Phe Glu Ala Leu Val Arg Ile Pro Ala Pro
            100                 105                 110

Asn Val Pro Gly Met Gly Ser Leu Pro Ala Leu Lys Asn Lys Leu Leu
        115                 120                 125

Ala Leu Gly Glu Ala Arg Asp Tyr Leu Lys Glu Asp Asp Leu Asp Ala
    130                 135                 140

Ser Glu Met Gln Leu Val Arg Arg Val Leu Gln Ala Trp Met Leu Gly
145                 150                 155                 160

Thr Val Gly Thr Ala Ile Asp Asp Pro Ala Ala Glu Val Ile Ala Tyr
                165                 170                 175

Glu Tyr Ala Ala Met Tyr Ala Gly Pro Arg Asp Val Gln Ile Ile Arg
            180                 185                 190

Thr Tyr Cys Pro Asn Gln Pro Gly Phe Trp Ala Gln Arg Pro Glu
        195                 200                 205
```

<210> SEQ ID NO 21
<211> LENGTH: 537
<212> TYPE: PRT
<213> ORGANISM: Cobetia sp.

<400> SEQUENCE: 21

Met Ala Ala Glu Ser His Ser His Asp Ala Asp Val Ile Ile Val Gly
1               5                   10                  15

Ser Gly Val Ala Gly Ala Leu Ile Ala His Arg Leu Ala Glu Ala Gly
            20                  25                  30

Lys Ser Val Ile Met Leu Glu Ala Gly Pro Arg Met Gln Arg Trp Gln
        35                  40                  45

Ile Val Glu Arg Phe Arg Asn Gln Ala Asp Lys Met Asp Phe Met Gly
    50                  55                  60

Pro Tyr Pro Ala Ser Lys Ala Ala Pro His Pro Met Leu Tyr Gly Glu
65                  70                  75                  80

Asn Ala Asn Tyr Leu Val Gln Lys Gly Glu Gln Val Tyr Asp Ala Gln
                85                  90                  95

Tyr Ile Arg Ala Val Gly Gly Thr Thr Trp His Trp Ala Ala Ser Ala
            100                 105                 110

Trp Arg Phe Leu Pro Ser Asp Phe Arg Leu Lys Ser Glu Tyr Gly Val
        115                 120                 125

Gly Leu Asp Trp Pro Ile Ser Tyr Asp Asp Leu Glu Gly Tyr Tyr Phe
    130                 135                 140

Arg Ala Glu Gln Ala Leu Gly Val Trp Gly Pro Asn Asp Val Asp Leu
145                 150                 155                 160

Gly Ser Pro Arg Ser Ala Asp Tyr Pro Met Ala Pro Leu Pro Leu Ser
                165                 170                 175

Trp Asn Glu Gln Arg Val Ser Gln Arg Ile Asn Pro His Gly Phe Asp
            180                 185                 190

Met Val Thr Glu Pro Val Ala Arg Asn Ser Arg Pro Tyr Asp Asp Arg
        195                 200                 205

Pro Thr Cys Cys Gly Asn Asn Asn Cys Met Pro Ile Cys Pro Ile Gly
    210                 215                 220

Ala Met Tyr Ser Gly Ile Ile His Val Glu Lys Ala Glu Arg Ala Gly
225                 230                 235                 240

Ala Lys Leu Ile Asp Asn Ala Val Val His His Leu Glu Ser Asp Ala
                245                 250                 255

Ser Gly Lys Ile Arg Glu Val Arg Tyr Leu Asp Pro Gln Gly Lys Glu
            260                 265                 270

His Arg Leu Ser Ala Pro Lys Val Val Leu Ala Ala Asn Gly Ile Glu
        275                 280                 285

Thr Pro Lys Leu Met Gln Met Ser Val Asn Ala His Thr Pro Asn Gly
    290                 295                 300

Val Gly Asn Gln Asn Asp Met Val Gly Arg His Leu Met Asp His Pro
305                 310                 315                 320

Gly Thr Gly Val Ser Phe Leu Ala Asp Glu Val Leu Trp Ala Gly Arg
                325                 330                 335

Gly Pro Gln Glu Met Thr Ser Ile Ile Thr Trp Arg Asp Gly Asp Phe
            340                 345                 350

Arg Lys Glu Tyr Ala Ser Lys Lys Leu His Leu Ser Asn Met Ala Arg
        355                 360                 365

Thr Gln Gln Met Thr Thr Glu Val Leu Ser Glu Thr Pro Leu Arg Leu
    370                 375                 380

Gly Ala Asp Leu Gln Ala Gln Ile Asp Asn Arg Ala Ser Arg Tyr Val
385                 390                 395                 400

Gln Leu Asp Ser Phe His Glu Leu Leu Pro Glu Pro Ser Asn Arg Ile

```
                405                 410                 415

Thr Pro Ser Lys Lys Arg Asp Ala Leu Gly Leu Pro Arg Pro Glu Phe
            420                 425                 430

Arg Tyr Ala Ile Asp Asp Tyr Val Lys Arg Ser Ala Val His Thr Arg
        435                 440                 445

Glu Gln Tyr Ala Arg Ile Ala Gln Leu Met Gly Gly Thr Asp Ile Ala
    450                 455                 460

Phe Arg Asp Glu Phe Ser Asn Asn Gln His Ile Cys Gly Thr Thr Leu
465                 470                 475                 480

Met Gly Asp Asp Pro Lys Lys Ser Val Val Asp Arg Asp Cys Arg Val
                485                 490                 495

His Gly His Asp Asn Leu Phe Val Ala Ser Ser Gly Cys Met Pro Thr
            500                 505                 510

Val Gly Ser Val Asn Cys Thr Leu Thr Ile Ala Ala Leu Ser Leu Arg
        515                 520                 525

Ile Ala Asp Gln Leu Glu Gln Glu Ile
    530                 535


<210> SEQ ID NO 22
<211> LENGTH: 522
<212> TYPE: PRT
<213> ORGANISM: Cobetia sp.

<400> SEQUENCE: 22

Met Gly Gln Pro Gly Arg Asn Ala Val Asn Asp Glu Ser Ile Ala Lys
1               5                   10                  15

Lys Arg Leu Met Val Arg Pro Ala His Arg His Leu Gly Ser Ala Ile
            20                  25                  30

Arg Leu Ala Ala Phe Ala Gly Val Ser Thr Leu Leu Leu Ser Gly Cys
        35                  40                  45

Gly Asn Gly Glu Asp Glu His Ala Lys Gln Val Ala Ala Asp Lys Ala
    50                  55                  60

Ala Thr Ser Asp Pro Ala Leu Val Lys Gln Gly Leu Tyr Met Ala Gln
65                  70                  75                  80

Ala Ser Asp Cys Ala Ala Cys His Thr Thr Lys Asp Gly Glu Asp Tyr
                85                  90                  95

Ala Gly Gly Leu Pro Phe Glu Thr Pro Val Gly Glu Ile Phe Ser Thr
            100                 105                 110

Asn Ile Thr Pro Asp Thr Glu His Gly Ile Gly Asn Tyr Thr Leu Glu
        115                 120                 125

Glu Tyr Thr Arg Val Leu Arg Glu Gly Glu Ala Ala Asp Gly His Asn
    130                 135                 140

Leu Tyr Pro Ala Met Pro Phe Pro Ser Tyr Ala Arg Leu Thr Asp Asp
145                 150                 155                 160

Asp Ile Lys Ala Leu Tyr Ala Trp Asn Met His Asp Val Thr Pro Ser
                165                 170                 175

Ser Glu Pro Asn Arg Glu Ser Glu Ile Pro Phe Pro Leu Asn Met Arg
            180                 185                 190

Trp Pro Met Gly Leu Trp Glu Glu Ile Phe Ser Pro Leu Glu Pro Trp
        195                 200                 205

Gln Asp Asp Glu Gln Lys Glu Ala Asp Trp Asn Arg Gly Ala Tyr Leu
    210                 215                 220

Val Gln Gly Pro Gly His Cys Gly Ser Cys His Thr Glu Arg Gly Leu
225                 230                 235                 240
```

-continued

Ala Phe Gln Glu Lys Ala Leu Thr Gly Asp Glu Glu Gly Tyr Leu Gly
245 250 255

Gly Ala Met Ile Glu Gly Trp Arg Ala Phe Asn Leu Thr Pro Asp Val
260 265 270

Lys Asp Gly Leu Gly Ser Trp Ser Glu Gln Asp Ile Val Thr Tyr Leu
275 280 285

Ser Thr Gly Asn Leu Lys Gly Lys Ala Gln Ala Gly Gly Pro Met Ala
290 295 300

Asp Val Ile Ser His Ser Met Arg His Met Thr Asp Glu Asp Leu Asn
305 310 315 320

Ala Met Ala Val Tyr Leu Lys Ser Leu Pro Ala Leu Asn Gly Lys Gly
325 330 335

Glu Gln Gly Glu Ala Val Asn Asp Asp Asp Arg Lys Ala Glu Ala Thr
340 345 350

Ala Pro Ser Glu Lys Gln Ala Asp Glu Lys Gly Ser Gln Asp Ala Pro
355 360 365

Gln Val Ala Thr Arg Phe Asn Gln Gly Ala Pro Ala Asp Asp Val Leu
370 375 380

Leu Leu Arg Gly Gln Pro Leu Asp Lys Arg Pro Asp Asp Lys Glu Leu
385 390 395 400

Ile Gly Gln Leu Thr Asp Ala Thr Pro Gly Val Arg Leu Tyr Leu Gly
405 410 415

His Cys Ala Met Cys His Gly Ala Asp Gly Ala Gly Thr Gln Asp Gly
420 425 430

Tyr Tyr Pro Ser Leu Phe His Asn Ser Val Thr Gly Ser Val Tyr Pro
435 440 445

Asp Asn Leu Ala Gln Ala Ile Leu Asn Gly Val Gln Arg Glu Ser Asn
450 455 460

Gly His Ser Val Phe Met Pro Ala Phe Asp Ser Ser Leu Asn Asp Asn
465 470 475 480

Glu Leu Ile Asn Leu Met Asp Tyr Leu Glu Asn Arg Phe Gly Glu Gly
485 490 495

His Asp Ser Gln Thr Leu Ala Ala Pro Asp Ala Arg Arg Gln Leu Leu
500 505 510

Ser Asp Lys Leu Lys Asp Trp Arg Gly Glu
515 520

<210> SEQ ID NO 23
<211> LENGTH: 8
<212> TYPE: PRT
<213> ORGANISM: Artificial Sequence
<220> FEATURE:
<223> OTHER INFORMATION: consensus sequence

<400> SEQUENCE: 23

Ala Arg Asn Ser Arg Pro Tyr Asp
1 5

<210> SEQ ID NO 24
<211> LENGTH: 8
<212> TYPE: PRT
<213> ORGANISM: Artificial Sequence
<220> FEATURE:
<223> OTHER INFORMATION: consensus sequence-cys introduced

<400> SEQUENCE: 24

Ala Arg Asn Ser Arg Cys Tyr Asp
1 5

-continued

<210> SEQ ID NO 25
<211> LENGTH: 4
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (3)..(3)
<223> OTHER INFORMATION: Xaa is alanine or glycine

<400> SEQUENCE: 25

Met Pro Xaa Phe
1

<210> SEQ ID NO 26
<211> LENGTH: 7
<212> TYPE: PRT
<213> ORGANISM: Artificial Sequence
<220> FEATURE:
<223> OTHER INFORMATION: consensus sequence-cys introduced
<220> FEATURE:
<221> NAME/KEY: MISC_FEATURE
<222> LOCATION: (2)..(3)
<223> OTHER INFORMATION: Xaa is any L-amino acid
<220> FEATURE:
<221> NAME/KEY: MISC_FEATURE
<222> LOCATION: (6)..(6)
<223> OTHER INFORMATION: Xaa is alanine or glycine

<400> SEQUENCE: 26

Cys Xaa Xaa Met Pro Xaa Phe
1 5

<210> SEQ ID NO 27
<211> LENGTH: 4
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (4)..(4)
<223> OTHER INFORMATION: Xaa is leucine or methionine

<400> SEQUENCE: 27

Tyr Pro Ser Xaa
1

<210> SEQ ID NO 28
<211> LENGTH: 5
<212> TYPE: PRT
<213> ORGANISM: Artificial Sequence
<220> FEATURE:
<223> OTHER INFORMATION: consensus sequence-cys intruduced
<220> FEATURE:
<221> NAME/KEY: MISC_FEATURE
<222> LOCATION: (5)..(5)
<223> OTHER INFORMATION: Xaa is leucine or methionine

<400> SEQUENCE: 28

Cys Tyr Pro Ser Xaa
1 5

<210> SEQ ID NO 29
<211> LENGTH: 8
<212> TYPE: PRT
<213> ORGANISM: Artificial Sequence
<220> FEATURE:

-continued

```
<223> OTHER INFORMATION: consensus sequence
<220> FEATURE:
<221> NAME/KEY: MISC_FEATURE
<222> LOCATION: (2)..(3)
<223> OTHER INFORMATION: Xaa is any L-amino acid
<220> FEATURE:
<221> NAME/KEY: MISC_FEATURE
<222> LOCATION: (5)..(7)
<223> OTHER INFORMATION: Xaa is any L-amino acid

<400> SEQUENCE: 29

Pro Xaa Xaa Trp Xaa Xaa Xaa Pro
1               5


<210> SEQ ID NO 30
<211> LENGTH: 9
<212> TYPE: PRT
<213> ORGANISM: Artificial Sequence
<220> FEATURE:
<223> OTHER INFORMATION: consensus sequence-cys introduced
<220> FEATURE:
<221> NAME/KEY: MISC_FEATURE
<222> LOCATION: (3)..(4)
<223> OTHER INFORMATION: Xaa is any L-amino acid
<220> FEATURE:
<221> NAME/KEY: MISC_FEATURE
<222> LOCATION: (6)..(8)
<223> OTHER INFORMATION: Xaa is any L-amino acid

<400> SEQUENCE: 30

Cys Pro Xaa Xaa Trp Xaa Xaa Xaa Pro
1               5


<210> SEQ ID NO 31
<211> LENGTH: 5
<212> TYPE: PRT
<213> ORGANISM: Artificial Sequence
<220> FEATURE:
<223> OTHER INFORMATION: heme-binding domain
<220> FEATURE:
<221> NAME/KEY: MISC_FEATURE
<222> LOCATION: (2)..(3)
<223> OTHER INFORMATION: Xaa is any L-amino acid

<400> SEQUENCE: 31

Cys Xaa Xaa Cys His
1               5
```